United States Patent
Ishii et al.

(10) Patent No.: US 10,944,055 B2
(45) Date of Patent: Mar. 9, 2021

(54) COMPOUND AND ORGANIC PHOTOELECTRIC DEVICE, IMAGE SENSOR AND ELECTRONIC DEVICE INCLUDING THE SAME

(71) Applicant: Samsung Electronics Co., Ltd., Suwon-si (KR)

(72) Inventors: Norihito Ishii, Suwon-si (KR); Katsunori Shibata, Hwaseong-si (KR); Takkyun Ro, Hwaseong-si (KR); Ohkyu Kwon, Seoul (KR); Sang Mo Kim, Hwaseong-si (KR); Kyung Bae Park, Hwaseong-si (KR); Sung Young Yun, Suwon-si (KR); Dong-Seok Leem, Hwaseong-si (KR); Youn Hee Lim, Hwaseong-si (KR); Yong Wan Jin, Seoul (KR); Yeong Suk Choi, Suwon-si (KR); Jong Won Choi, Yongin-si (KR); Taejin Choi, Suwon-si (KR); Hyesung Choi, Seoul (KR); Chul Joon Heo, Busan (KR)

(73) Assignee: Samsung Electronics Co., Ltd., Gyeonggi-do (KR)

(*) Notice: Subject to any disclaimer, the term of this patent is extended or adjusted under 35 U.S.C. 154(b) by 20 days.

(21) Appl. No.: 16/100,352

(22) Filed: Aug. 10, 2018

(65) Prior Publication Data

US 2019/0051833 A1 Feb. 14, 2019

(30) Foreign Application Priority Data

Aug. 10, 2017 (KR) .................. 10-2017-0101869

(51) Int. Cl.
 *H01L 51/00* (2006.01)
 *C09K 11/06* (2006.01)
 (Continued)

(52) U.S. Cl.
 CPC ........ *H01L 51/0053* (2013.01); *C07D 305/06* (2013.01); *C07D 421/04* (2013.01);
 (Continued)

(58) Field of Classification Search
 CPC .............. H01L 27/302; H01L 51/0061; H01L 51/0067; H01L 51/0072; H01L 51/0074;
 (Continued)

(56) References Cited

U.S. PATENT DOCUMENTS 5,387,487 A    2/1995   Shoshi et al.
6,537,687 B1*   3/2003   Nii .................. C09K 11/06
                                                             252/301.16

(Continued)

FOREIGN PATENT DOCUMENTS

DE   4228783 A1   3/1993
EP   3228623      10/2017
(Continued)

OTHER PUBLICATIONS

STIC Chemical structure search results (Year: 2020).*
(Continued)

*Primary Examiner* — Andrew J Golden
(74) *Attorney, Agent, or Firm* — Harness, Dickey & Pierce, P.L.C.

(57) ABSTRACT

A compound of Chemical Formula 1, and an organic photoelectric device, an image sensor, and an electronic device including the same are disclosed:

(Continued)

[Chemical Formula 1]

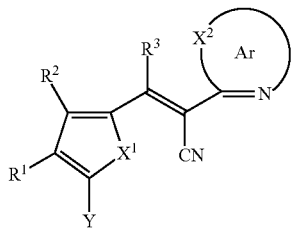

In Chemical Formula 1, each substituent is the same as described in the detailed description.

23 Claims, 8 Drawing Sheets

(51) Int. Cl.
G01J 1/42 (2006.01)
C07D 421/04 (2006.01)
C07D 421/14 (2006.01)
H01L 27/30 (2006.01)
C07D 305/06 (2006.01)
H01L 27/28 (2006.01)
G21K 4/00 (2006.01)
H01L 51/42 (2006.01)
H01L 51/44 (2006.01)

(52) U.S. Cl.
CPC ............ C07D 421/14 (2013.01); C09K 11/06 (2013.01); G01J 1/42 (2013.01); H01L 27/28 (2013.01); H01L 27/307 (2013.01); H01L 51/0071 (2013.01); G21K 2004/06 (2013.01); H01L 51/4253 (2013.01); H01L 51/442 (2013.01); H01L 2251/308 (2013.01)

(58) Field of Classification Search
CPC ... H01L 27/307; H01L 27/28; H01L 51/0071; H01L 51/0053; H01L 51/442; H01L 51/4253; C07D 421/04; C07D 421/14; G01J 1/42
See application file for complete search history.

(56) References Cited

U.S. PATENT DOCUMENTS

| | | | |
|---|---|---|---|
| 8,525,577 B2 | 9/2013 | Yofu et al. | |
| 9,685,616 B2 | 6/2017 | Weiss et al. | |
| 9,941,477 B2 | 4/2018 | Choi et al. | |
| 9,960,362 B2 | 5/2018 | Bulliard et al. | |
| 2003/0170494 A1* | 9/2003 | Nii ...................... | H01L 51/0072 428/690 |
| 2004/0072017 A1* | 4/2004 | Nii ...................... | H01L 51/0073 428/690 |
| 2006/0071253 A1* | 4/2006 | Nii ........................ | H01L 27/307 257/291 |
| 2016/0126470 A1 | 5/2016 | Ro et al. | |
| 2016/0149132 A1 | 5/2016 | Lim et al. | |
| 2017/0294589 A1 | 10/2017 | Shibuya et al. | |

FOREIGN PATENT DOCUMENTS

| | | |
|---|---|---|
| JP | 3-205477 | 9/1991 |
| KR | 2016-0052448 A | 5/2016 |
| KR | 20160048060 A | 5/2016 |
| KR | 2016-0062708 A | 6/2016 |
| KR | 20170060488 A | 6/2017 |
| KR | 20170114839 A | 10/2017 |
| KR | 20170135449 A | 12/2017 |

OTHER PUBLICATIONS

Han, G. et al., "Excimers Beyond Pyrene: A Far-Red Optical Proximity Reporter and its Application to the Label-Free Detection of DNA," Angew. Chem. Int. Ed. 2015, vol. 54, pp. 3912-3916.
Ihama, M. et al., "CMOS Image Sensor with a Thin Overlaid Panchromatic Organic Photoconductive Layer for Sensors with Reduced Pixel Size," IDW '09, INP1-4, pp. 2123-2126.
Aihara, S. et al., "Stacked Image Sensor With Green- and Red-Sensitive Organic Photoconductive Films Applying Zinc Oxide Thin-Film Transistors to a Signal Readout Circuit," IEEE Transactions on Electron Devices, vol. 56, No. 11, Nov. 2009, pp. 2570-2576.
Seo, H. et al., "Color Sensors with Three Vertically Stacked Organic Photodetectors," Japanese Journal of Applied Physics, vol. 46, No. 49, 2007, pp. L1240-L1242.
Search Report for corresponding European Application No. 18188464.4 dated Nov. 19, 2018.
Srilakshmi, R. et al., "Mycobacterium tuberculosislysine-[epsilon]-aminotransferase a potential target in democracy; Benzothiazole based inhibitors", Bioorganic & Medical Chemistry, Pergamon, GB, vol. 25, No. 10, pp. 2761-2771, Feb. 5, 2019.
Saczewski, F. et al., "Synthesis, X-ray crystal sstructures, stabilities, and in vitro cytotoxic activities of new heteroarylacrylonitriles", Journal of Medicinal Chemistry, vol. 47, No. 13, pp. 3438-3449, Feb. 5, 2019.

* cited by examiner

COMPOUND AND ORGANIC PHOTOELECTRIC DEVICE, IMAGE SENSOR AND ELECTRONIC DEVICE INCLUDING THE SAME

CROSS-REFERENCE TO RELATED APPLICATION

This application claims priority to Korean Patent Application No. 10-2017-0101869, filed in the Korean Intellectual Property Office on Aug. 10, 2017, and all the benefits accruing therefrom under 35 U.S.C. § 119, the content of which is incorporated herein in its entirety by reference.

BACKGROUND

1. Field

Example embodiments relate to a compound and an organic photoelectric device, an image sensor, and/or an electronic device including the same.

2. Description of Related Art

A photoelectric device may convert light into an electrical signal using photoelectric effects. A photoelectric device may include a photodiode, a phototransistor, etc., and may be applied to an image sensor, etc.

An image sensor including a photodiode may require high resolution and thus a small pixel. At present, a silicon photodiode is widely used. In some cases, a silicon photodiode exhibits a problem of deteriorated sensitivity because of a relatively small absorption area due to relatively small pixels. Accordingly, an organic material that is capable of replacing silicon has been researched.

An organic material may have a relatively high extinction coefficient and may selectively absorb light in a particular wavelength region depending on a molecular structure, and thus may simultaneously replace a photodiode and a color filter and resultantly improve sensitivity and contribute to relatively high integration.

SUMMARY

Example embodiments provide a compound capable of selectively absorbing light in a green wavelength region and having improved deposition stability, heat resistance, and oxidation resistance.

Example embodiments also provide an organic photoelectric device capable of selectively absorbing light in a green wavelength region and improving efficiency.

Example embodiments also provide an image sensor including the organic photoelectric device.

Example embodiments also provide an electronic device including the image sensor.

According to example embodiments, a compound represented by Chemical Formula 1 is provided.

[Chemical Formula 1]

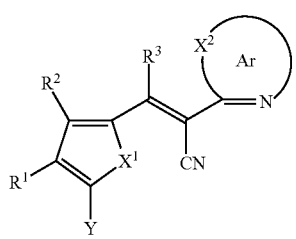

In Chemical Formula 1, $X^1$ may be one of S, Se, Te, O, S($=$O), S($=$O)$_2$, $NR^{a1}$, $SiR^{b1}R^{c1}$, or $GeR^{d1}R^{e1}$ (wherein $R^{a1}$, $R^{b1}$, $R^{c1}$, $R^{d1}$, and $R^{e1}$ independently may be one of hydrogen, a substituted C1 to C10 alkyl group, or an unsubstituted C1 to C10 alkyl group), Ar may be an aromatic ring group including N and $X^2$ (wherein $X^2$ may be one of S, Se, Te, O, S($=$O), S($=$O)$_2$, N, $NR^{a2}$, $CR^{b2}$, $CR^{c2}R^{d2}$, $SiR^{e2}R^{f2}$, or $GeR^{g2}R^{h2}$, and $R^{a2}$, $R^{b2}$, $R^{c2}$, $R^{d2}$, $R^{e2}$, $R^{f2}$, $R^{g2}$, and $R^{h2}$ independently may be one of hydrogen, a substituted C1 to C10 alkyl group, or an unsubstituted C1 to C10 alkyl group), $R^1$ to $R^3$ independently may be one of hydrogen, deuterium, a substituted C1 to C30 alkyl group, an unsubstituted C1 to C30 alkyl group, a substituted C1 to C30 alkoxy group, an unsubstituted C1 to C30 alkoxy group, a substituted C6 to C30 aryl group, an unsubstituted C6 to C30 aryl group, a substituted C3 to C30 heteroaryl group, an unsubstituted C3 to C30 heteroaryl group, a substituted C2 to C30 acyl group, an unsubstituted C2 to C30 acyl group, a halogen, a cyano group (—CN), a cyano-containing group, a nitro group, —$SiR^aR^bR^c$ (wherein $R^a$, $R^b$, and $R^c$ independently may be one of hydrogen, a substituted C1 to C10 alkyl group, or an unsubstituted C1 to C10 alkyl group), or a combination thereof, and Y may be a functional group represented by Chemical Formula 2A or Chemical Formula 2B.

[Chemical Formula 2A]

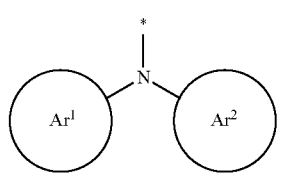

In Chemical Formula 2A, $Ar^1$ and $Ar^2$ independently may be one of a substituted C6 to C30 aryl group, an unsubstituted C6 to C30 aryl group, a substituted C3 to C30 heteroaryl group or an unsubstituted C3 to C30 heteroaryl group.

[Chemical Formula 2B]

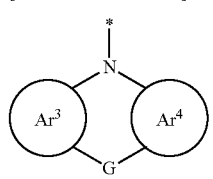

In Chemical Formula 2B, $Ar^3$ and $Ar^4$ independently may be one of a substituted C6 to C30 arylene group, an unsubstituted C6 to C30 arylene group, a substituted C3 to C30 heteroarylene group or unsubstituted C3 to C30 heteroarylene group, and G may be one of a single bond, S, Se, Te, O, $NR^{a3}$, $(CR^{b3}R^{c3})_n$, $(C(R^{d3})=C(R^{e3}))$, $SiR^{f3}R^{g3}$, or $GeR^{h3}R^{i3}$ (wherein $R^{a3}$, $R^{b3}$, $R^{c3}$, $R^{d3}$, $R^{e3}$, $R^{f3}$, $R^{g3}$, $R^{h3}$, and $R^{i3}$ independently may be one of hydrogen, a halogen, a substituted C1 to C10 alkyl group, an unsubstituted C1 to C10 alkyl group, a substituted C6 to C10 aryl group, or an unsubstituted C6 to C10 aryl group, and optionally $R^{d3}$ and $R^{e3}$ independently may be present or may be linked with each other to provide a fused ring, and n may be an integer of 1 or 2).

In some example embodiments, in Chemical Formula 1, Ar may be represented by one of the structures in Chemical Formula 3A to Chemical Formula 3E.

[Chemical Formula 3A]

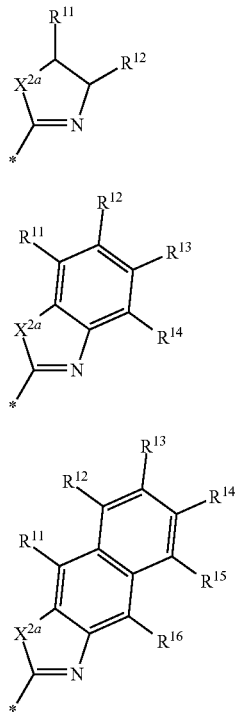

In Chemical Formula 3A, $X^{2a}$ may be one of S, Se, Te, O, S(=O), S(=O)$_2$, $NR^{a2}$, $CR^{c2}R^{d2}$, $SiR^{e2}R^{f2}$, or $GeR^{g2}R^{h2}$ (wherein $R^{a2}$, $R^{c2}$, $R^{d2}$, $R^{e2}$, $R^{f2}$, $R^{g2}$, and $R^{h2}$ independently may be one of hydrogen, a substituted C1 to C10 alkyl group, or an unsubstituted C1 to C10 alkyl group), $R^{11}$ to $R^{16}$ independently may be one of hydrogen, deuterium, a substituted C1 to C30 alkyl group, an unsubstituted C1 to C30 alkyl group, a substituted C1 to C30 alkoxy group, an unsubstituted C1 to C30 alkoxy group, a substituted C6 to C30 aryl group, an unsubstituted C6 to C30 aryl group, a substituted C3 to C30 heteroaryl group, an unsubstituted C3 to C30 heteroaryl group, a substituted C2 to C30 acyl group, an unsubstituted C2 to C30 acyl group, a halogen, a cyano group (—CN), a cyano-containing group, a nitro group, —$SiR^aR^bR^c$ (wherein $R^a$, $R^b$, and $R^c$ independently may be one of hydrogen, a substituted C1 to C10 alkyl group, or an unsubstituted C1 to C10 alkyl group), or a combination thereof, wherein $R^{11}$ to $R^{16}$ independently may be present or an adjacent two thereof may be linked with each other to provide a fused ring.

[Chemical Formula 3B]

(1)

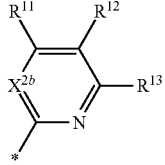

(2)

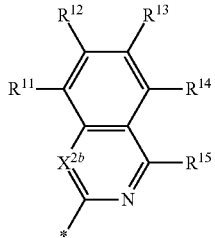

(3)

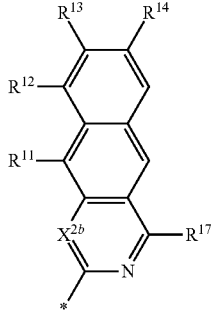

(4)

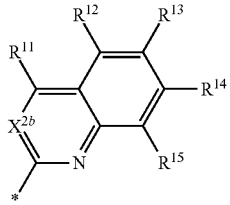

(5)

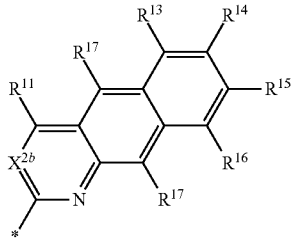

In Chemical Formula 3B, $X^{2b}$ may be one of N or $CR^{b2}$ (wherein $R^{b2}$ may be one of hydrogen, a substituted C1 to C10 alkyl group, or an unsubstituted C1 to C10 alkyl group), and $R^{11}$ to $R^{17}$ independently may be one of hydrogen, deuterium, a substituted C1 to C30 alkyl group, an unsubstituted C1 to C30 alkyl group, a substituted C1 to C30 alkoxy group, an unsubstituted C1 to C30 alkoxy group, a substituted C6 to C30 aryl group, an unsubstituted C6 to C30 aryl group, a substituted C3 to C30 heteroaryl group, an unsubstituted C3 to C30 heteroaryl group, a substituted C2 to C30 acyl group, an unsubstituted C2 to C30 acyl group, a halogen, a cyano group (—CN), a cyano-containing group, a nitro group, —SiR$^a$R$^b$R$^c$ (wherein R$^a$, R$^b$, and R$^c$ independently may be one of hydrogen, a substituted C1 to C10 alkyl group, or an unsubstituted C1 to C10 alkyl group), or a combination thereof, wherein R$^{11}$ to R$^{17}$ and R$^{b2}$ independently may be present or an adjacent two thereof may be linked with each other to provide a fused ring.

[Chemical Formula 3C]

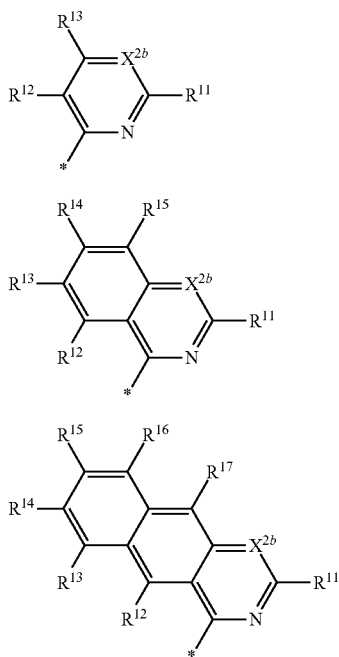

In Chemical Formula 3C,

X$^{2b}$ may be one of N or CR$^{b2}$ (wherein, R$^{b2}$ may be one of hydrogen, a substituted C1 to C10 alkyl group, or an unsubstituted C1 to C10 alkyl group), R$^{11}$ to R$^{17}$ independently may be one of hydrogen, deuterium, a substituted C1 to C30 alkyl group, an unsubstituted C1 to C30 alkyl group, a substituted C1 to C30 alkoxy group, or an unsubstituted C1 to C30 alkoxy group, a substituted C6 to C30 aryl group, an unsubstituted C6 to C30 aryl group, a substituted C3 to C30 heteroaryl group, an unsubstituted C3 to C30 heteroaryl group, a substituted C2 to C30 acyl group, an unsubstituted C2 to C30 acyl group, a halogen, a cyano group (—CN), a cyano-containing group, a nitro group, —SiR$^a$R$^b$R$^c$ (wherein R$^a$, R$^b$, and R$^c$ independently may be one of hydrogen, a substituted C1 to C10 alkyl group, or an unsubstituted C1 to C10 alkyl group), or a combination thereof, wherein R$^{11}$ to R$^{17}$ and R$^{b2}$ independently may be present or an adjacent two thereof may be linked with each other to provide a fused ring.

[Chemical Formula 3D]

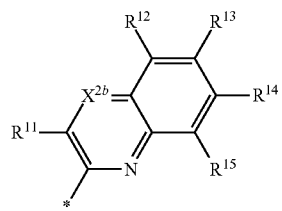

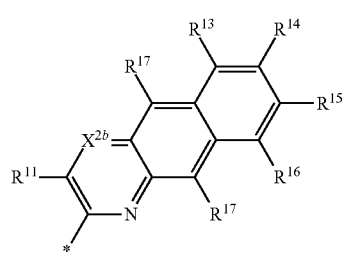

In Chemical Formula 3D,

X$^{2b}$ may be one of N or CR$^{b2}$ (wherein, R$^{b2}$ may be one of hydrogen, a substituted C1 to C10 alkyl group, or an unsubstituted C1 to C10 alkyl group), and R$^{11}$ to R$^{17}$ independently may be one of hydrogen, deuterium, a substituted C1 to C30 alkyl group, an unsubstituted C1 to C30 alkyl group, a substituted C1 to C30 alkoxy group, an unsubstituted C1 to C30 alkoxy group, a substituted C6 to C30 aryl group, an unsubstituted C6 to C30 aryl group, a substituted C3 to C30 heteroaryl group, an unsubstituted C3 to C30 heteroaryl group, a substituted C2 to C30 acyl group, an unsubstituted C2 to C30 acyl group, a halogen, a cyano group (—CN), a cyano-containing group, a nitro group, —SiR$^a$R$^b$R$^c$ (wherein R$^a$, R$^b$, and R$^c$ independently may be one of hydrogen, a substituted C1 to C10 alkyl group, or an unsubstituted C1 to C10 alkyl group), or a combination thereof, wherein R$^{11}$ to R$^{17}$ and R$^{b2}$ independently may be present or an adjacent two thereof may be linked with each other to provide a fused ring.

[Chemical Formula 3E]

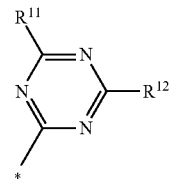

In Chemical Formula 3E,

R$^{11}$ and R$^{12}$ independently may be one of hydrogen, deuterium, a substituted C1 to C30 alkyl group, an unsubstituted C1 to C30 alkyl group, a substituted C1 to C30 alkoxy group, an unsubstituted C1 to C30 alkoxy group, a substituted C6 to C30 aryl group, an unsubstituted C6 to C30 aryl group, a substituted C3 to C30 heteroaryl group, an unsubstituted C3 to C30 heteroaryl group, a substituted C2 to C30 acyl group, an unsubstituted C2 to C30 acyl group, a halogen, a cyano group (—CN), a cyano-containing group, a nitro group, —SiR$^a$R$^b$R$^c$ (wherein R$^a$, R$^b$, and R$^c$ independently may be one of hydrogen, a substituted C1 to C10 alkyl group, or an unsubstituted C1 to C10 alkyl group), or a combination thereof.

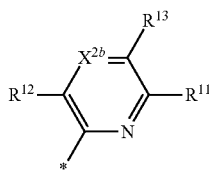

In some example embodiments, Chemical Formula 2A, at least one of $Ar^1$ and $Ar^2$ may include a heteroatom selected from nitrogen (N), sulfur (S), and selenium (Se).

In some example embodiments, Chemical Formula 2B, at least one of $Ar^3$ and $Ar^4$ may include a heteroatom selected from nitrogen (N), sulfur (S), and selenium (Se).

In some example embodiments, Chemical Formula 1, Y may be a functional group represented by one of Chemical Formula 2A-1, Chemical Formula 2A-2, Chemical Formula 2B-1, or Chemical Formula 2B-2.

[Chemical Formula 2A-1]

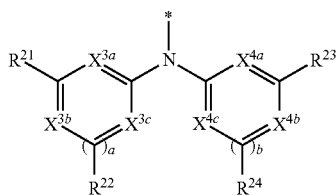

In Chemical Formula 2A-1, $X^{3a}$, $X^{3b}$, $X^{3c}$, $X^{4a}$, $X^{4b}$, and $X^{4c}$ independently may be one of N or $CR^a$ (wherein $R^a$ may be one of hydrogen, a substituted C1 to C10 alkyl group, or an unsubstituted C1 to C10 alkyl group), $R^{21}$, $R^{22}$, $R^{23}$, and $R^{24}$ independently may be one of hydrogen, deuterium, a substituted C1 to C30 alkyl group, an unsubstituted C1 to C30 alkyl group, a substituted C1 to C30 alkoxy group, an unsubstituted C1 to C30 alkoxy group, a substituted C6 to C30 aryl group, an unsubstituted C6 to C30 aryl group, a substituted C3 to C30 heteroaryl group, an unsubstituted C3 to C30 heteroaryl group, a halogen, a cyano group (—CN), a cyano-containing group, or a combination thereof, and a and b independently may be an integer of 0 or 1.

[Chemical Formula 2A-2]

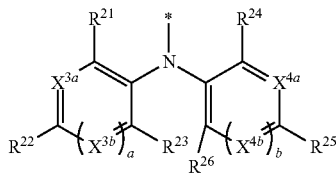

In Chemical Formula 2A-2, $X^{3a}$, $X^{3b}$, $X^{4a}$, and $X^{4b}$ independently may be one of N or $CR^a$ (wherein $R^a$ may be one of hydrogen, a substituted C1 to C10 alkyl group, or an unsubstituted C1 to C10 alkyl group), $R^{21}$, $R^{22}$, $R^{23}$, $R^{24}$, $R^{25}$, and $R^{26}$ independently may be one of hydrogen, deuterium, a substituted C1 to C30 alkyl group, an unsubstituted C1 to C30 alkyl group, a substituted C1 to C30 alkoxy group, an unsubstituted C1 to C30 alkoxy group, a substituted C6 to C30 aryl group, an unsubstituted C6 to C30 aryl group, a substituted C3 to C30 heteroaryl group, an unsubstituted C3 to C30 heteroaryl group, a halogen, a cyano group (—CN), a cyano-containing group, or a combination thereof, and a and b independently may be an integer of 0 or 1.

[Chemical Formula 2B-1]

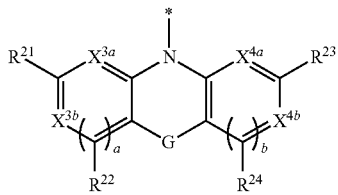

In Chemical Formula 2B-1, $X^{3a}$, $X^{3b}$, $X^{4a}$, and $X^{4b}$ independently may be one of N or $CR^a$ (wherein $R^a$ may be one of hydrogen, a substituted C1 to C10 alkyl group, or an unsubstituted C1 to C10 alkyl group), $R^{21}$, $R^{22}$, $R^{23}$, and $R^{24}$ independently may be one of hydrogen, deuterium, a substituted C1 to C30 alkyl group, an unsubstituted C1 to C30 alkyl group, a substituted C1 to C30 alkoxy group, an unsubstituted C1 to C30 alkoxy group, a substituted C6 to C30 aryl group, an unsubstituted C6 to C30 aryl group, a substituted C3 to C30 heteroaryl group, an unsubstituted C3 to C30 heteroaryl group, a halogen, a cyano group (—CN), a cyano-containing group, or a combination thereof, a and b independently may be an integer of 0 or 1, and G may be one of a single bond, S, Se, Te, O, $NR^{a3}$, $(CR^{b3}R^{c3})_n$, $(C(R^{d3})=C(R^{e3}))$, $SiR^{f3}R^{g3}$, or $GeR^{h3}R^{i3}$ (wherein $R^{a3}$, $R^{b3}$, $R^{c3}$, $R^{d3}$, $R^{e3}$, $R^{f3}$, $R^{g3}$, $R^{h3}$, and $R^{i3}$ independently may be one of hydrogen, a halogen, a substituted C1 to C10 alkyl group, an unsubstituted C1 to C10 alkyl group, a substituted C6 to C10 aryl group, or an unsubstituted C6 to C10 aryl group, and optionally $R^{d3}$ and $R^{e3}$ independently may be present or may be linked with each other to provide a fused ring, and n may be an integer of 1 or 2).

[Chemical Formula 2B-2]

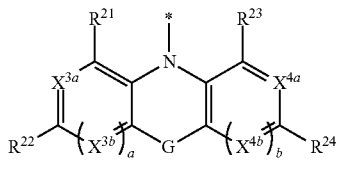

In Chemical Formula 2B-2, $X^{3a}$, $X^{3b}$, $X^{4a}$, and $X^{4b}$ independently may be one of N or $CR^a$ (wherein $R^a$ may be one of hydrogen, a substituted C1 to C10 alkyl group, or an unsubstituted C1 to C10 alkyl group), $R^{21}$, $R^{22}$, $R^{23}$, and $R^{24}$ independently may be one of hydrogen, deuterium, a substituted C1 to C30 alkyl group, or an unsubstituted C1 to C30 alkyl group, a substituted C1 to C30 alkoxy group, or an unsubstituted C1 to C30 alkoxy group, a substituted C6 to C30 aryl group, an unsubstituted C6 to C30 aryl group, a substituted C3 to C30 heteroaryl group, an unsubstituted C3 to C30 heteroaryl group, a halogen, a cyano group (—CN), a cyano-containing group, or a combination thereof, a and b independently may be an integer of 0 or 1, and G may be one of a single bond, S, Se, Te, O, $NR^{a3}$, $(CR^{b3}R^{c3})_n$, $(C(R^{d3})=C(R^{e3}))$, $SiR^{f3}R^{g3}$, or $GeR^{h3}R^{i3}$ (wherein $R^{a3}$, $R^{b3}$, $R^{c3}$, $R^{d3}$, $R^{e3}$, $R^{f3}$, $R^{g3}$, $R^{h3}$, and $R^{i3}$ independently may be one of hydrogen, a halogen, a substituted C1 to C10 alkyl group, an unsubstituted C1 to C10 alkyl group, a substituted C6 to C10 aryl group, or an unsubstituted C6 to C10 aryl group, and optionally $R^{d3}$ and $R^{e3}$ independently may be present or may be linked with each other to provide a fused ring, and n may be an integer of 1 or 2).

In some example embodiments, the compound may have a maximum absorption wavelength ($\lambda_{max}$) in a wavelength region of greater than or equal to about 500 nm and less than about 560 nm, for example about 510 nm to about 550 nm in a thin film state.

In some example embodiments, the compound may exhibit a light absorption curve having a full width at half maximum (FWHM) of about 50 nm to about 120 nm, in a thin film state.

In some example embodiments, a temperature (e.g., deposition temperature) at which 10 wt % of an initial weight of the compound may be lost may be greater than or equal to about 230° C.

According to some example embodiments, an organic photoelectric device includes a first electrode and a second electrode facing each other and an active layer interposed between the first electrode and the second electrode. The active layer may include the compound represented by Chemical Formula 1.

In some example embodiments, the active layer may have a maximum absorption wavelength ($\lambda_{max}$) in a wavelength region of greater than or equal to about 500 nm and less than about 560 nm, for example about 510 nm to about 550 nm.

In some example embodiments, the active layer may exhibit a light absorption curve having a full width at half maximum (FWHM) of about 50 nm to about 120 nm, in a thin film state.

According to some example embodiments, an image sensor may include the organic photoelectric device.

In some example embodiments, the image sensor may include a semiconductor substrate integrated with a plurality of first photo-sensing devices configured to sense light in a blue wavelength region and a plurality of second photo-sensing devices configured to sense light in a red wavelength region, and the organic photoelectric device on the semiconductor substrate and configured to selectively sense light in a green wavelength region.

In some example embodiments, the first photo-sensing device and the second photo-sensing device may be stacked in a vertical direction in the semiconductor substrate.

In some example embodiments, the image sensor may further include a color filter layer between the semiconductor substrate and the organic photoelectric device. The color filter layer may include a blue filter configured to selectively transmit light in a blue wavelength region and a red filter configured to selectively transmit light in a red wavelength region.

In some example embodiments, the image sensor may further include a blue photoelectric device and red photoelectric device. The organic photoelectric device may include a green photoelectric device. The green photoelectric device, the blue photoelectric device, and the red photoelectric device may be stacked. The blue photoelectric device may be configured to selectively sense light in a blue wavelength region. The red photoelectric device may be configured to selectively sense light in a red wavelength region. The green photoelectric device may be configured to selectively sense light in a green wavelength region.

According to some example embodiments, an electronic device includes the image sensor.

According to example embodiments, a compound represented by Chemical Formula 1 may be provided.

[Chemical Formula 1]

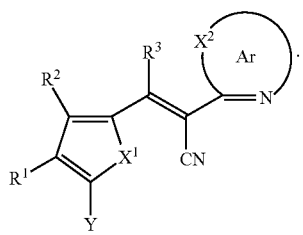

In Chemical Formula 1, $X^1$ may be one of S, Se, Te, O, S(=O), S(=O)$_2$, NR$^{a1}$, SiR$^{b1}$R$^{c1}$, or GeR$^{d1}$R$^{e1}$ (wherein R$^{a1}$, R$^{b1}$, R$^{c1}$, R$^{d1}$, and R$^{e1}$ independently may be one of hydrogen, a substituted C1 to C10 alkyl group, or an unsubstituted C1 to C10 alkyl group), $R^1$ to $R^3$ independently may be one of hydrogen, deuterium, a substituted C1 to C30 alkyl group, an unsubstituted C1 to C30 alkyl group, a substituted C1 to C30 alkoxy group, an unsubstituted C1 to C30 alkoxy group, a substituted C6 to C30 aryl group, an unsubstituted C6 to C30 aryl group, a substituted C3 to C30 heteroaryl group, an unsubstituted C3 to C30 heteroaryl group, a substituted C2 to C30 acyl group, an unsubstituted C2 to C30 acyl group, a halogen, a cyano group (—CN), a cyano-containing group, a nitro group, —SiR$^a$R$^b$R$^c$ (wherein R$^a$, R$^b$, and R$^c$ independently may be one of hydrogen, a substituted C1 to C10 alkyl group, or an unsubstituted C1 to C10 alkyl group), or a combination thereof, and Y may be a functional group represented by Chemical Formula 2A or Chemical Formula 2B.

[Chemical Formula 2A]

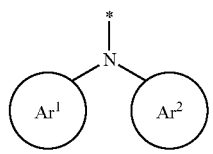

In Chemical Formula 2A, Ar$^1$ and Ar$^2$ independently may be one of a substituted C6 to C30 aryl group, an unsubstituted C6 to C30 aryl group, a substituted C3 to C30 heteroaryl group, or an unsubstituted C3 to C30 heteroaryl group.

[Chemical Formula 2B]

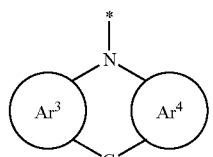

In Chemical Formula 2B, Ar$^3$ and Ar$^4$ independently may be one of a substituted C6 to C30 arylene group, an unsubstituted C6 to C30 arylene group, a substituted C3 to C30 heteroarylene group, or an unsubstituted C3 to C30 heteroarylene group. G may be one of a single bond, S, Se, Te, O, NR$^{a3}$, (CR$^{b3}$R$^{c3}$)$_n$, (C(R$^{d3}$)=C(R$^{e3}$)), SiR$^{f3}$R$^{g3}$, or GeR$^{h3}$R$^{i3}$ (wherein R$^{a3}$, R$^{b3}$, R$^{c3}$, R$^{d3}$, R$^{e3}$, R$^{f3}$, R$^{g3}$, R$^{h3}$, and R$^{i3}$ independently may be one of hydrogen, a halogen, a substituted C1 to C10 alkyl group, an unsubstituted C1 to C10 alkyl group, a substituted C6 to C10 aryl group, or an unsubstituted C6 to C10 aryl group, and optionally $R^{d3}$ and $R^{e3}$ independently may be present or may be linked with each other to provide a fused ring, and n may be an integer of 1 or 2).

In Chemical Formula 1, Ar may include one of the structures represented by Chemical Formulae 3A to 3E.

[Chemical Formula 3A]

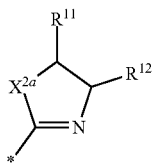
(1)

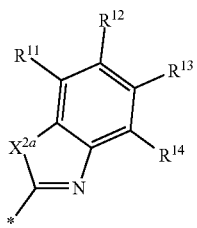
(2)

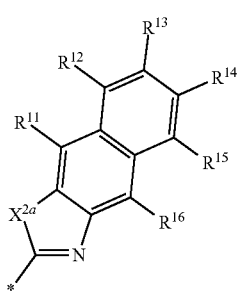
(3)

[Chemical Formula 3B]

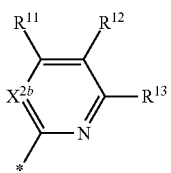
(1)

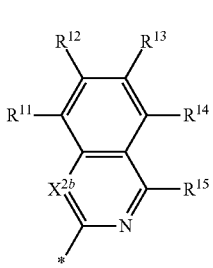
(2)

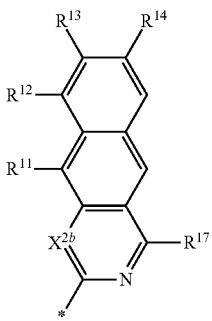
(3)

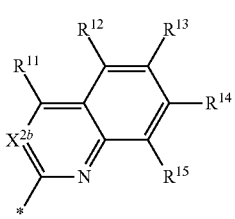
(4)

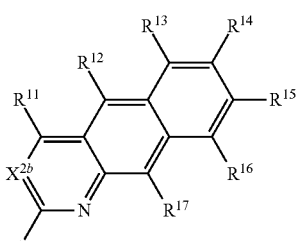
(5)

[Chemical Formula 3C]

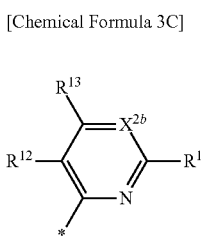
(1)

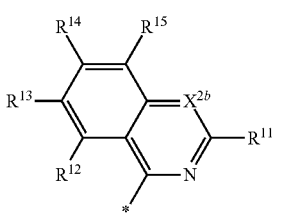
(2)

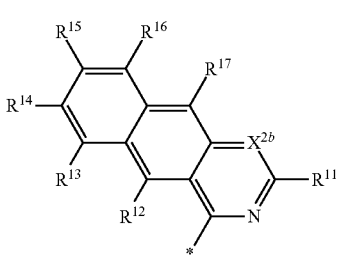
(3)

-continued

[Chemical Formula 3D]

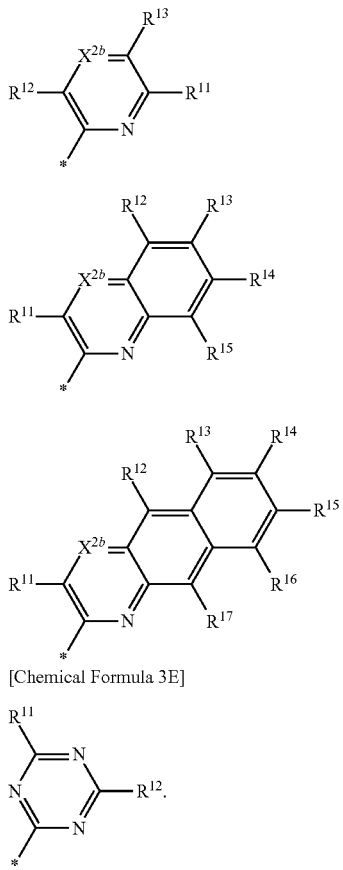

[Chemical Formula 3E]

In Chemical Formula 3A, $X^{2a}$ may be one of S, Se, Te, O, S(=O), S(=O)$_2$, NR$^{a2}$, CR$^{c2}$R$^{d2}$, SiR$^{e2}$R$^{f2}$, or GeR$^{g2}$R$^{h2}$ (wherein, R$^{a2}$, R$^{c2}$, R$^{d2}$, R$^{e2}$, R$^{f2}$, R$^{g2}$, and R$^{h2}$ independently may be one of hydrogen, a substituted C1 to C10 alkyl group, or an unsubstituted C1 to C10 alkyl group).

In Chemical Formula 3B, $X^{2b}$ may be one of N or CR$^{b2}$ (wherein, R$^{b2}$ may be one of hydrogen, a substituted C1 to C10 alkyl group, or an unsubstituted C1 to C10 alkyl group).

In Chemical Formulae 3C and 3D, $X^{2b}$ may be N.

In Chemical Formulae 3A to 3E, R$^{11}$ to R$^{17}$ independently may be one of hydrogen, deuterium, a substituted C1 to C30 alkyl group, an unsubstituted C1 to C30 alkyl group, a substituted C1 to C30 alkoxy group, an unsubstituted C1 to C30 alkoxy group, a substituted C6 to C30 aryl group, an unsubstituted C6 to C30 aryl group, a substituted C3 to C30 heteroaryl group, an unsubstituted C3 to C30 heteroaryl group, a substituted C2 to C30 acyl group, an unsubstituted C2 to C30 acyl group, a halogen, a cyano group (—CN), a cyano-containing group, a nitro group, —SiR$^a$R$^b$R$^c$ (wherein R$^a$, R$^b$, and R$^c$ independently may be one of hydrogen, a substituted C1 to C10 alkyl group, or an unsubstituted C1 to C10 alkyl group), or a combination thereof.

In Chemical Formulae 3A to 3D, R$^{11}$ to R$^{17}$ independently may be present or an adjacent two thereof may be linked with each other to provide a fused ring.

In some example embodiments, in Chemical Formula 2A, at least one of Ar$^1$ and Ar$^2$ may include a heteroatom selected from nitrogen (N), sulfur (S), and selenium (Se). Alternatively, in Chemical Formula 2B, at least one of Ar$^3$ and Ar$^4$ may include a heteroatom selected from nitrogen (N), sulfur (S), and selenium (Se).

In some example embodiments, in Chemical Formula 1, Y may be represented by Chemical Formula 2A-1, Chemical Formula 2A-2, Chemical Formula 2B-1, or Chemical Formula 2B-2:

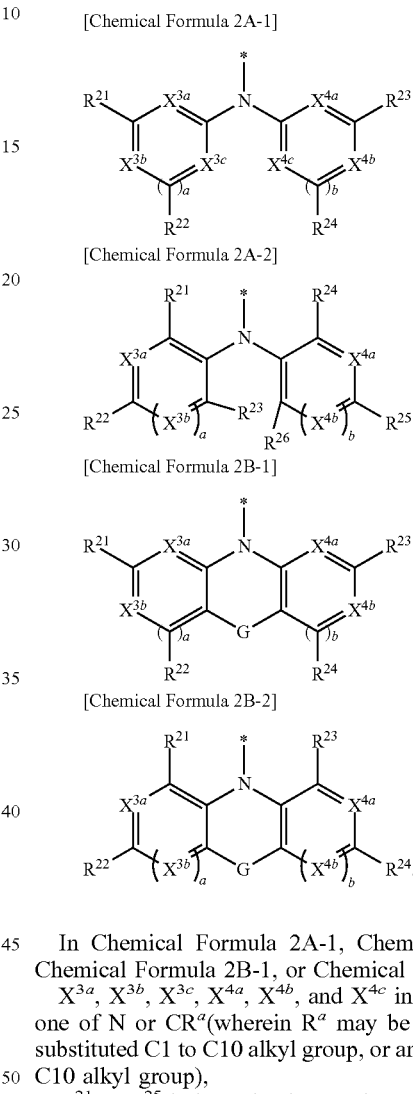

In Chemical Formula 2A-1, Chemical Formula 2A-2, Chemical Formula 2B-1, or Chemical Formula 2B-2, $X^{3a}$, $X^{3b}$, $X^{3c}$, $X^{4a}$, $X^{4b}$, and $X^{4c}$ independently may be one of N or CR$^a$ (wherein R$^a$ may be one of hydrogen, a substituted C1 to C10 alkyl group, or an unsubstituted C1 to C10 alkyl group), R$^{21}$ to R$^{25}$ independently may be one of hydrogen, deuterium, a substituted C1 to C30 alkyl group, an unsubstituted C1 to C30 alkyl group, a substituted C1 to C30 alkoxy group, an unsubstituted C1 to C30 alkoxy group, a substituted C6 to C30 aryl group, an unsubstituted C6 to C30 aryl group, a substituted C3 to C30 heteroaryl group, an unsubstituted C3 to C30 heteroaryl group, a halogen, a cyano group (—CN), a cyano-containing group, or a combination thereof, and a and b independently may be an integer of 0 or 1.

In Chemical Formula 2B-1 and Chemical Formula 2B-2,

G may be one of a single bond, S, Se, Te, O, NR$^{a3}$, (CR$^{b3}$R$^{c3}$)$_n$, (C(R$^{d3}$)=C(R$^{e3}$)), SiR$^{f3}$R$^{g3}$, or GeR$^{h3}$R$^{i3}$ (wherein R$^{a3}$, R$^{b3}$, R$^{c3}$, R$^{d3}$, R$^{e3}$, R$^{f3}$, R$^{g3}$, R$^{h3}$, and R$^{i3}$ independently may be one of hydrogen, a halogen, a substituted C1 to C10 alkyl group, an unsubstituted C1 to C10 alkyl group, a substituted C6 to C10 aryl group, or an unsubstituted C6 to C10 aryl group, and optionally $R^{d3}$ and $R^{e3}$ independently may be present or may be linked with each other to provide a fused ring, and n may be an integer of 1 or 2).

In some example embodiments, an organic photoelectric device, may include the above-referenced compound in an active layer, a first electrode; and a second electrode facing the first electrode. The active layer may be between the first electrode and the second electrode.

In some example embodiments, an image sensor may include the organic photoelectric device and a substrate. The organic photoelectric device may be on the substrate.

The compound selectively absorbs light in a green wavelength region and has excellent deposition stability, heat resistance, and oxidation resistance, and the organic photoelectric device, the image sensor, and the electronic device exhibit improved efficiency by increasing wavelength selectivity in a green wavelength region due to the compound.

DETAILED DESCRIPTION

Figure 1:
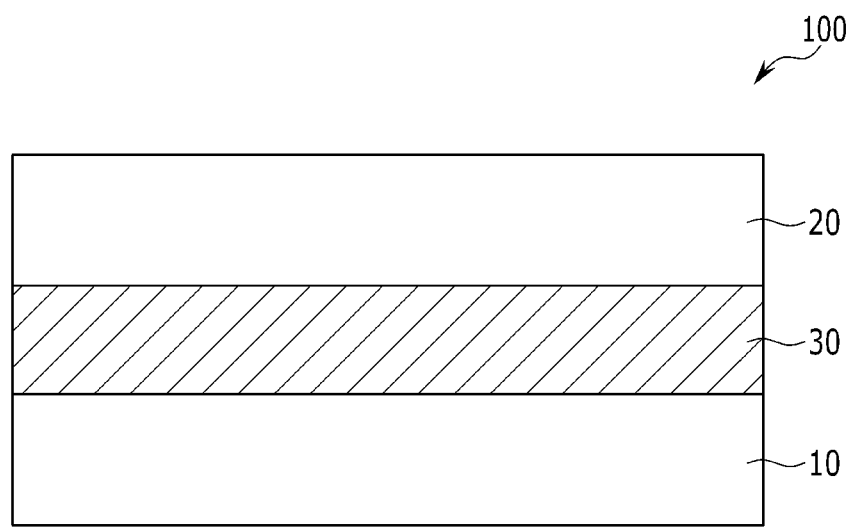
FIG. 1 is a cross-sectional view showing an organic photoelectric device according to an embodiment.

Example embodiments will hereinafter be described in detail, and may be easily performed by a person having an ordinary skill in the related art. However, this disclosure may be embodied in many different forms and is not to be construed as limited to the exemplary embodiments set forth herein.

In the drawings, the thickness of layers, regions, etc., are exaggerated for clarity. Like reference numerals designate like elements throughout the specification. It will be understood that when an element such as a layer, film, region, or plate is referred to as being "on" another element, it can be directly on the other element or intervening elements may also be present. In contrast, when an element is referred to as being "directly on" another element, there are no intervening elements present.

In the drawings, parts having no relationship with the description are omitted for clarity of the embodiments, and the same or similar constituent elements are indicated by the same reference numeral throughout the specification.

As used herein, when specific definition is not otherwise provided, the term "substituted" refers to replacement of a hydrogen valence halogen atom (F, Br, Cl, or I), a hydroxy group, a nitro group, a cyano group, an amino group, an azido group, an amidino group, a hydrazino group, a hydra- zono group, a carbonyl group, a carbamyl group, a thiol group, an ester group, a carboxyl group or a salt thereof, a sulfonic acid group or a salt thereof, phosphoric acid group or a salt thereof, a C1 to C20 alkyl group, a C1 to C20 alkoxy group, a C2 to C20 alkenyl group, a C2 to C20 alkynyl group, a C6 to C30 aryl group, a C7 to C30 arylalkyl group, a C2 to C20 heteroaryl group, a C3 to C20 heteroarylalkyl group, a C3 to C30 cycloalkyl group, a C3 to C15 cycloalkenyl group, a C6 to C15 cycloalkynyl group, a C2 to C20 heterocycloalkyl group, and a combination thereof.

As used herein, when specific definition is not otherwise provided, the term "'hetero" refers to one including 1 to 3 heteroatoms selected from N, O, S, P, and Si.

As used herein, the term "alkyl group" for example refers to a methyl group, an ethyl group, a propyl group, an isopropyl group, an n-butyl group, an isobutyl group, a t-butyl group, a pentyl group, a hexyl group, and the like.

As used herein, the term "cycloalkyl group" for example refers to a cyclopropyl group, a cyclobutyl group, a cyclopentyl group, a cyclohexyl group, and the like.

As used herein, the term "aryl group" refers to a substituent including all element of the cycle having p-orbitals which form conjugation, and may be a monocyclic, polycyclic or fused ring polycyclic (i.e., rings sharing adjacent pairs of carbon atoms) functional group.

As used herein, when a definition is not otherwise provided, the term "cyano-containing group" refers to a monovalent group such as a C1 to C30 alkyl group, a C2 to C30 alkenyl group, or a C2 to C30 alkynyl group where at least one hydrogen is substituted with a cyano group. The cyano-containing group also refers to a divalent group such as a dicyanoalkenyl group represented by $=CR^{x'}-(CR^{x}R^{y})-CR^{y'}(CN)_2$ wherein $R^x$, $R^y$, $R^{x'}$, and $R^{y'}$ are independently hydrogen or a C1 to C10 alkyl group and p is an integer of 0 to 10. Specific examples of the cyano-containing group may be a dicyanomethyl group, a dicyanovinyl group, a cyanoethynyl group, and the like.

As used herein, when a definition is not otherwise provided, the term "combination thereof" refers to at least two substituents bound to each other by a single bond or a C1 to C10 alkylene group, or at least two fused substituents.

Expressions such as "at least one of," when preceding a list of elements (e.g., A, B, and C), modify the entire list of elements and do not modify the individual elements of the list. For example, "at least one of A, B, and C," "at least one of A, B, or C," "one of A, B, C, or a combination thereof," and "one of A, B, C, and a combination thereof," respectively, may be construed as covering any one of the following combinations: A; B; A and B; A and C; B and C; and A, B, and C."

Hereinafter, a compound according to an embodiment is described. The compound is represented by Chemical Formula 1.

[Chemical Formula 1]

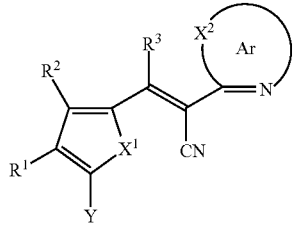

In Chemical Formula 1,

X$^1$ is one of S, Se, Te, O, S(=O), S(=O)$_2$, NR$^{a1}$, SiR$^{b1}$R$^{c1}$, and GeR$^{d1}$R$^{e1}$ (wherein R$^{a1}$, R$^{b1}$, R$^{c1}$, R$^{d1}$, and R$^{e1}$ are independently one of hydrogen and a substituted or unsubstituted C1 to C10 alkyl group), Ar is an aromatic ring group including N and X$^2$ (wherein X$^2$ is one of S, Se, Te, O, S(=O), S(=O)$_2$, N, NR$^{a2}$, CR$^{b2}$, CR$^{c2}$R$^{d2}$, SiR$^{e2}$R$^{f2}$, and GeR$^{g2}$R$^{h2}$, and R$^{a2}$, R$^{b2}$, R$^{c2}$, R$^{d2}$, R$^{e2}$, R$^{f2}$, R$^{g2}$, and R$^{h2}$ are independently one of hydrogen and a substituted or unsubstituted C1 to C10 alkyl group), R$^1$ to R$^3$ are independently one of hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heteroaryl group, a substituted or unsubstituted C2 to C30 acyl group, a halogen, a cyano group (—CN), a cyano-containing group, a nitro group, —SiR$^a$R$^b$R$^c$ (wherein R$^a$, R$^b$, and R$^c$ are independently one of hydrogen and a substituted or unsubstituted C1 to C10 alkyl group), and a combination thereof, and Y is a functional group represented by Chemical Formula 2A or Chemical Formula 2B.

[Chemical Formula 2A]

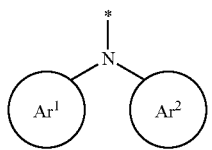

In Chemical Formula 2A,

Ar$^1$ and Ar$^2$ are independently one of a substituted or unsubstituted C6 to C30 aryl group and a substituted or unsubstituted C3 to C30 heteroaryl group.

[Chemical Formula 2B]

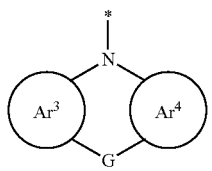

In Chemical Formula 2B,

Ar$^3$ and Ar$^4$ are independently one of a substituted or unsubstituted C6 to C30 arylene group and a substituted or unsubstituted C3 to C30 heteroarylene group, and G is one of a single bond, S, Se, Te, O, NR$^{a3}$, (CR$^{b3}$R$^{c3}$)$_n$, (C(R$^{d3}$)=C(R$^{e3}$)), SiR$^{f3}$R$^{g3}$, and GeR$^{h3}$R$^{i3}$ (wherein R$^{a3}$, R$^{b3}$, R$^{c3}$, R$^{d3}$, R$^{e3}$, R$^{f3}$, R$^{g3}$, R$^{h3}$, and R$^{i3}$ are independently one of hydrogen, a halogen, a substituted or unsubstituted C1 to C10 alkyl group, and a substituted or unsubstituted C6 to C10 aryl group, and optionally R$^{d3}$ and R$^{e3}$ are independently present or are linked with each other to provide a fused ring, and n is an integer of 1 or 2).

The compound represented by Chemical Formula 1 includes an electron donor moiety represented by Y; a linker including an X$^1$-containing 5-membered ring; and unsaturated nitrile and an electron acceptor moiety of an aromatic ring group (Ar) including N and X$^2$.

In Chemical Formula 1, examples of the substituted or unsubstituted C1 to C30 alkyl group may be a haloalkyl group, examples of the substituted or unsubstituted C2 to C30 acyl group may be an acetyl group, and examples of the halogen may be F, Cl, Br, or I.

In Chemical Formula 1, Ar may be represented by one of Chemical Formula 3A to Chemical Formula 3E.

[Chemical Formula 3A]

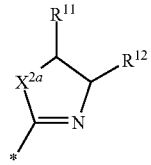

(1)

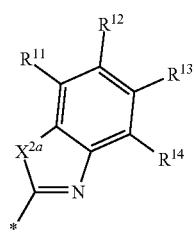

(2)

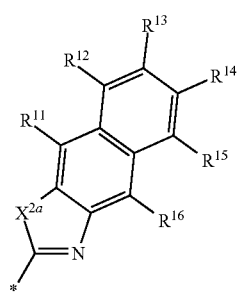

(3)

In Chemical Formula 3A,

X$^{2a}$ is one of S, Se, Te, O, S(=O), S(=O)$_2$, NR$^{a2}$, CR$^{c2}$R$^{d2}$, SiR$^{e2}$R$^{f2}$, and GeR$^{g2}$R$^{h2}$ (wherein, R$^{a2}$, R$^{c2}$, R$^{d2}$, R$^{e2}$, R$^{f2}$, R$^{g2}$, and R$^{h2}$ are independently one of hydrogen and a substituted or unsubstituted C1 to C10 alkyl group), and R$^{11}$ to R$^{16}$ are independently one of hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heteroaryl group, a substituted or unsubstituted C2 to C30 acyl group, a halogen, a cyano group (—CN), a cyano-containing group, a nitro group, —SiR$^a$R$^b$R$^c$ (wherein R$^a$, R$^b$, and R$^c$ are independently one of hydrogen and a substituted or unsubstituted C1 to C10 alkyl group), and a combination thereof, wherein R$^{11}$ to R$^{16}$, R$^{a2}$, R$^{c2}$, R$^{d2}$, R$^{e2}$, R$^{f2}$, R$^{g2}$, and R$^{h2}$ are independently present or an adjacent two thereof are linked with each other to provide a fused ring. The substituted C1 to C30 alkyl group may be a C1 to C30 fluoroalkyl group, for example a C1 to C30 perfluoroalkyl group.

[Chemical Formula 3B]

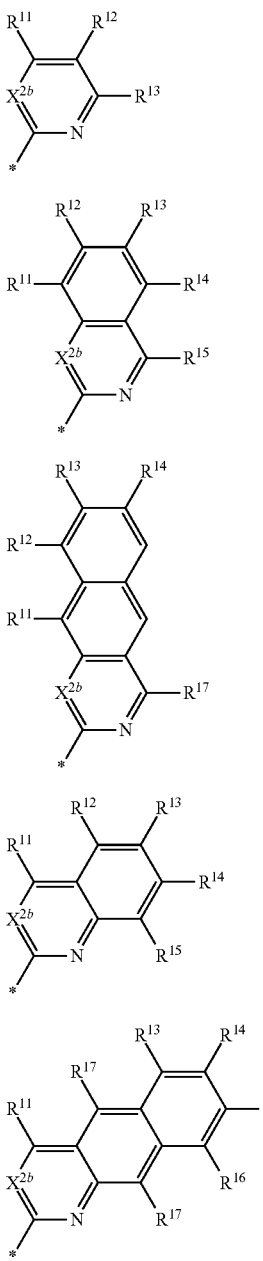

In Chemical Formula 3B, $X^{2b}$ is one of N and $CR^{b2}$ (wherein, $R^{b2}$ is one of hydrogen and a substituted or unsubstituted C1 to C10 alkyl group), and $R^{11}$ to $R^{17}$ are independently one of hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heteroaryl group, a substituted or unsubstituted C2 to C30 acyl group, a halogen, a cyano group (—CN), a cyano-containing group, a nitro group, —SiR$^a$R$^b$R$^c$ (wherein R$^a$, R$^b$, and R$^c$ are independently one of hydrogen and a substituted or unsubstituted C1 to C10 alkyl group), and a combination thereof, wherein $R^{11}$ to $R^{17}$ and $R^{b2}$ are independently present or an adjacent two thereof are linked with each other to provide a fused ring. The substituted C1 to C30 alkyl group may be a C1 to C30 fluoroalkyl group, for example a C1 to C30 perfluoroalkyl group.

[Chemical Formula 3C]

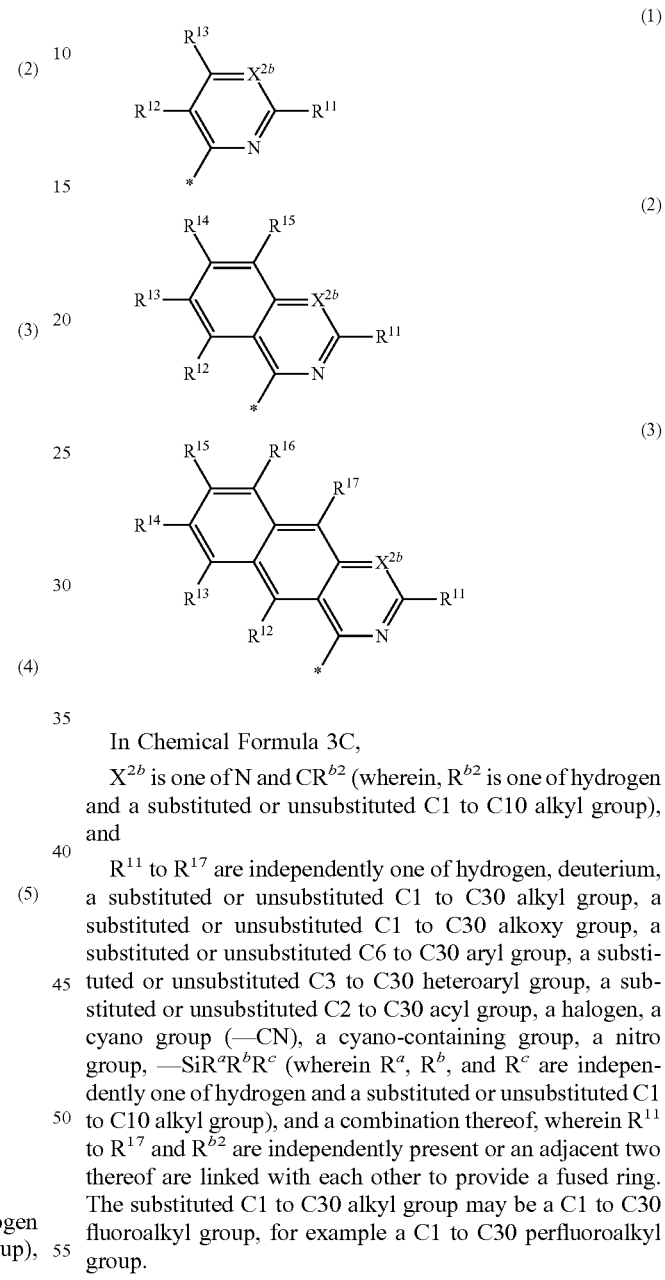

In Chemical Formula 3C, $X^{2b}$ is one of N and $CR^{b2}$ (wherein, $R^{b2}$ is one of hydrogen and a substituted or unsubstituted C1 to C10 alkyl group), and $R^{11}$ to $R^{17}$ are independently one of hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heteroaryl group, a substituted or unsubstituted C2 to C30 acyl group, a halogen, a cyano group (—CN), a cyano-containing group, a nitro group, —SiR$^a$R$^b$R$^c$ (wherein R$^a$, R$^b$, and R$^c$ are independently one of hydrogen and a substituted or unsubstituted C1 to C10 alkyl group), and a combination thereof, wherein $R^{11}$ to $R^{17}$ and $R^{b2}$ are independently present or an adjacent two thereof are linked with each other to provide a fused ring. The substituted C1 to C30 alkyl group may be a C1 to C30 fluoroalkyl group, for example a C1 to C30 perfluoroalkyl group.

[Chemical Formula 3D]

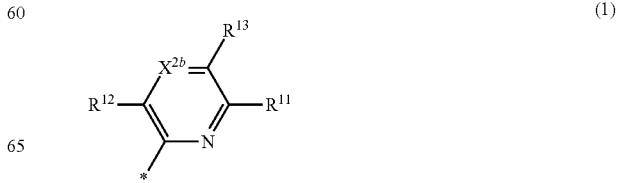

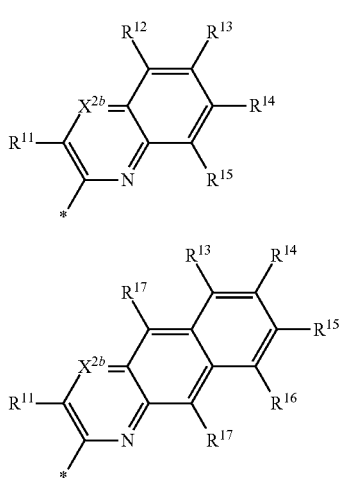

In Chemical Formula 3D, $X^{2b}$ is one of N and $CR^{b2}$ (wherein, $R^{b2}$ is one of hydrogen and a substituted or unsubstituted C1 to C10 alkyl group), and $R^{11}$ to $R^{17}$ are independently one of hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heteroaryl group, a substituted or unsubstituted C2 to C30 acyl group, a halogen, a cyano group (—CN), a cyano-containing group, a nitro group, —$SiR^aR^bR^c$ (wherein $R^a$, $R^b$, and $R^c$ are independently one of hydrogen and a substituted or unsubstituted C1 to C10 alkyl group), and a combination thereof, wherein $R^{11}$ to $R^{17}$ and $R^{b2}$ are independently present or an adjacent two thereof are linked with each other to provide a fused ring. The substituted C1 to C30 alkyl group may be a C1 to C30 fluoroalkyl group, for example a C1 to C30 perfluoroalkyl group.

[Chemical Formula 3E]

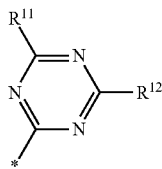

In Chemical Formula 3E, $R^{11}$ and $R^{12}$ are independently one of hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heteroaryl group, a substituted or unsubstituted C2 to C30 acyl group, a halogen, a cyano group (—CN), a cyano-containing group, a nitro group, —$SiR^aR^bR^c$ (wherein $R^a$, $R^b$, and $R^c$ are independently one of hydrogen and a substituted or unsubstituted C1 to C10 alkyl group), and a combination thereof. The substituted C1 to C30 alkyl group may be a C1 to C30 fluoroalkyl group, for example a C1 to C30 perfluoroalkyl group.

In Chemical Formulae 3A to 3E, a fused ring is formed by combining a ring formed by linking adjacent two groups among $R^{11}$ to $R^{16}$, $R^{a2}$, $R^{c2}$, $R^{d2}$, $R^{e2}$, $R^{f2}$, $R^{g2}$ and $R^{h2}$ of Chemical Formula 3A or a ring formed by linking adjacent two groups among $R^{11}$ to $R^{17}$ and $R^{b2}$ of Chemical Formulae 3B to 3D, with an aromatic ring of Chemical Formulae 3A to 3E and may include two or more 5-membered or 6-membered ring groups or a non-aromatic 5-membered or 6-membered ring group.

The ring formed by linking adjacent two groups among $R^{11}$ to $R^{16}$, $R^{a2}$, $R^{c2}$, $R^{d2}$, $R^{e2}$, $R^{f2}$, $R^{g2}$, and $R^{h2}$ in Chemical Formula 3A may be at least two, and in addition, the ring formed by linking adjacent two groups among $R^{11}$ to $R^{17}$ and $R^{b2}$ in Chemical Formulae 3B to 3D may be at least two.

In addition, the fused ring may include a heteroatom, and the heteroatom may be selected from nitrogen (N), sulfur (S), selenium (Se), tellurium (Te), oxygen (O), germanium (Ge), and silicon (Si).

In Chemical Formula 2A, at least one of $Ar^1$ and $Ar^2$ may include a heteroatom selected from nitrogen (N), sulfur (S), and selenium (Se).

$Ar^1$ and $Ar^2$ may be a substituted or unsubstituted C6 to C30 aryl group or a substituted or unsubstituted C3 to C30 heteroaryl group, for example a substituted or unsubstituted C6 to C20 aryl group or a substituted or unsubstituted C3 to C20 heteroaryl group.

In example embodiments, the aryl group may be selected from a phenyl group, a naphthyl group, and an anthracenyl group and the heteroaryl group may be selected from a pyrrolyl group, a prazolyl group, an imidazolyl group, an oxazolyl group, an isoxazolyl group, a thiazolyl group, an isothiazolyl group, a pyridinyl group, a pyridazinyl group, a pyrimidinyl group, a pyrazinyl group, an indolyl group, a quinolinyl group, an isoquinolinyl group, an naphthyridinyl group, a cinnolinyl group, a quinazolinyl group, a phthalazinyl group, a benzotriazinyl group, a pyridopyrazinyl group, a pyridopyrimidinyl group, a pyridopyridazinyl group, a thienyl group, a benzothienyl group, a selenophenyl group, and a benzoselenophenyl group.

In Chemical Formula 2B, at least one of $Ar^3$ and $Ar^4$ may include a heteroatom selected from nitrogen (N), sulfur (S), and selenium (Se).

$Ar^3$ and $Ar^4$ may be a substituted or unsubstituted C6 to C30 arylene group or a substituted or unsubstituted C3 to C30 heteroarylene group, for example a substituted or unsubstituted C6 to C20 arylene group or a substituted or unsubstituted C3 to C20 heteroarylene group.

In example embodiments, the arylene group may be selected from a phenylene group, a naphthalene group, and an anthracene group and the arylene group may be selected from a pyrrolylene group, a prazolylene group, an imidazolylene group, an oxazolylene group, an isoxazolylene group, a thiazolylene group, an isothiazolylene group, a pyridinylene group, a pyridazinylene group, a pyrimidinylene group, a pyrazinylene group, an indolylene group, a quinolinylene group, an isoquinolinylene group, a naphthyridinylene group, a cinnolinylene group, a quinazolinylene group, a phthalazinylene group, a benzotriazinylene group, a pyridopyrazinylene group, a pyridopyrimidinylene group, a pyridopyridazinylene group, a thienylene group, a benzothienylene group, a selenophenylene group, and a benzoselenophenylene group.

In Chemical Formula 1, Y may be a functional group represented by Chemical Formula 2A-1, Chemical Formula 2A-2, Chemical Formula 2B-1, or Chemical Formula 2B-2.

[Chemical Formula 2A-1]

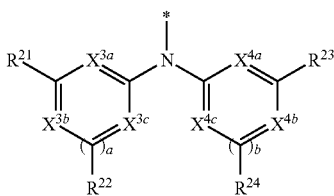

In Chemical Formula 2A-1, $X^{3a}$, $X^{3b}$, $X^{3c}$, $X^{4a}$, $X^{4b}$, and $X^{4c}$ are independently one of N and $CR^a$ (wherein $R^a$ is one of hydrogen and a substituted or unsubstituted C1 to C10 alkyl group), $R^{21}$, $R^{22}$, $R^{23}$, and $R^{24}$ are independently one of hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heteroaryl group, a halogen, a cyano group (—CN), a cyano-containing group, and a combination thereof, and a and b are independently an integer of 0 or 1.

[Chemical Formula 2A-2]

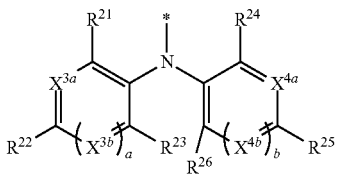

In Chemical Formula 2A-2, $X^{3a}$, $X^{3b}$, $X^{4a}$, and $X^{4b}$ are independently one of N and $CR^a$ (wherein $R^a$ is one of hydrogen and a substituted or unsubstituted C1 to C10 alkyl group), $R^{21}$, $R^{22}$, $R^{23}$, $R^{24}$, $R^{25}$, and $R^{26}$ are independently one of hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heteroaryl group, a halogen, a cyano group (—CN), a cyano-containing group, and a combination thereof, and a and b are independently an integer of 0 or 1.

[Chemical Formula 2B-1]

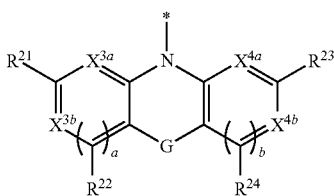

In Chemical Formula 2B-1, $X^{3a}$, $X^{3b}$, $X^{4a}$, and $X^{4b}$ are independently one of N and $CR^a$ (wherein $R^a$ is one of hydrogen and a substituted or unsubstituted C1 to C10 alkyl group), $R^{21}$, $R^{22}$, $R^{23}$, and $R^{24}$ are independently one of hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heteroaryl group, a halogen, a cyano group (—CN), a cyano-containing group, and a combination thereof, a and b are independently an integer of 0 or 1, and G is one of a single bond, S, Se, Te, O, $NR^{a3}$, $(CR^{b3}R^{c3})_n$, $(C(R^{d3})=C(R^{e3}))$, $SiR^{f3}R^{g3}$, and $GeR^{h3}R^{i3}$ (wherein $R^{a3}$, $R^{b3}$, $R^{c3}$, $R^{d3}$, $R^{e3}$, $R^{f3}$, $R^{g3}$, $R^{h3}$, and $R^{i3}$ are independently one of hydrogen, a halogen, a substituted or unsubstituted C1 to C10 alkyl group, and a substituted or unsubstituted C6 to C10 aryl group, and optionally $R^{d3}$ and $R^{e3}$ are independently present or are linked with each other to provide a fused ring, and n is an integer of 1 or 2).

[Chemical Formula 2B-2]

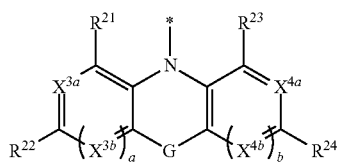

In Chemical Formula 2B-2, $X^{3a}$, $X^{3b}$, $X^{4a}$, and $X^{4b}$ are independently one of N and $CR^a$ (wherein $R^a$ is one of hydrogen and a substituted or unsubstituted C1 to C10 alkyl group), $R^{21}$, $R^{22}$, $R^{23}$, and $R^{24}$ are independently one of hydrogen, deuterium, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heteroaryl group, a halogen, a cyano group (—CN), a cyano-containing group, and a combination thereof, a and b are independently an integer of 0 or 1, and G is one of a single bond, S, Se, Te, O, $NR^{a3}$, $(CR^{b3}R^{c3})_n$, $(C(R^{d3})=C(R^{e3}))$, $SiR^{f3}R^{g3}$, and $GeR^{h3}R^{i3}$ (wherein $R^{a3}$, $R^{b3}$, $R^{c3}$, $R^{d3}$, $R^{e3}$, $R^{f3}$, $R^{g3}$, $R^{h3}$, and $R^{i3}$ are independently one of hydrogen, a halogen, a substituted or unsubstituted C1 to C10 alkyl group, and a substituted or unsubstituted C6 to C10 aryl group, and optionally $R^{d3}$ and $R^{e3}$ are independently present or are linked with each other to provide a fused ring, and n is an integer of 1 or 2).

Examples of the compound represented by Chemical Formula 1 may be compounds represented by Chemical Formula 4-1, but are not limited thereto.

[Chemical Formula 4-1]

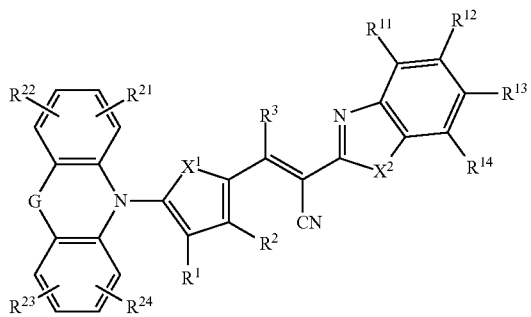

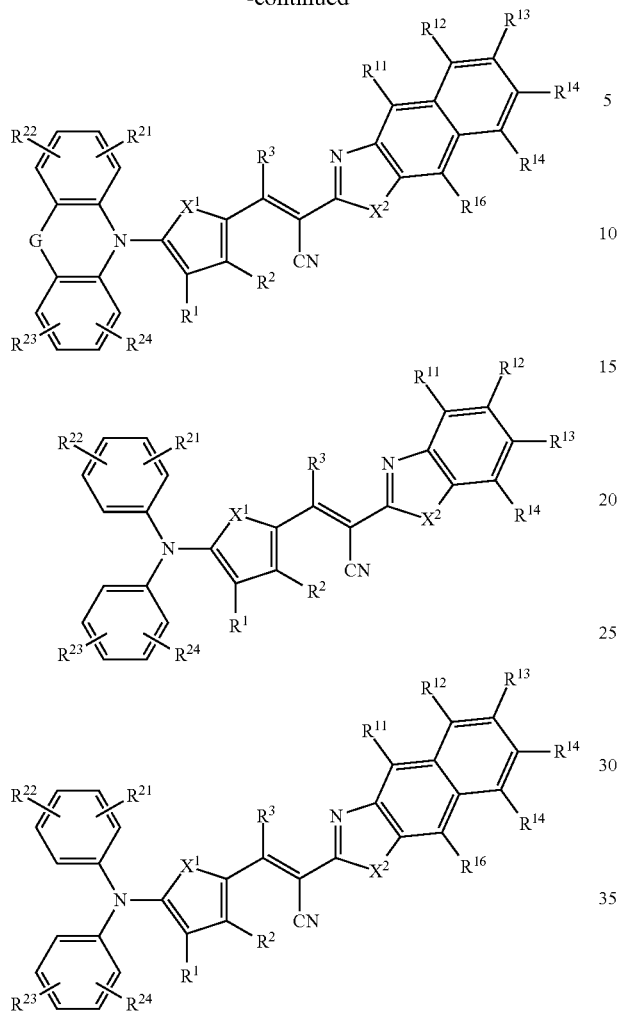
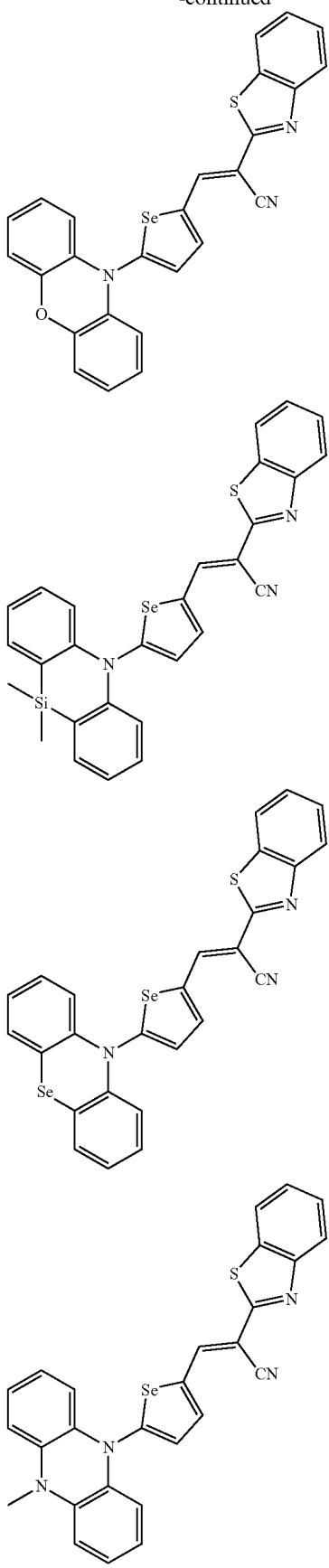
In Chemical Formula 4-1, $X^1$, $X^2$, $R^1$ to $R^3$, $R^{11}$ to $R^{16}$, and $R^{21}$ to $R^{24}$ are the same as described above.
Examples of the compound represented by Chemical Formula 1 may be compounds represented by Chemical Formula 4-1A or Chemical Formula 4-2A, but is not limited thereto.
[Chemical Formula 4-1A]
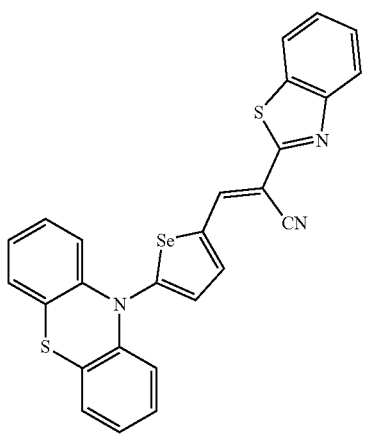

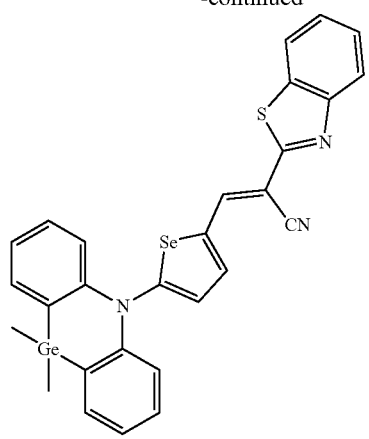
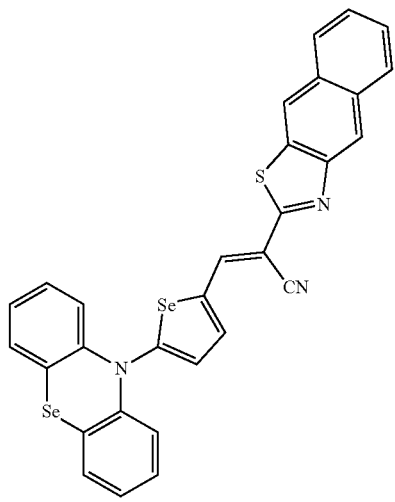
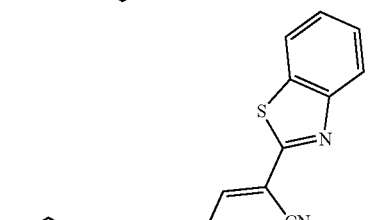
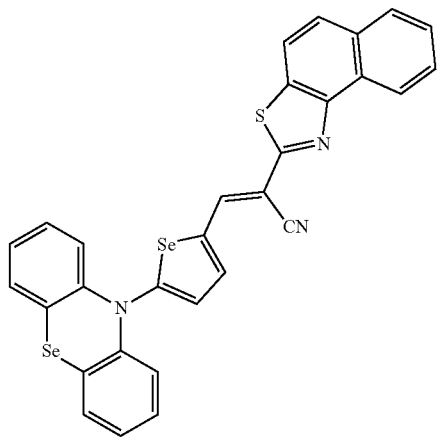
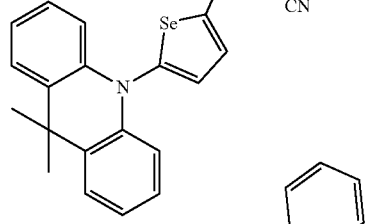
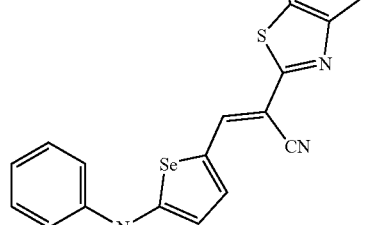
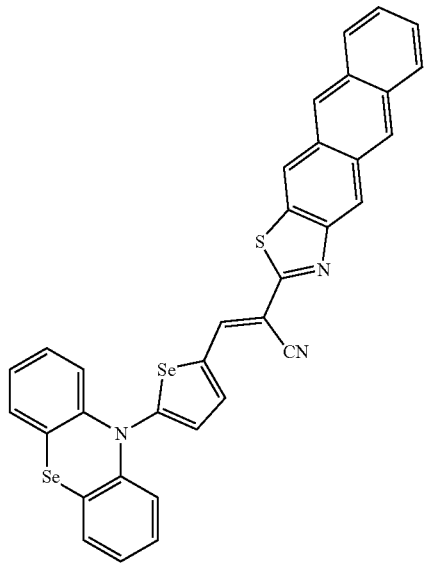
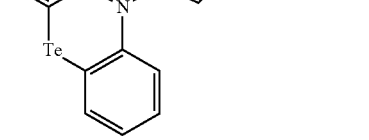

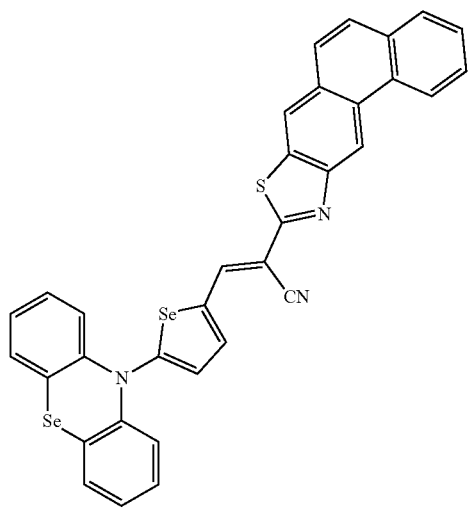
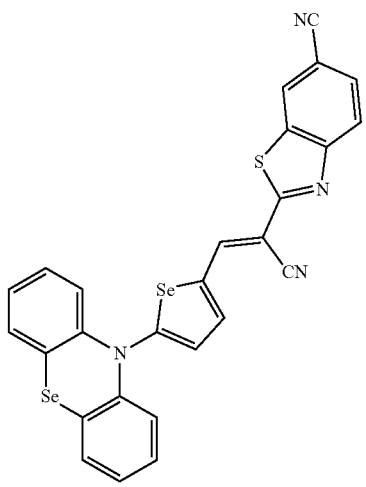
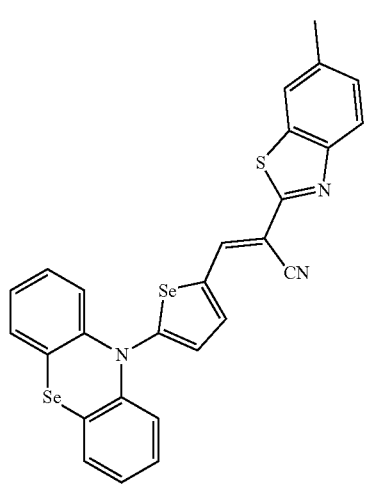
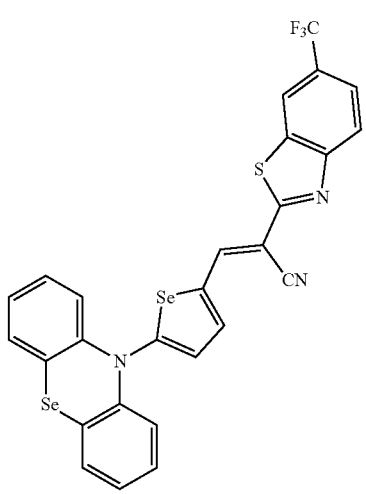
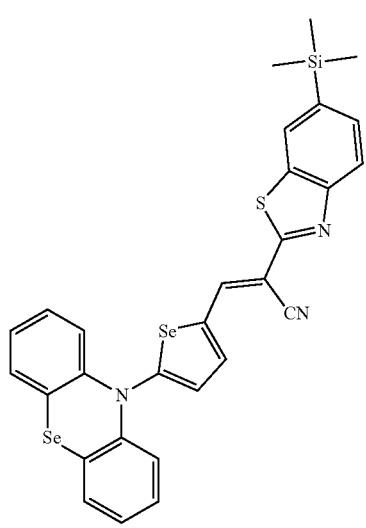
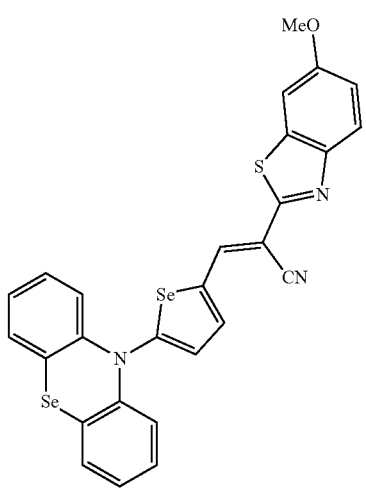

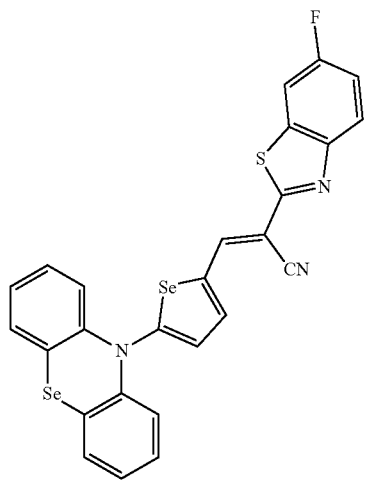
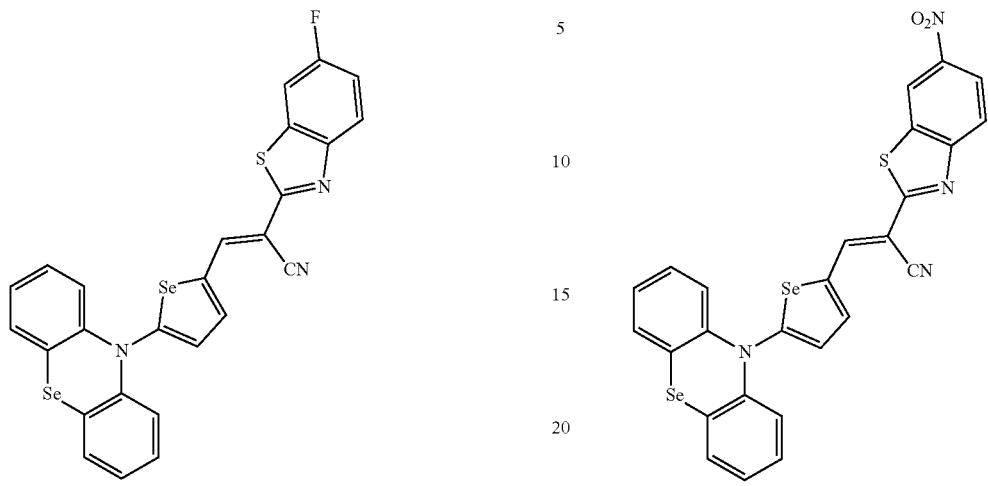
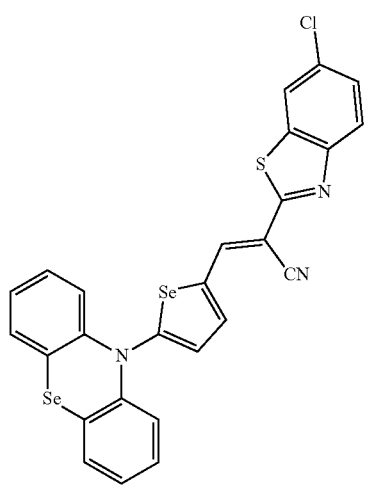
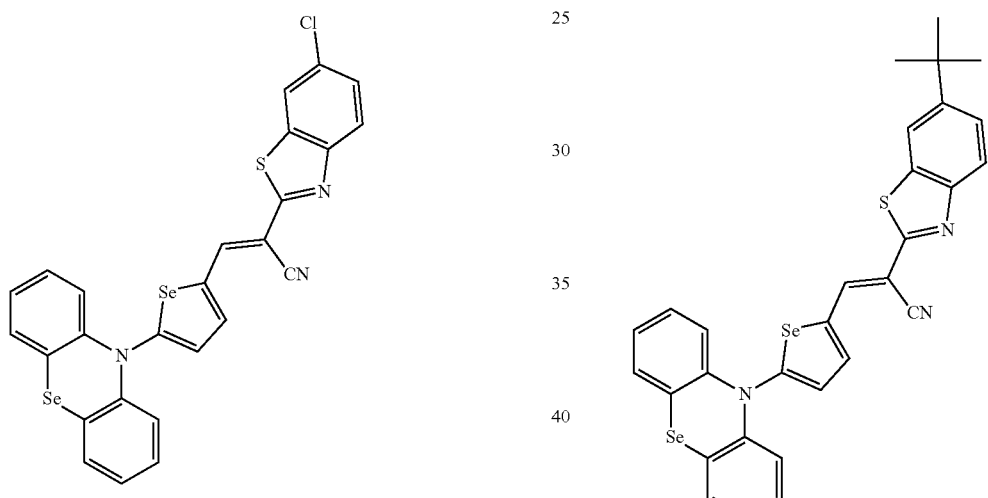
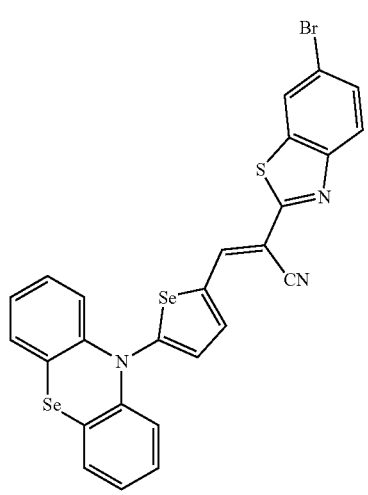
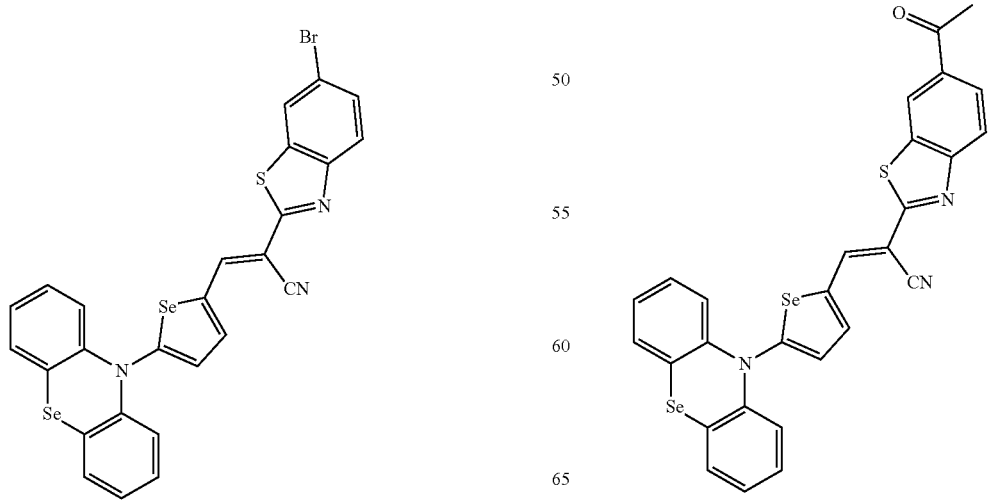

33
-continued
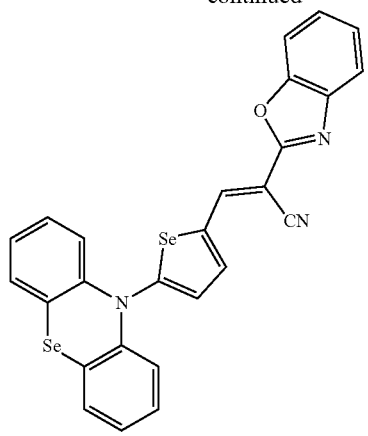
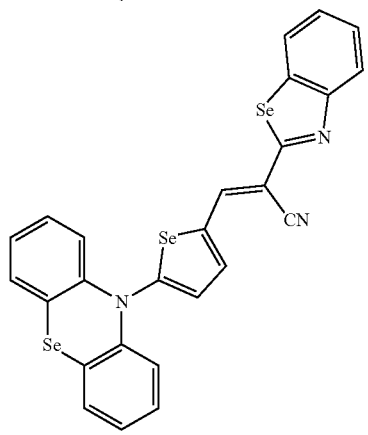
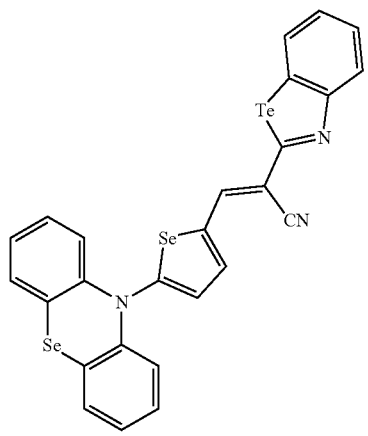 [SMILES: N#C/C(=C\c1ccc(N2c3ccccc3[Se]c3ccccc32)[se]1)C1=NC2=CCC=CC2=N1]
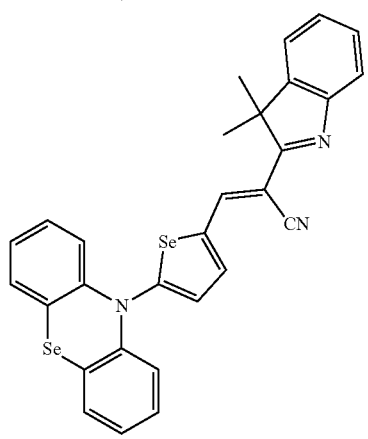
34
-continued
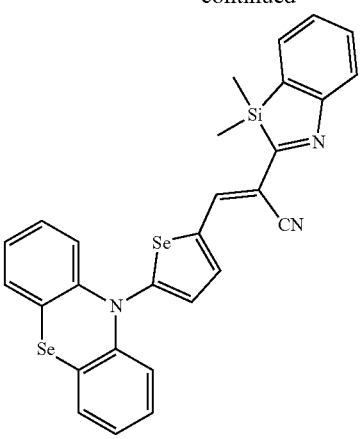
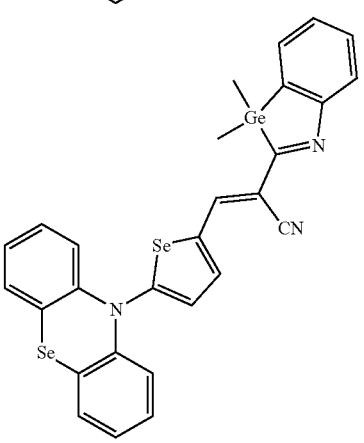
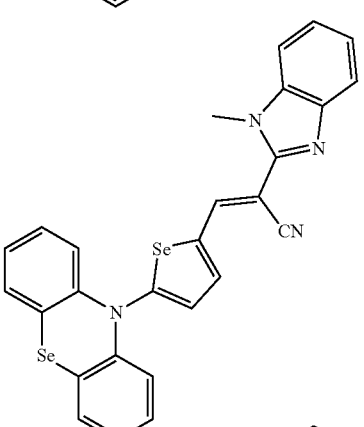
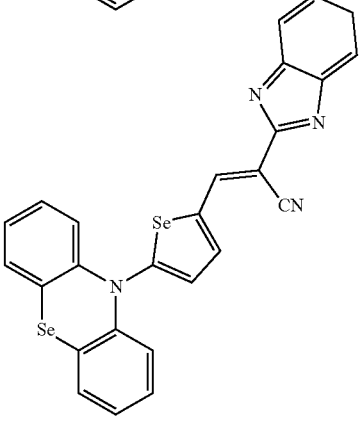

In Chemical Formula 4-1A, hydrogen of each aromatic ring may be replaced by a substituent selected from a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heteroaryl group, a halogen (F, Cl, Br or I), a cyano group (—CN), a cyano-containing group, and a combination thereof.

[Chemical Formula 4-2A]

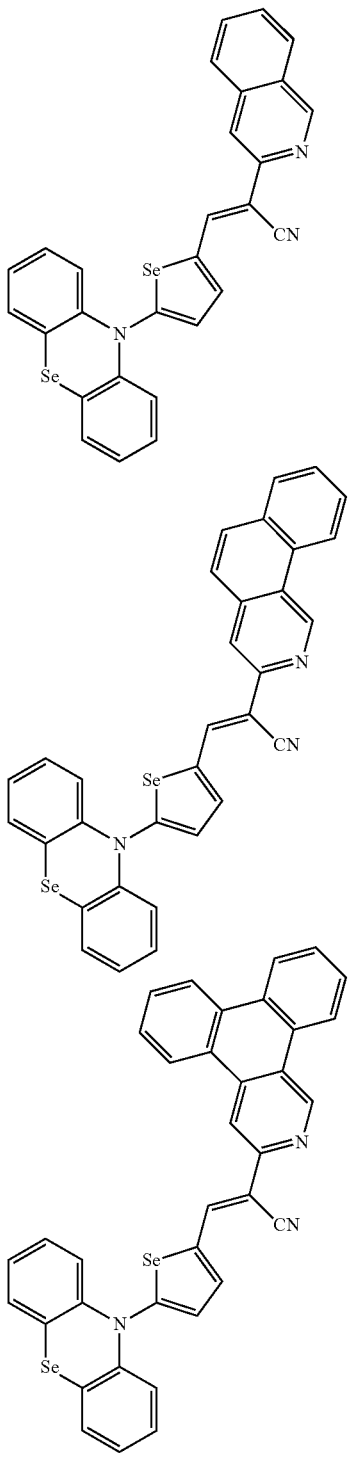

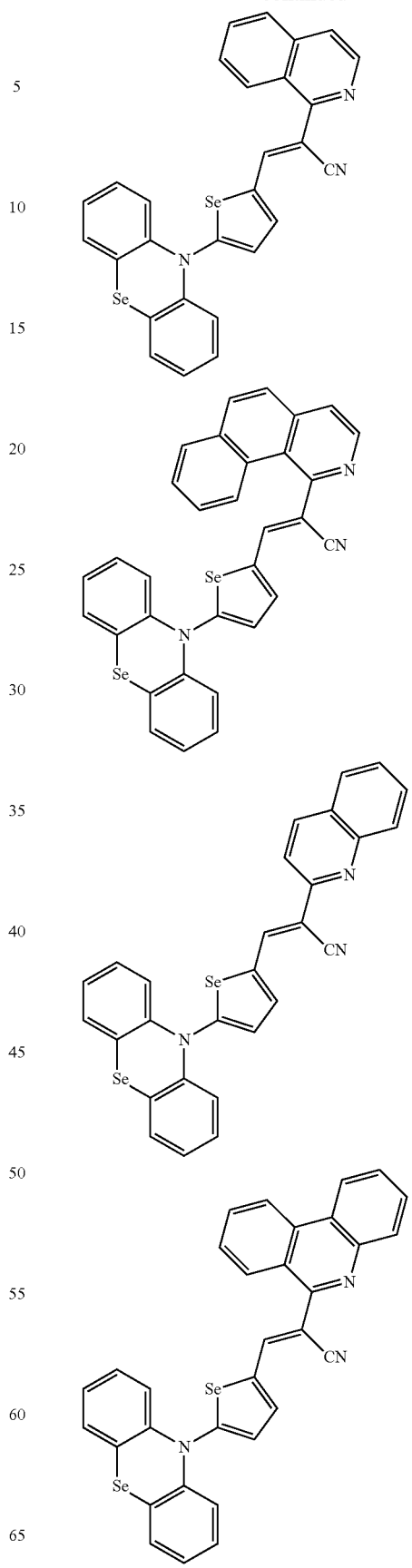

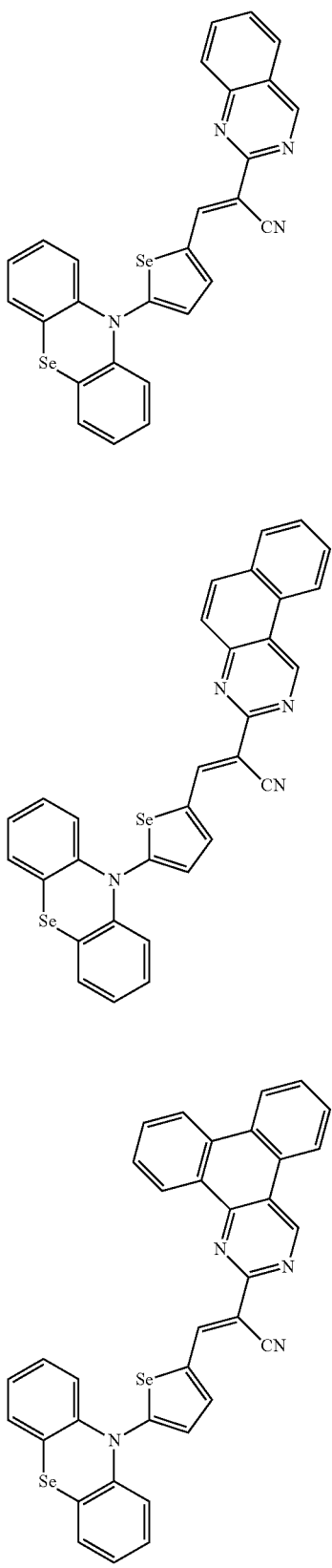

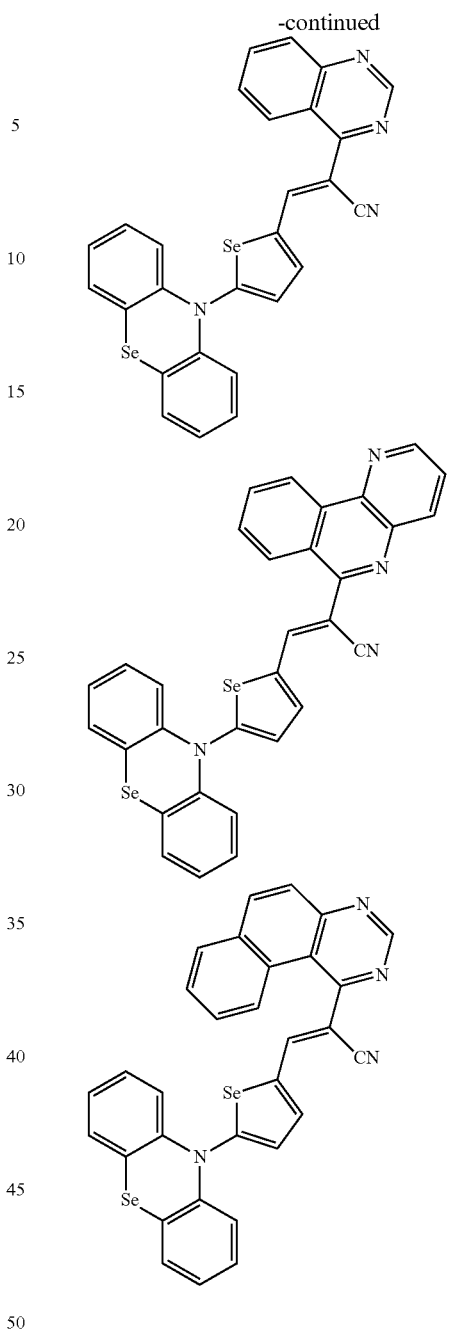

In Chemical Formula 4-2A, hydrogen of each aromatic ring may be replaced by a substituent selected from a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heteroaryl group, a halogen (F, Cl, Br or I), a cyano group (—CN), a cyano-containing group, and a combination thereof.

The compound may be a compound selectively absorbing light in a green wavelength region, and may have a maximum absorption wavelength ($\lambda_{max}$) in a wavelength region of greater than or equal to about 500 nm, for example greater than or equal to about 505 nm, greater than or equal to about 510 nm, greater than or equal to about 515 nm, or greater than or equal to about 520 nm. In addition, the compound may have a maximum absorption wavelength ($\lambda_{max}$) in a wavelength region of less than or equal to about 560 nm, for example less than or equal to about 555 nm, less than or equal to about 550 nm, less than or equal to about 545 nm, or less than or equal to about 540 nm.

The compound may exhibit a light absorption curve having a full width at half maximum (FWHM) of greater than or equal to about 50 nm and less than or equal to about 120 nm, for example less than or equal to about 110 nm in a thin film state. Herein, the FWHM is a width of a wavelength corresponding to half of a maximum absorption point. As used herein, when specific definition is not otherwise provided, it may be defined by absorbance measured by UV-Vis spectroscopy. When the full width at half maximum (FWHM) is within the range, selectivity in a green wavelength region may be increased. The thin film may be a thin film deposited under a vacuum condition.

The compound may be formed into a thin film by using a deposition method. The deposition method may provide a uniform thin film and have small inclusion possibility of impurities into the thin film, but when the compound has a lower melting point than a temperature for the deposition, a product decomposed from the compound may be deposited and thus performance of a device may be deteriorated. Accordingly, the compound desirably has a higher melting point than the deposition temperature. The compound may have greater than or equal to about 3° C., for example greater than or equal to about 10° C. a higher melting point than the deposition temperature and thus may be desirably used for the deposition.

Specifically, a donor/acceptor-type material represented by Chemical Formula 1 may be thermally decomposed at its melting point (Tm). Accordingly, when the material has a lower Tm than a sublimation temperature (Ts) at which the material is vacuum-deposited to form a film, the material may be decomposed before being sublimated (deposited) and not be used to manufacture a device. Since this material is not be appropriate for manufacturing a stable image sensor, Tm should be higher than Ts, and desirably, Tm−Ts≥3° C.

In addition, a temperature (deposition temperature) at which 10 wt % of an initial weight of the compound is lost may be greater than or equal to about 230° C., for example greater than or equal to about 240° C.

The compound has improved deposition stability and heat resistance by including a —CN group (unsaturated nitrile) and a —C=N— group of an aromatic ring group (Ar), and thus purity of a thin film therefrom after continuous deposition is improved and performance of a device is not decreased in accordance with a deposition number.

In addition, a micro lens array (MLA) needs to be formed to concentrate light after manufacturing an organic photoelectric device during manufacture of an image sensor. This micro lens array requires a relatively high temperature (about 160° C.), and this heat treatment may deteriorate performance of the organic photoelectric device. The performance deterioration of the organic photoelectric device during the heat treatment of MLA may be caused not by chemical decomposition of an organic material but its morphology change. The morphology change is in general caused, when a material starts a thermal agitation due to a heat treatment, but even a material having a firm molecule structure may not have the thermal agitation and be prevented from the deterioration by the heat treatment. The compound may have improved heat-resistance due to the —CN group (unsaturated nitrile) and the —C=N— group of an aromatic ring group (Ar) in a donor region, and may be stably maintained during the MLA heat treatment securing process stability.

Since the compound works as a p-type semiconductor, the compound may be appropriately used, as long as it has a higher LUMO level than an n-type semiconductor. For example, when the compound is mixed with an n-type material such as fullerene, the compound desirably has a higher LUMO level than 4.2 eV than the fullerene having a LUMO level of 4.2 eV. As for the appropriate HOMO-LUMO level of the compound, when the compound has a HOMO level ranging from about 5.0 eV to about 5.8 eV and an energy bandgap ranging from about 1.9 eV to about 2.3 eV, the LUMO level of the compound is in a range of about 3.9 eV to about 2.7 eV. The compound having a HOMO level, an LUMO level, and an energy bandgap within the ranges may be used as a p-type semiconductor compound effectively absorbing light in a green wavelength region, and thus has high external quantum efficiency (EQE) and resultantly improves photoelectric conversion efficiency.

In example embodiments, in view of a thin film formation, a compound that may be deposited in a stable process is desirable and thus the compound has a molecular weight of about 300 to about 1500. However, even though the compound has a molecular weight out of the range, a depositable compound may be used without limitation. In addition, when the compound is formed to form a thin film using a coating process, a compound that is dissolved in a solvent and coated may be used without limitation.

The compound may be a p-type semiconductor compound.

Hereinafter, an organic photoelectric device including the compound according to an example embodiment is described with reference to drawings.

FIG. 1 is a cross-sectional view showing an organic photoelectric device according to an example embodiment.

Referring to FIG. 1, an organic photoelectric device 100 according to an example embodiment includes a first electrode 10 and a second electrode 20, and an active layer 30 between the first electrode 10 and the second electrode 20.

One of the first electrode 10 and the second electrode 20 is an anode and the other is a cathode. At least one of the first electrode 10 and the second electrode 20 may be a light-transmitting electrode, and the light-transmitting electrode may be made of, for example, a transparent conductor such as indium tin oxide (ITO) or indium zinc oxide (IZO), or a metal thin layer of a thin single layer or multilayer. When one of the first electrode 10 and the second electrode 20 is a non-light-transmitting electrode, it may be made of, for example, an opaque conductor such as aluminum (Al).

The active layer 30 includes a p-type semiconductor and an n-type semiconductor to form a pn junction, and absorbs external light to generate excitons and then separates the generated excitons into holes and electrons.

The active layer 30 includes the compound represented by Chemical Formula 1. The compound may act as a p-type semiconductor compound in the active layer 30.

The compound is a compound selectively absorbing light in a green wavelength region, and the active layer 30 including the compound may have a maximum absorption wavelength ($\lambda_{max}$) in a wavelength region of greater than or equal to about 500 nm, for example greater than or equal to about 505 nm, greater than or equal to about 510 nm, greater than or equal to about 515 nm, or greater than or equal to about 520 nm and less than or equal to about 560 nm, for example less than or equal to about 555 nm, less than or equal to about 550 nm, less than or equal to about 545 nm, or less than or equal to about 540 nm.

The active layer 30 may exhibit a light absorption curve having a relatively narrow full width at half maximum (FWHM) of about 50 nm to about 120 nm, for example about 50 nm to about 110 nm. Accordingly, the active layer 30 has high selectivity for light in a green wavelength region.

The active layer may have an absorption coefficient of greater than or equal to about $5.5 \times 10^4$ cm$^{-1}$, for example about $5.8 \times 10^4$ cm$^{-1}$ to about $10 \times 10^4$ cm$^{-1}$ or about $7.0 \times 10^4$ cm$^{-1}$ to about $10 \times 10^4$ cm$^{-1}$ when including the compound Chemical Formula 1 and C60 in a volume ratio of about 0.9:1 to about 1.1:1, for example about 1:1.

The active layer 30 may further include an n-type semiconductor compound for forming a pn junction.

The n-type semiconductor compound may be sub-phthalocyanine or a sub-phthalocyanine derivative, fullerene or a fullerene derivative, thiophene or a thiophene derivative, or a combination thereof.

The fullerene may include C60, C70, C76, C78, C80, C82, C84, C90, C96, C240, C540, a mixture thereof, a fullerene nanotube, and the like. The fullerene derivative may refer to compounds of these fullerenes having a substituent attached thereto. The fullerene derivative may include a substituent such as alkyl group, aryl group, or a heterocyclic group. Examples of the aryl groups and heterocyclic groups may be are a benzene ring, a naphthalene ring, an anthracene ring, a phenanthrene ring, a fluorene ring, a triphenylene ring, a naphthacene ring, a biphenyl ring, a pyrrole ring, a furan ring, a thiophene ring, an imidazole ring, an oxazole ring, a thiazole ring, a pyridine ring, a pyrazine ring, a pyrimidine ring, a pyridazine ring, an indolizine ring, an indole ring, a benzofuran ring, a benzothiophene ring, an isobenzofuran ring, a benzimidazole ring, an imidazopyridine ring, a quinolizidine ring, a quinoline ring, a phthalazine ring, a naphthyridine ring, a quinoxaline ring, a quinoxazoline ring, an isoquinoline ring, a carbazole ring, a phenanthridine ring, an acridine ring, a phenanthroline ring, a thianthrene ring, a chromene ring, an xanthene ring, a phenoxathin ring, a phenothiazine ring, or a phenazine ring.

The sub-phthalocyanine or the sub-phthalocyanine derivative may be represented by Chemical Formula 5.

[Chemical Formula 5]

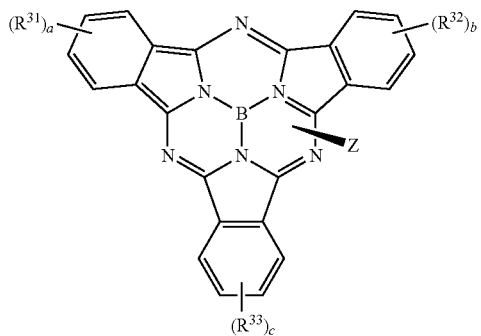

In Chemical Formula 5, $R^{31}$ to $R^{33}$ are independently one of hydrogen, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heteroaryl group, a substituted or unsubstituted C2 to C30 acyl group, a halogen, a halogen-containing group, and a combination thereof, a, b, and c are integers ranging from 1 to 3, and Z is a monovalent substituent.

For example, Z may be a halogen or a halogen-containing group, for example F, Cl, an F-containing group, or a C1-containing group.

The halogen refers to F, Cl, Br, or I and the halogen-containing group refers to alkyl group where at least one of hydrogen is replaced by F, Cl, Br, or I.

The thiophene derivative may be for example represented by 6 or Chemical Formula 7, but is not limited thereto.

[Chemical Formula 6]

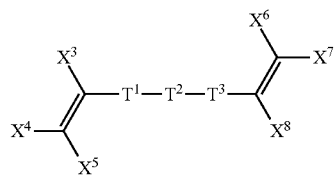

EWG$^1$-T$^1$-T$^2$-T$^3$-EWG$^2$  [Chemical Formula 7]

In Chemical Formulae 6 and 7,

T$^1$, T$^2$, and T$^3$ are aromatic rings including substituted or unsubstituted thiophene moieties, T$^1$, T$^2$, and T$^3$ are independently present or are fused to each other, X$^3$ to X$^8$ are independently hydrogen, a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heterocyclic group, a cyano group, or a combination thereof, and EWG$^1$ and EWG$^2$ are independently electron withdrawing groups.

For example, in Chemical Formula 6, at least one of X$^3$ to X$^8$ may be an electron withdrawing group, for example a cyano-containing group.

The active layer 30 may further include a second p-type semiconductor compound selectively absorbing green light. The p-type semiconductor compound may be a compound represented by Chemical Formula 8.

[Chemical Formula 8]

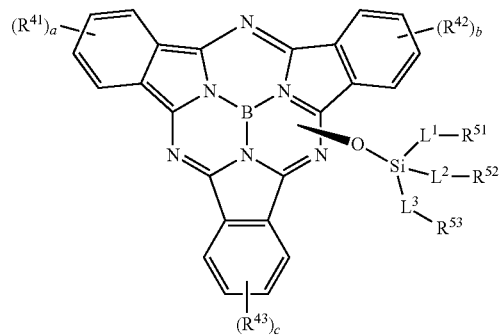

In Chemical Formula 8, $R^{41}$ to $R^{43}$ are independently selected from hydrogen, a substituted or unsubstituted C1 to C30 aliphatic hydrocarbon group, a substituted or unsubstituted C6 to C30 aromatic hydrocarbon group, a substituted or unsubstituted C1 to C30 aliphatic heterocyclic group, a substituted or unsubstituted C2 to C30 aromatic heterocyclic group, a substituted or unsubstituted C1 to C30 alkoxy group, a substituted or unsubstituted C6 to C30 aryloxy group, thiol group, a substituted or unsubstituted C6 to C30 alkylthio group, a substituted or unsubstituted C6 to C30 arylthio group, a cyano group, a cyano-containing group, a halogen, a halogen-containing group, a substituted or unsubstituted sulfonyl group (e.g., a substituted or unsubstituted C0 to C30 aminosulfonyl group, a substituted or unsubstituted C1 to C30 alkylsulfonyl group or a substituted or unsubstituted C6 to C30 arylsulfonyl group), or a combination thereof, or two adjacent groups of $R^{41}$ to $R^{43}$ are linked with each other to provide a fused ring, $L^1$ to $L^3$ are independently a single bond, a substituted or unsubstituted C1 to C30 alkylene group, a substituted or unsubstituted C6 to C30 arylene group, divalent substituted or unsubstituted C3 to C30 heterocyclic group, or a combination thereof, $R^{51}$ to $R^{53}$ are independently a substituted or unsubstituted C1 to C30 alkyl group, a substituted or unsubstituted C1 to C30 alkoxy group, a substituted or unsubstituted C6 to C30 aryl group, a substituted or unsubstituted C3 to C30 heterocyclic group, a substituted or unsubstituted C1 to C30 alkoxy group, a substituted or unsubstituted amine group (e.g., a substituted or unsubstituted C1 to C30 alkylamine group or a substituted or unsubstituted C6 to C30 arylamine group), a substituted or unsubstituted silyl group, or a combination thereof, and a to c are independently an integer ranging from 0 to 4.

The second p-type semiconductor compound selectively absorbing green light may be included in an amount of about 500 to about 1500 parts by weight based on 100 parts by weight of the compound represented by Chemical Formula 1.

The active layer 30 may be a single layer or a multilayer. The active layer 30 may be, for example, an intrinsic layer (I layer), a p-type layer/I layer, an I layer/n-type layer, a p-type layer/I layer/n-type layer, a p-type layer/n-type layer, and the like.

The intrinsic layer (I layer) may include the compound of Chemical Formula 1 and the n-type semiconductor compound in a ratio of about 1:100 to about 100:1. The compound of Chemical Formula 1 and the n-type semiconductor compound may be included in a ratio ranging from about 1:50 to about 50:1 within the range, specifically, about 1:10 to about 10:1, and more specifically, about 1:1. When the compound of Chemical Formula 1 and the n-type semiconductor compound have a composition ratio within the range, an exciton may be effectively produced, and a pn junction may be effectively formed.

The p-type layer may include the compound of Chemical Formula 1, and the n-type layer may include the n-type semiconductor compound.

The active layer 30 may have a thickness of about 1 nm to about 500 nm and specifically, about 5 nm to about 300 nm. When the active layer 30 has a thickness within the range, the active layer may effectively absorb light, effectively separate holes from electrons, and deliver them, thereby effectively improving photoelectric conversion efficiency. An optimal thickness of a thin film may be, for example, determined by an absorption coefficient of the active layer 30, and may be, for example, a thickness being capable of absorbing light of at least about 70% or more, for example about 80% or more, and for another example about 90%.

In the organic photoelectric device 100, when light enters from the first electrode 10 and/or second electrode 20, and when the active layer 30 absorbs light in a desired and/or alternatively predetermined wavelength region, excitons may be produced from the inside. The excitons are separated into holes and electrons in the active layer 30, and the separated holes are transported to an anode that is one of the first electrode 10 and the second electrode 20 and the separated electrons are transported to the cathode that is the other of and the first electrode 10 and the second electrode 20 so as to flow a current in the organic photoelectric device.

Hereinafter, an organic photoelectric device according to another example embodiment is described with reference to FIG. 2.

Figure 2:
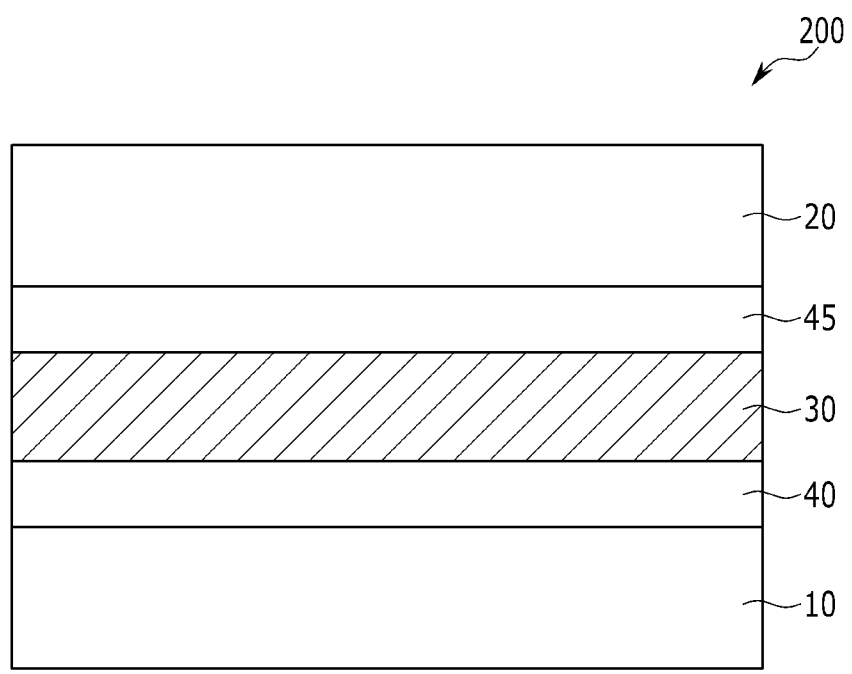
FIG. 2 is a cross-sectional view showing an organic photoelectric device according to another embodiment.

FIG. 2 is a cross-sectional view showing an organic photoelectric device according to another example embodiment.

Referring to FIG. 2, an organic photoelectric device 200 according to the present embodiment includes a first electrode 10 and a second electrode 20 facing each other, and an active layer 30 between the first electrode 10 and the second electrode 20, like the above embodiment.

However, the organic photoelectric device 200 according to the present embodiment further includes charge auxiliary layers 40 and 45 between the first electrode 10 and the active layer 30, and the second electrode 20 and the active layer 30, unlike the above embodiment. The charge auxiliary layers 40 and 45 may facilitate the transfer of holes and electrons separated from the active layer 30, so as to increase efficiency.

The charge auxiliary layers 40 and 45 may be at least one selected from a hole injection layer (HIL) for facilitating hole injection, a hole transport layer (HTL) for facilitating hole transport, an electron blocking layer (EBL) for preventing electron transport, an electron injection layer (EIL) for facilitating electron injection, an electron transport layer (ETL) for facilitating electron transport, and a hole blocking layer (HBL) for preventing hole transport.

The charge auxiliary layers 40 and 45 may include, for example, an organic material, an inorganic material, or an organic/inorganic material. The organic material may be an organic compound having hole or electron characteristics, and the inorganic material may be, for example, a metal oxide such as molybdenum oxide, tungsten oxide, nickel oxide, and the like.

The hole transport layer (HTL) may include one selected from, for example, poly(3,4-ethylenedioxythiophene):poly (styrenesulfonate) (PEDOT:PSS), polyarylamine, poly(N-vinylcarbazole), polyaniline, polypyrrole, N,N,N',N'-tetrakis(4-methoxyphenyl)-benzidine (TPD), 4-bis[N-(1-naphthyl)-N-phenyl-amino]biphenyl (α-NPD), m-MTDATA, 4,4',4"-tris(N-carbazolyl)-triphenylamine (TCTA), and a combination thereof, but is not limited thereto.

The electron blocking layer (EBL) may include one selected from, for example, poly(3,4-ethylenedioxythiophene):poly(styrenesulfonate) (PEDOT:PSS), polyarylamine, poly(N-vinylcarbazole), polyaniline, polypyrrole, N,N,N',N'-tetrakis(4-methoxyphenyl)-benzidine (TPD), 4,4'-bis[N-(1-naphthyl)-N-phenyl-amino]biphenyl (α-NPD), m-MTDATA, 4,4',4"-tris(N-carbazolyl)-triphenylamine (TCTA), and a combination thereof, but is not limited thereto.

The electron transport layer (ETL) may include one selected from, for example, 1,4,5,8-naphthalene-tetracarboxylic dianhydride (NTCDA), bathocuproine (BCP), LiF, $Alq_3$, $Gaq_3$, $Inq_3$, $Znq_2$, $Zn(BTZ)_2$, $BeBq_2$, and a combination thereof, but is not limited thereto.

The hole blocking layer (HBL) may include one selected from, for example, 1,4,5,8-naphthalene-tetracarboxylic dianhydride (NTCDA), bathocuproine (BCP), LiF, Alq$_3$, Gaq$_3$, Inq$_3$, Znq$_2$, Zn(BTZ)$_2$, BeBq$_2$, and a combination thereof, but is not limited thereto.

Either one of the charge auxiliary layers 40 and 45 may be omitted.

The organic photoelectric device may be applied to various fields, for example a solar cell, an image sensor, a photo-detector, a photo-sensor, and an organic light emitting diode (OLED), but is not limited thereto.

Hereinafter, an example of an image sensor including the organic photoelectric device is described referring to drawings. As an example of an image sensor, an organic CMOS image sensor is described.

Figure 3:
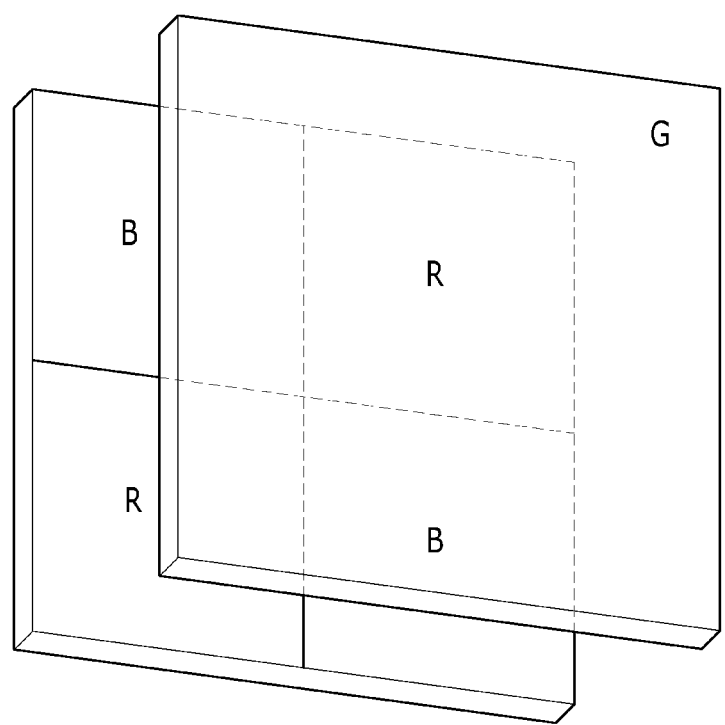
FIG. 3 is a schematic top plan view showing an organic CMOS image sensor according to an example embodiment.
Figure 4:
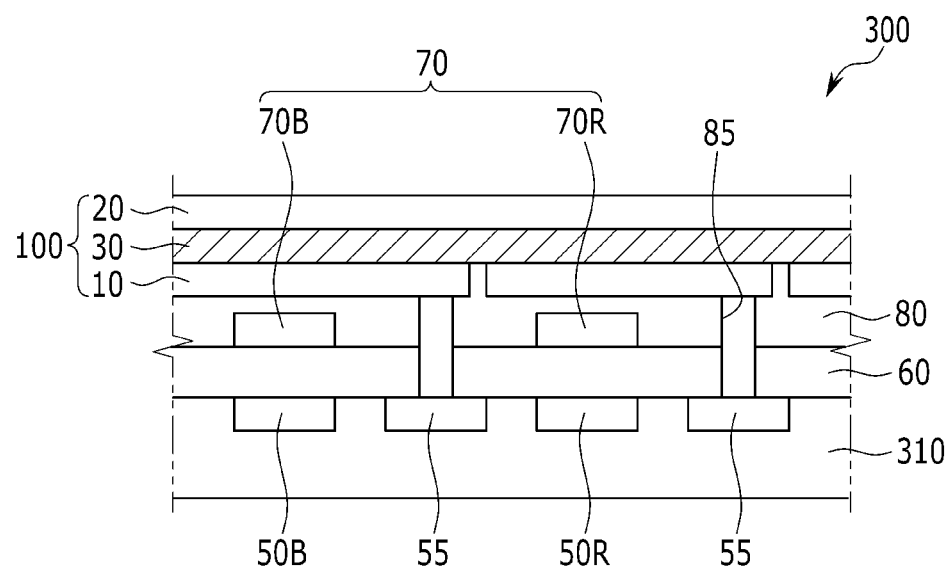
FIG. 4 is a cross-sectional view showing the organic CMOS image sensor of FIG. 3.

FIG. 3 is a schematic top plan view showing an organic CMOS image sensor according to an example embodiment, and FIG. 4 is a cross-sectional view showing the organic CMOS image sensor of FIG. 3.

Referring to FIGS. 3 and 4, an organic CMOS image sensor 300 according to an example embodiment includes a semiconductor substrate 310 integrated with photo-sensing devices 50B and 50R, a transmission transistor (not shown), a charge storage 55, a lower insulation layer 60, a color filter layer 70, an upper insulation layer 80, and an organic photoelectric device 100.

The semiconductor substrate 310 may be a silicon substrate, and is integrated with the photo-sensing device 50, the transmission transistor (not shown), and the charge storage 55. The photo-sensing devices 50R and 50B may be photodiodes.

The photo-sensing devices 50B and 50R, the transmission transistor, and/or the charge storage 55 may be integrated in each pixel, and as shown in the drawing, the photo-sensing devices 50B and 50R may be respectively included in a blue pixel and a red pixel and the charge storage 55 may be included in a green pixel.

The photo-sensing devices 50B and 50R sense light, the information sensed by the photo-sensing devices may be transferred by the transmission transistor, the charge storage 55 is electrically connected to the organic photoelectric device 100, and the information of the charge storage 55 may be transferred by the transmission transistor.

In the drawings, the photo-sensing devices 50B and 50R are, for example, arranged in parallel without limitation, and the blue photo-sensing device 50B and the red photo-sensing device 50R may be stacked in a vertical direction.

A metal wire (not shown) and a pad (not shown) are formed on the semiconductor substrate 110. In order to decrease signal delay, the metal wire and pad may be made of a metal having low resistivity, for example, aluminum (Al), copper (Cu), silver (Ag), and alloys thereof, but are not limited thereto. Further, it is not limited to the structure, and the metal wire and pad may be positioned under the photo-sensing devices 50B and 50R.

The lower insulation layer 60 is formed on the metal wire and the pad. The lower insulation layer 60 may be made of an inorganic insulating material such as a silicon oxide and/or a silicon nitride, or a low dielectric constant (low K) material such as SiC, SiCOH, SiCO, and SiOF. The lower insulation layer 60 has a trench exposing the charge storage 55. The trench may be filled with fillers.

A color filter layer 70 is formed on the lower insulation layer 60. The color filter layer 70 includes a blue filter 70B formed in the blue pixel and selectively transmitting blue light and a red filter 70R formed in the red pixel and selectively transmitting red light. In the present embodiment, a green filter is not included, but a green filter may be further included.

The color filter layer 70 may be omitted. For example, when the blue photo-sensing device 50B and the red photo-sensing device 50R are stacked in a vertical direction, the blue photo-sensing device 50B and the red photo-sensing device 50R may selectively absorb light in each wavelength region depending on their stack depth, and the color filter layer 70 may not be equipped.

The upper insulation layer 80 is formed on the color filter layer 70. The upper insulation layer 80 eliminates a step caused by the color filter layer 70 and smoothens the surface. The upper insulation layer 80 and the lower insulation layer 60 may include a contact hole (not shown) exposing a pad, and a through-hole 85 exposing the charge storage 55 of the green pixel.

The organic photoelectric device 100 is formed on the upper insulation layer 80. The organic photoelectric device 100 includes the first electrode 10, the active layer 30, and the second electrode 20 as described above.

The first electrode 10 and the second electrode 20 may be transparent electrodes, and the active layer 30 is the same as described above. The active layer 30 selectively absorbs and/or senses light in a green wavelength region and replaces a color filter of a green pixel.

When light enters from the second electrode 20, the light in a green wavelength region may be mainly absorbed in the active layer 30 and photoelectrically converted, while the light in the rest of the wavelength regions passes through first electrode 10 and may be sensed in the photo-sensing devices 50B and 50R.

As described above, the organic photoelectric devices selectively absorbing and/or sensing light in a green wavelength region are stacked and thereby a size of an image sensor may be decreased and a down-sized image sensor may be realized.

As described above, the compound represented by the Chemical Formula 1 may be used as a semiconductor compound, aggregation between compounds in a thin film state is inhibited, and thereby light absorption characteristics depending on a wavelength may be maintained. Thereby, green wavelength selectivity may be maintained, crosstalk caused by unnecessary absorption of other light except a green wavelength region may be decreased and sensitivity may be increased.

Figure 5:
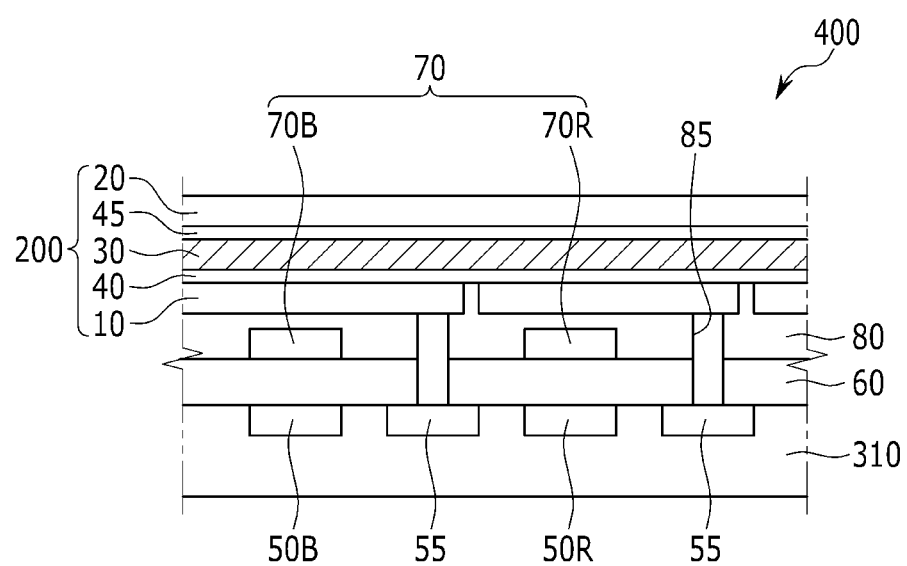
FIG. 5 is a schematic cross-sectional view showing an organic CMOS image sensor according to another example embodiment.

In FIG. 4, the organic photoelectric device 100 of FIG. 1 is included, but it is not limited thereto, and thus the organic photoelectric device 200 of FIG. 2 may be applied in the same manner. FIG. 5 shows a structure of an image sensor having such a structure, and is a cross-sectional view of an organic CMOS image sensor 400 including the organic photoelectric device 200 in FIG. 2.

Figure 6:
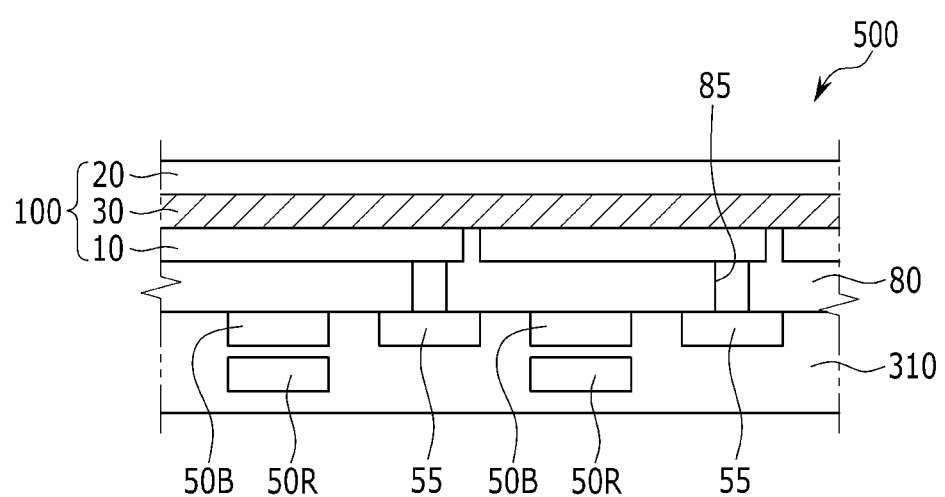
FIG. 6 is a schematic cross-sectional view showing an organic CMOS image sensor according to another example embodiment.

FIG. 6 is a cross-sectional view showing the organic CMOS image sensor according to another example embodiment.

Referring to FIG. 6, the organic CMOS image sensor 500 includes a semiconductor substrate 310 integrated with photo-sensing devices 50B and 50R, a transmission transistor (not shown), a charge storage 55, an insulation layer 80, and an organic photoelectric device 100, like the example embodiment illustrated in FIG. 5.

However, the organic CMOS image sensor 500 according to the example embodiment illustrated in FIG. 6 includes the blue photo-sensing device 50B and the red photo-sensing device 50R that are stacked and does not include a color filter layer 70, unlike the example embodiment illustrated in FIG. 5. The blue photo-sensing device 50B and the red photo-sensing device 50R are electrically connected with the charge storage 55, and the information of the charge storage 55 may be transferred by the transmission transistor (not shown). The blue photo-sensing device 50B and the red photo-sensing device 50R may selectively absorb light in each wavelength region depending on a stack depth.

As described above, the organic photoelectric devices selectively absorbing and/or sensing light in a green wavelength region are stacked and the red photo-sensing device and the blue photo-sensing device are stacked, and thereby a size of an image sensor may be decreased and a down-sized image sensor may be realized. As described above, the organic photoelectric device 100 has improved green wavelength selectivity, and crosstalk caused by unnecessary absorption light in a wavelength region except green may be decreased while increasing sensitivity.

In FIG. 6, the organic photoelectric device 100 of FIG. 1 is included, but it is not limited thereto, and thus the organic photoelectric device 200 of FIG. 2 may be applied in the same manner.

Figure 7:
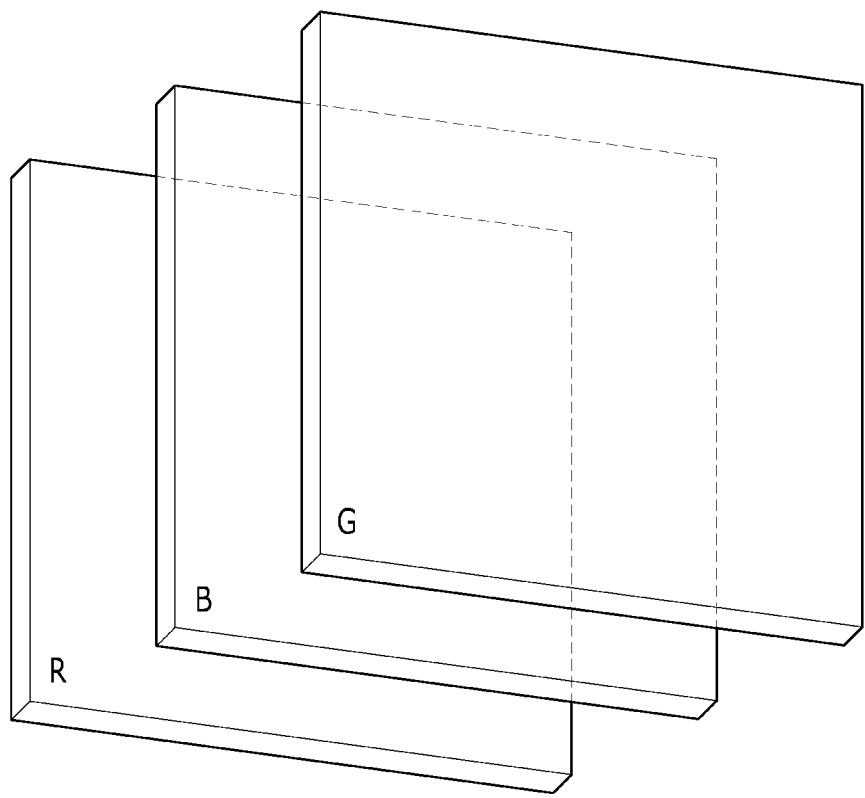
FIG. 7 is a schematic view showing an organic CMOS image sensor according to another example embodiment.

FIG. 7 is a schematic view showing an organic CMOS image sensor according to another example embodiment.

Referring to FIG. 7, the organic CMOS image sensor according to the present embodiment includes a green photoelectric device (G) selectively absorbing and/or sensing light in a green wavelength region, a blue photoelectric device (B) selectively absorbing light in a blue wavelength region, and a red photoelectric device (R) selectively absorbing and/or sensing light in a red wavelength region that are stacked.

In the drawing, the red photoelectric device (R), the blue photoelectric device (B), and the green photoelectric device (G) are sequentially stacked, but the stack order may be changed without limitation.

The green photoelectric device (G) may be the above organic photoelectric device 100, the blue photoelectric device (B) may include electrodes facing each other and an active layer interposed therebetween and including an organic material selectively absorbing light in a blue wavelength region, and the red photoelectric device (R) may include electrodes facing each other and an active layer interposed therebetween and including an organic material selectively absorbing light in a red wavelength region.

As described above, the organic photoelectric device (G) selectively absorbing and/or sensing light in a green wavelength region, the organic photoelectric device (B) selectively absorbing and/or sensing light in a blue wavelength region, and the organic photoelectric device (R) selectively absorbing and/or sensing light in a red wavelength region are stacked, and thereby a size of an image sensor may be decreased and a down-sized image sensor may be realized.

The image sensor absorbs light in an appropriate wavelength region and may show all improved sensitivity (YSNR10) and color reproducibility (ΔE*ab) despite a stack structure.

Herein, the YSNR10 indicates sensitivity of the image sensor, which is measured in a method described in Juha Alakarhu's "Image Sensors and Image Quality in Mobile Phones" printed in 2007 International Image Sensor Workshop (Ogunquit Me., USA) but minimum illuminance expressed by lux at a ratio of 10 between signal and noise. Accordingly, the smaller the YSNR10 is, the higher sensitivity is.

On the other hand, the color reproducibility (ΔE*ab) shows a difference from standard colors in an X-Rite chart and the ΔE*ab is defined as a distance between two points on a L*a*b* color space by CIE (Commission International de L' Eclairage) in 1976. For example, the color difference may be calculated according to Equation 1.

$$\Delta E = \sqrt{(\Delta L^*)^2 + (\Delta a^*)^2 + (\Delta b^*)^2}$$ [Equation 1]

In Equation 1,

ΔL* denotes a change of a color coordinate L* compared with the color coordinate L* at room temperature (about 20° C. to about 25° C.), Δa* denotes a change of a color coordinate a* compared with the color coordinate a* at room temperature, and Δb* denotes a change of a color coordinate b* compared with the color coordinate b* at room temperature.

In order to manufacture an image sensor having high color reproducibility at high sensitivity, YSNR10≤100 lux at ΔE*ab≤3, and herein, the compound may realize YSNR10≤100 lux of sensitivity and color reproducibility at ΔE*ab≤3.

The image sensor may be applied to various electronic devices, for example, a mobile phone, a digital camera, and the like but is not limited thereto.

Figure 8:
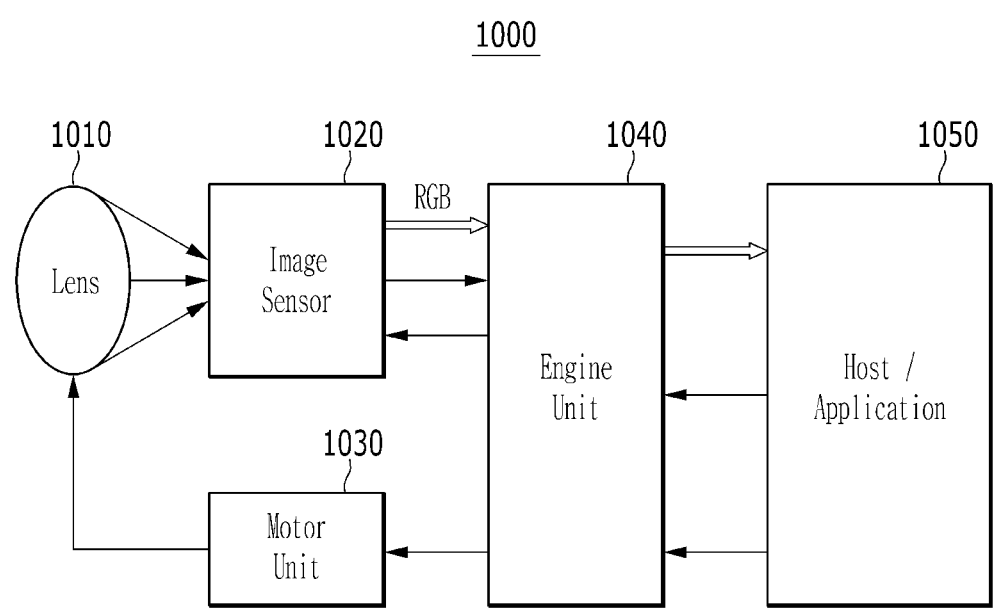
FIG. 8 is a block diagram of a digital camera including an image sensor according to an embodiment.

FIG. 8 is a block diagram of a digital camera including an image sensor according to an embodiment.

Referring to FIG. 8, a digital camera 1000 includes a lens 1010, an image sensor 1020, a motor unit 1030, and an engine unit 1040. The image sensor 1020 may be one of image sensors according to embodiments shown in FIGS. 2 to 7.

The lens 1010 concentrates incident light on the image sensor 1020. The image sensor 1020 generates RGB data for received light through the lens 1010.

In some embodiments, the image sensor 1020 may interface with the engine unit 1040.

The motor unit 1030 may adjust the focus of the lens 1010 or perform shuttering in response to a control signal received from the engine unit 1040. The engine unit 1040 may control the image sensor 1020 and the motor unit 1030.

The engine unit 1040 may be connected to a host/application 1050.

Hereinafter, the embodiments are illustrated in more detail with reference to examples. However, these examples are non-limiting, and the present disclosure is not limited thereto.

Synthesis Example 1: Synthesis of Compound 1 ((E)-3-(5-10H-phenoselenazin-10-yl)selenophen-2-yl)-2-(benzo[d]thiazol-2-yl)acrylonitrile)

[Reaction Scheme 1]

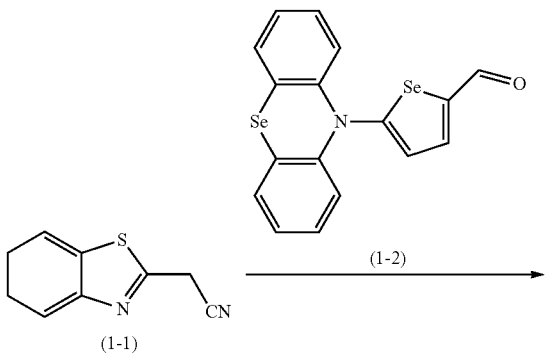

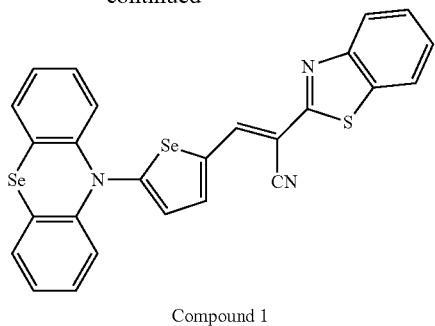

Compound 1

(1) Synthesis of Compound (1-2)

[Reaction Scheme 1A]

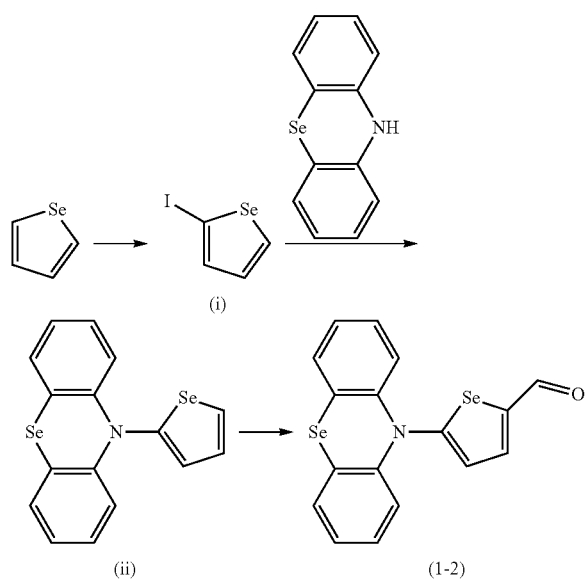

(i) Synthesis of Compound (i)

2-iodoselenophene (Compound (i)) is synthesized in a method described in Efficient Synthesis of 2-Iodo and 2-Dicyanomethyl Derivatives of Thiophene, Selenophene, Tellurophene and Thieno[3,2-b]thiophene, Takahashi, K.; Tarutani, S. Heterocycles 1996, 43, 1927-1935.

(ii) Synthesis of Compound (ii)

13.6 g (52.8 mmol) of 2-iodoselenophene and 10.0 g (40.6 mmol) of 10H-phenoselenazine are heated and refluxed in 100 ml of anhydrous toluene under presence of 5 mol % of Pd(dba)$_2$, 5 mol % of P(tBu)$_3$, and 4.29 g (44.7 mmol) of NaOtBu for 2 hours. A product therefrom is separated and purified through silica gel column chromatography (toluene: hexane in a volume ratio of 1:4) to obtain 6.89 g of Compound (ii) (10-(selenophen-2-yl)-10H-phenoselenazine, a yield: 45.2%).

(iii) Synthesis of Compound (1-2)

2.2 ml of chloridephosphoryl(phosphoryl chloride) is added in a dropwise fashion to 6.8 ml of N,N-dimethylformamide at −15° C. and then, stirred at room temperature (24° C.) for 2 hours. A resultant therefrom is slowly added in a dropwise fashion to a mixture of 180 ml of dichloromethane and 6.84 g of Compound (ii) at −15° C. and then, stirred at room temperature for 30 minutes and concentrated under a reduced pressure. Subsequently, 100 ml of water is added thereto, an aqueous sodium hydroxide solution is also added thereto until pH becomes 14, and the obtained mixture is stirred at room temperature (24° C.) for 2 hours. An organic layer is extracted therefrom with ethyl acetate and washed by an aqueous sodium chloride solution and then, dried by adding anhydrous magnesium sulfate thereto. A product obtained therefrom is separated and purified through silica gel column chromatography (hexane:dichloromethane in a volume ratio of 3:2) to obtain 5.16 g of Compound (1-2) (5-(10H-phenoselenazin-10-yl)selenophene-2-carbaldehyde, a yield: 70.4%).

(2) Synthesis of Compound 1

Compound (1-1) (2-benzothiazoleacetonitrile, 1.00 g, 5.74 mmol) and Compound (1-2) are suspended in ethanol under a nitrogen atmosphere. Piperidine (0.59 g, 6.89 mmol) is added thereto, and the mixture is stirred at 60° C. for 12 hours. The obtained mixture is cooled down to room temperature (24° C.), and a solid precipitate therein is washed with ethanol. The solid is heated and dissolved in chloroform, hexane is added thereto, and the obtained mixture is cooled down to room temperature. A precipitate therein is dried to obtain Compound 1 (1.94 g, a yield: 60%).

MS (m/z); 560.93[M+H]$^+$

Synthesis Example 2: Synthesis of Compound 2 ((E)-3-(5-10H-phenoselenazin-10-yl)selenophen-2-yl)-2-(benzo[d]thiazol-2-yl)acrylonitrile)-d)

[Reaction Scheme 2]

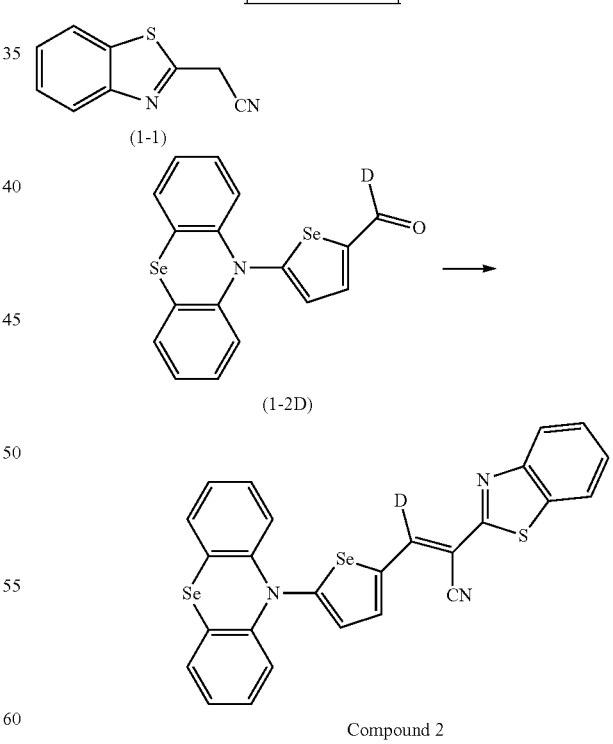

Compound 2

Compound (1-1) (2-benzothiazoleacetonitrile, 1.00 g, 5.74 mmol) and Compound (1-2D) are suspended in ethanol under an nitrogen atmosphere. Piperidine (0.59 g, 6.89 mmol) is added thereto, and the obtained mixture is stirred at 60° C. for 12 hours. The resultant is cooled down to room temperature, and a solid precipitate therein is filtered and washed with ethanol. The solid is heated and dissolved in chloroform, hexane is added thereto, and the obtained mixture is cooled down to room temperature. A solid precipitate therein is dried to obtain Compound 2 (2.25 g, a yield of 70%).

MS (m/z); 561.94[M+H]$^+$

Synthesis Example 3: Synthesis of Compound 3 ((E)-3-(5-10H-phenoselenazin-10-yl)selenophen-2-yl)-2-(naphtho[2,3-d]thiazol-2-yl)acrylonitrile)

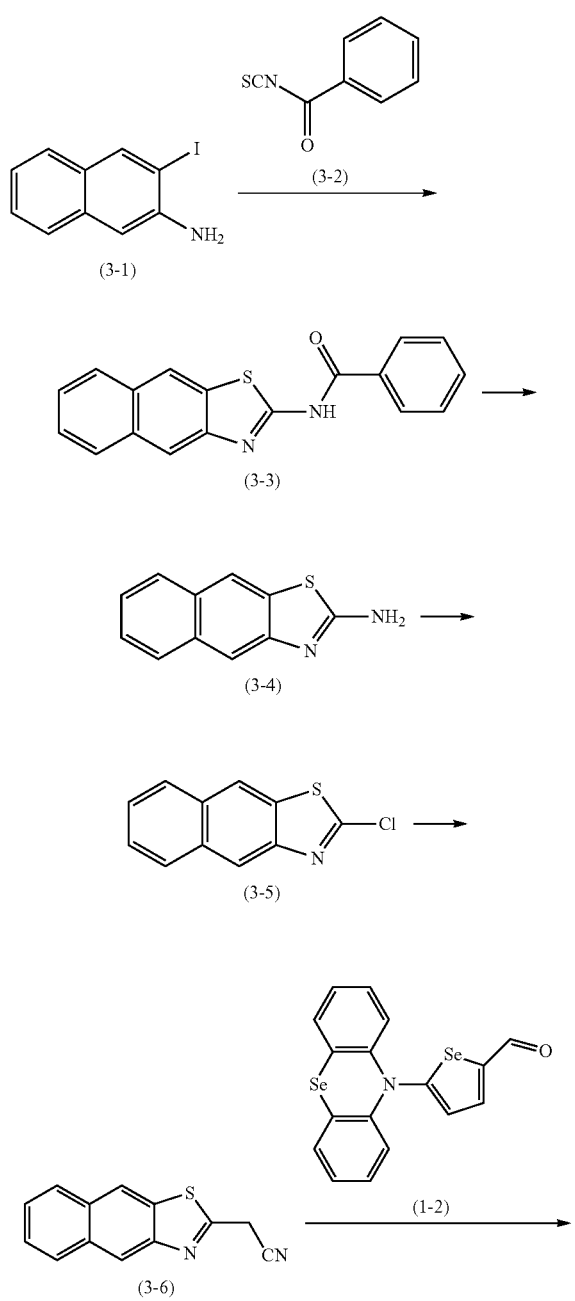

[Reaction Scheme 3]

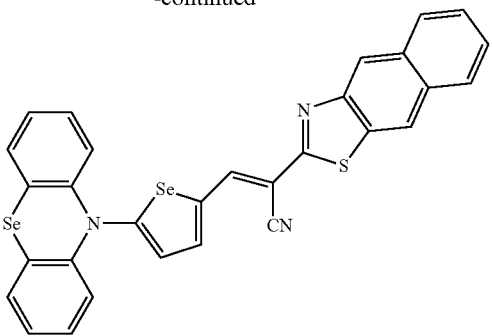

Compound 3

(1) Synthesis of Compound (3-4)

Compound (3-1) (3-iodonaphtalen-2-amine, 1.00 g, 3.72 mmol), copper iodide (0.21 g, 1.11 mmol), potassium carbonate (1.02 g, 7.44 mmol), and dimethylsulfoxide (DMSO, 37 ml) are put in a reaction vessel, after argon gas is substituted for gas therein, and then, stirred. Subsequently, Compound (3-2) (benzoylthiocyanate, 1.81 g, 11.15 mmol) is added thereto, and the obtained mixture is stirred at 90° C. for 12 hours. The resultant is cooled down to room temperature, water is added thereto, the obtained mixture is cooled down to room temperature, and water is added thereto, an organic layer is extracted therefrom with ethyl acetate and dried with anhydrous sodium sulfate, and a solvent therein is distilled under a reduced pressure and removed. A residue therefrom is purified through silica gel column chromatography (hexane:ethyl acetate in a volume ratio of 5:1) to obtain Compound (3-3) (N-(naphtho[2,3-d]thiazol-2-yl)benzamide, 0.60 g). This solid is dissolved in methanol (35 ml). Then, 10 ml of a 2N sodium hydroxide aqueous solution is added thereto, and the obtained mixture is heated and stirred for one night. Subsequently, 100 ml of water is added thereto, and a solid precipitate therein is filtered and obtained. The solid is twice washed with water (30 ml) and dried to obtain Compound (3-4) (naphtho[2,3-d]thiazole-2-amine(naphtho[2,3-d]thiazol-2-amine, 0.26 g, a yield of 35%).

$^1$H NMR (300 MHz, CDCl3): δ 8.05 (s, 1H), 7.94 (s, 1H), 7.88 (d, 1H), 7.81 (d, 1H), 7.36-7.49 (m, 2H), 5.37 (bs, 2H).

(2) Synthesis of Compound (3-5)

Dried copper chloride (II) (0.65 g, 4.79 mmol) and isoamyl nitrite (0.70 g, 5.99 mmol) are added to acetonitrile (20 mL) under an argon atmosphere at room temperature, and an acetonitrile solution (60 mL) of Compound (3-4) (naphtho[2,3-d]thiazole-2-amine, 0.80 g, 3.99 mmol) is added thereto at room temperature. The obtained mixture is heated at 65° C. and stirred at the same temperature under an argon atmosphere for 4 hours.

The reaction mixture is cooled down to room temperature, 2 M HCl (10 mL) is added thereto, and an organic layer is three times extracted therefrom with chloroform (50 mL). The organic layer is dried with anhydrous sodium sulfate, and a solvent therein is distilled under a reduced pressure and removed. A residue obtained therefrom is purified through silica gel column chromatography (hexane:ethyl acetate in a volume ratio of 2:1) to obtain Compound (3-5) (2-chloronaphtho[2,3-d]thiazole, 0.36 g, a yield of 40%).

$^1$H NMR (300 MHz, CDCl3); δ 8.43 (s, 1H), 8.25 (s, 1H), 8.01 (d, 1H), 7.91 (d, 1H), 7.51-7.56 (m, 2H).

(3) Synthesis of Compound (3-6)

Cyanoacetic acid t-butylester (0.308 g, 2.18 mmol) is dissolved in a dimethyl formamide (DMF) solution (5 ml). The obtained solution is little by little added to a 60% sodium hydride (0.11 g, 2.73 mmol) at 0° C., and the obtained mixture is stirred for 10 minutes. Subsequently, Compound (3-5) (2-chloronaphtho[2,3-d]thiazole, 0.40 g, 2.18 mmol) is added to a DMF solution (5 ml), and the obtained mixture is stirred at room temperature for 15 minutes and subsequently, at 120° C. for 2 hours. Then, a 1N hydrochloric acid aqueous solution is added thereto, and an organic layer is extracted therefrom with ethyl acetate therefrom. The organic layer is washed with water and dried with anhydrous sodium sulfate and then, concentrated under a reduced pressure. A residue therein is washed with hexane, a solid obtained therefrom is added to toluene (10 ml), p-toluenesulfonic acid monohydrate (0.10 g) is added thereto, and the obtained mixture is stirred at 100° C. for 3 hours. Then, ethyl acetate is added thereto, and the reaction solution is neutralized by adding a saturated carbonate hydrogen sodium aqueous solution thereto. An organic layer therefrom is dried with anhydrous sodium sulfate and then, concentrated under a reduced pressure. A residue therefrom is purified through silica gel column chromatography (hexane:ethyl acetate in a volume ratio of 3:1) to obtain Compound (3-6) (2-(naphtho[2,3-d]thiazol-2-yl)acetonitrile, 0.25 g, a yield of 46%).

$^1$H NMR (300 MHz, CDCl3); δ 8.54 (s, 1H), 8.38 (s, 1H), 8.05 (d, 1H), 7.94 (d, 1H), 7.52-7.57 (m, 2H), 4.28 (s, 2H).

(4) Synthesis of Compound 3

2-(naphtho[2,3-d]thiazol-2-yl)acetonitrile (0.25 g, 1.11 mmol) and Compound (1-2) are suspended in ethanol under a nitrogen atmosphere. Subsequently, piperidine (0.11 g, 1.34 mmol) is added thereto, and the obtained mixture is stirred at 60° C. for 12 hours. The resultant is cooled down to room temperature, and a solid precipitate therein is filtered and washed with ethanol. The solid is heated and dissolved in chloroform, hexane is added thereto, and the obtained mixture is cooled down to room temperature. Then, a solid precipitate therein is filtered and dried to obtain Compound 3 (0.38 g, a yield of 56%).

MS (m/z); 611.99[M+H]$^+$

Synthesis Example 4: Synthesis of Compound 4 ((E)-3-(5-10H-phenoselenazin-10-yl)selenophen-2-yl)-2-(naphtho[2,3-d]thiazol-2-yl)acrylonitrile-d)

[Reaction Scheme 4]

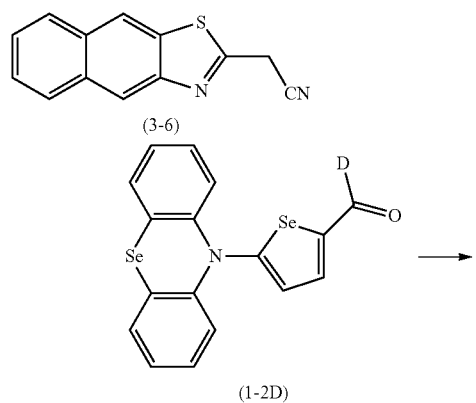

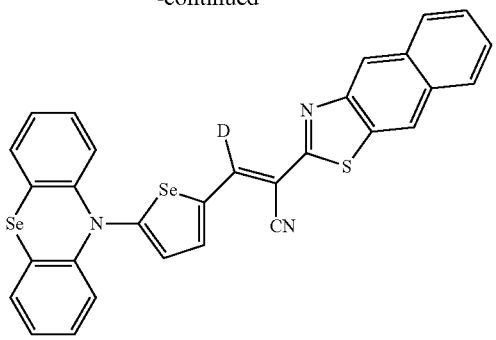

Compound 4

Compound (3-6) (2-(naphtho[2,3-d]thiazol-2-yl)acetonitrile, 1.00 g, 5.74 mmol) and Compound (1-2D) are suspended in ethanol under a nitrogen atmosphere. Piperidine (0.59 g, 6.89 mmol) is added thereto, and the obtained mixture is stirred at 60° C. for 12 hours. The resultant is cooled down to room temperature, and a solid precipitate therein is filtered and washed with ethanol. The solid is heated and dissolved in chloroform, hexane is added thereto, and the obtained mixture is cooled down to room temperature. Subsequently, a solid precipitate therein is filtered and dried to obtain Compound 4 (2.43 g, a yield of 69%).

Synthesis Example 5: Synthesis of Compound 5

[Reaction Scheme 5]

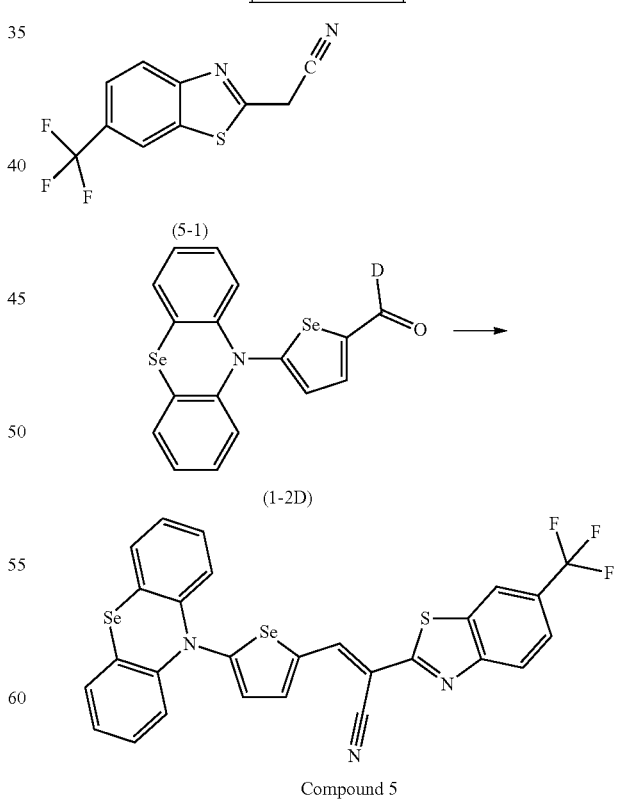

Compound 5

Compound (5-1) (2-(6-(trifluoromethyl)benzo[d]thiazol-2-yl)acetonitrile, 1.00 g) and Compound (1-2D) are suspended in ethanol under an nitrogen atmosphere. Piperidine (0.59 g, 6.89 mmol) is added thereto, and the obtained mixture is stirred at 60° C. for 12 hours. The resultant is cooled down to room temperature, and a solid precipitate therein is filtered and washed with ethanol. The solid is heated and dissolved in chloroform, hexane is added thereto, and the obtained mixture is cooled down to room temperature. A solid precipitate therein is dried to obtain Compound 5 (2.25 g, a yield of 70%).

MS (m/z); 0.43 g>99.99 (97.24+2.76)%

Reference Synthesis Example 1: Synthesis of Compound 6 (2-((5-(10H-phenoselenazin-10-yl)selenophen-2-yl)methylene)-1H-cyclopenta[b]naphthalene-1,3(2H)-dione)

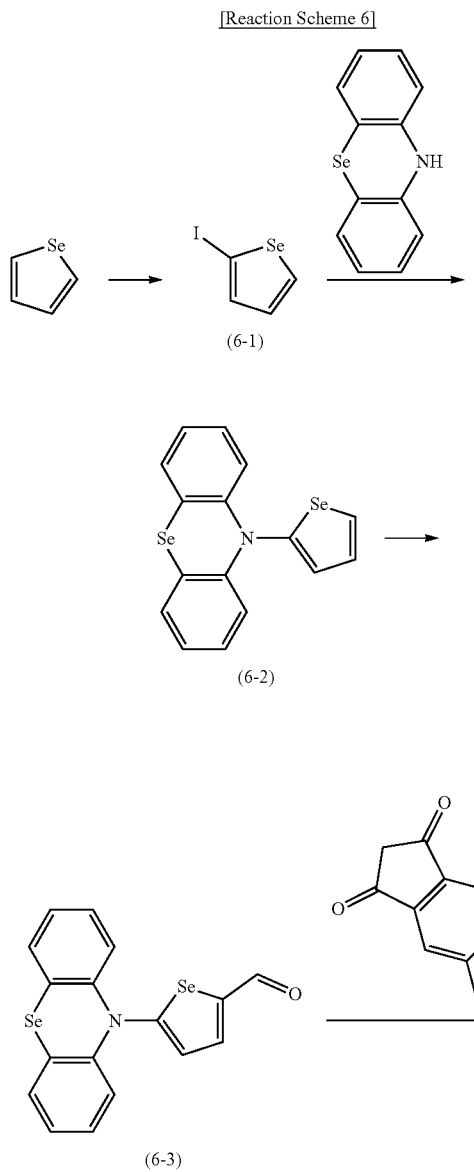

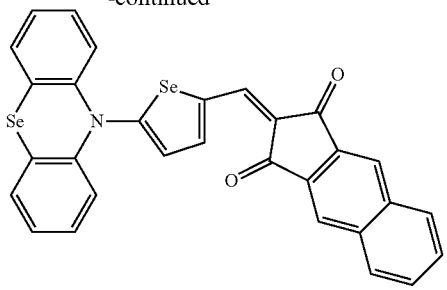

Compound 6

(1) Synthesis of Compound (6-1)

2-iodoselenophene is synthesized in a method described in Efficient Synthesis of 2-Iodo and 2-Dicyanomethyl Derivatives of Thiophene, Selenophene, Tellurophene and Thieno[3,2-b]thiophene, Takahashi, K.; Tarutani, S. Heterocycles 1996, 43, 1927-1935.

(2) Synthesis of Compound (6-2)

13.6 g (52.8 mmol) of 2-iodoselenophene and 10.0 g (40.6 mmol) of 10H-phenoselenazine is heated and refluxed in 100 ml of anhydrous toluene under presence of 5 mol % of Pd(dba)$_2$, 5 mol % of P(tBu)$_3$, and 4.29 g (44.7 mmol) of NaOtBu for 2 hours. A product obtained therefrom is separated and purified through silica gel column chromatography (toluene:hexane in a volume ratio of 1:4) to obtain Compound (6-2) (10-(selenophen-2-yl)-10H-phenoselenazine, 6.89 g, a yield of 45.2%).

(3) Synthesis of Compound (6-3)

2.2 ml of phosphoryl chloride is added in a dropwise fashion in 6.8 ml of N,N-dimethylformamide at −15° C. and then, stirred at room temperature (24° C.) for 2 hours. The resultant is slowly added in a dropwise fashion to a mixture of 180 ml of dichloromethane and 6.84 g of Compound (6-2) at −15° C., and the obtained mixture is stirred at room temperature (24° C.) for 30 minutes and concentrated under a reduced pressure. Subsequently, 100 ml of water is added thereto, an aqueous sodium hydroxide solution is added thereto until pH becomes 14, and the obtained mixture is stirred at room temperature for 2 hours. Then, an organic layer is extracted therefrom with ethyl acetate, washed with aqueous sodium chloride, and then, dried by adding anhydrous magnesium sulfate thereto. A product obtained therefrom is separated and purified through silica gel column chromatography (hexane:dichloromethane in a volume ratio of 3:2) to obtain Compound (6-3) (5-(10H-phenoselenazin-10-yl)selenophene-2-carbaldehyde, 5.16 g, a yield: 70.4%).

(4) Synthesis of Compound 6

2.00 g (4.96 mmol) of Compound (6-3) is suspended in ethanol, 1.46 g (7.44 mmol) of 1H-cyclopenta[b]naphthalene-1,3(2H)-dione is added thereto, and the obtained mixture is reacted at 50° C. for 2 hours to obtain Compound 6 (2.62 g, a yield: 72.4%). Compound 6 is sublimated and purified up to 99.8%.

$^1$H NMR ppm (DMSO) 8.34 (s)-1H, 8.32 (s)-1H, 8.27 (s)-1H, 8.24-8.16 (m)-3H, 7.98 (dd)-2H, 7.88 (dd)-2H, 7.71 (m) 2H, 7.61 (t)-2H, 7.45 (t)-2H, 6.61 (d)-1H

Reference Synthesis Example 2: Synthesis of Compound 7

[Compound 7]

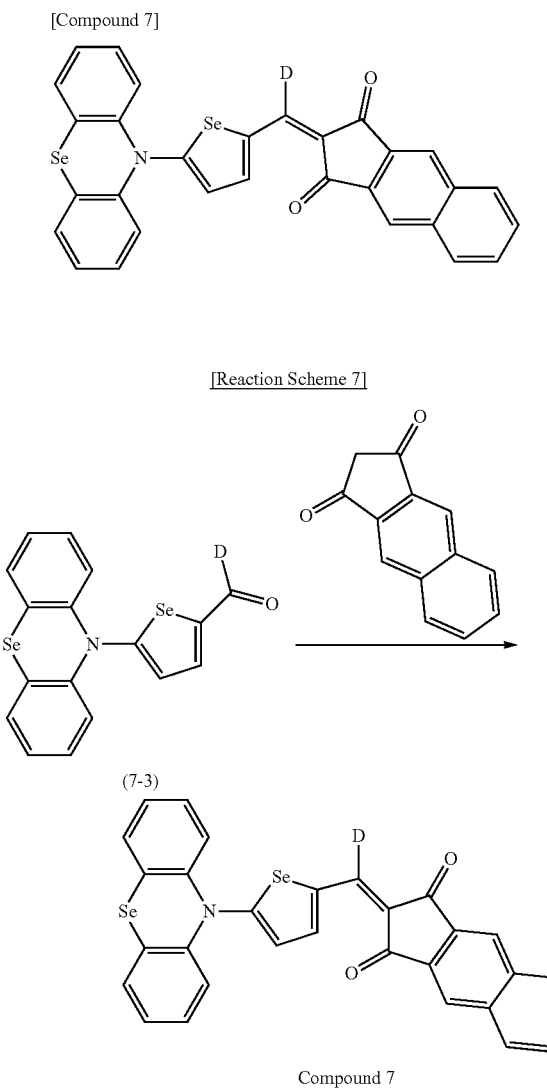

Compound 7 is synthesized according to Reaction Scheme 7 in the same method as Reference Synthesis Example 1 by using Compound (7-3) instead of Compound (6-3).

Reference Synthesis Example 3: Synthesis of Compound 8 (5-((5-(9,9-dimethylacridin-10(9H)-yl)selenophen-2-yl)methylene)-1,3-dimethyl-2-thioxodihydropyrimidine-4,6(1H,5H)-dione)

[Reaction Scheme 8]

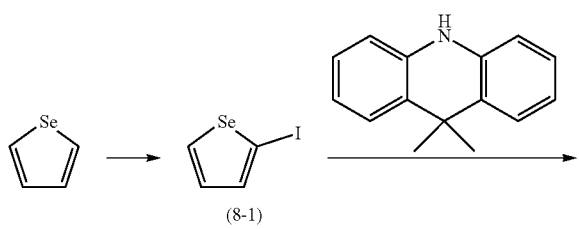

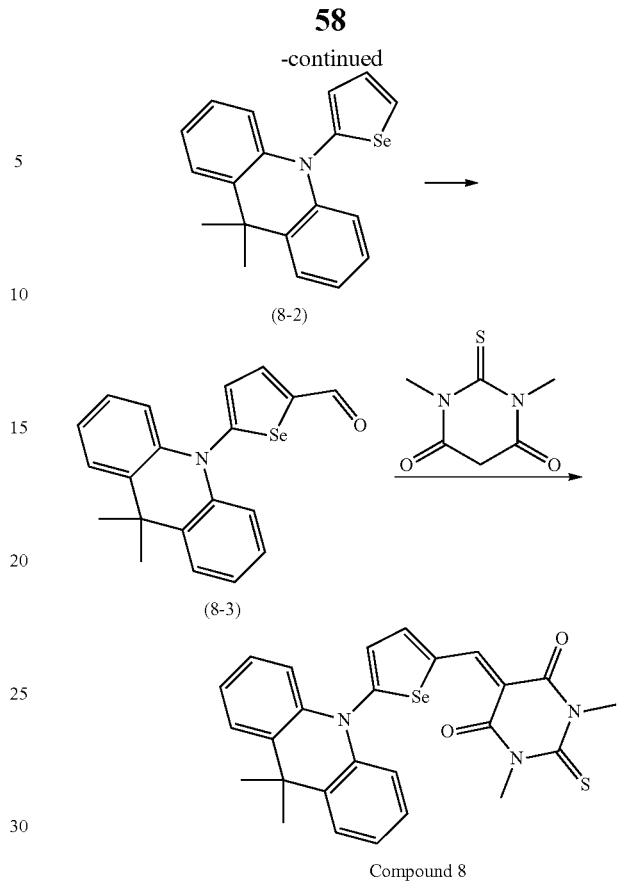

Compound 8

(1) Synthesis of Compound (8-1)

2-iodoselenophene is synthesized in a method described in Efficient Synthesis of 2-Iodo and 2-Dicyanomethyl Derivatives of Thiophene, Selenophene, Tellurophene and Thieno[3,2-b]thiophene, Takahashi, K.; Tarutani, S. Heterocycles 1996, 43, 1927-1935.

(2) Synthesis of Compound (8-2)

4.8 g (17 mmol) of 2-iodoselenophene and 2.72 g (13 mmol) of 9,10-dihydro-9,9-dimethylacridine) are heated and refluxed for 2 hours in 25 ml of anhydrous toluene under presence of 5 mol % of $Pd(dba)_2$, 5 mol % of $P(tBu)_3$, and 1.37 g (14.3 mmol) of NaOtBu. A product obtained therefrom is separated and purified through silica gel column chromatography (toluene:hexane in a volume ratio of 1:4) to obtain 0.68 g of Compound (8-2) (9,9-dimethyl-10-(selenophen-2-yl)-9,10-dihydroacridine, 2.5 g, a yield: 57%).

(3) Synthesis of Compound (8-3)

0.85 ml of phosphoryl chloride is added in a dropwise fashion to 2.64 ml of N,N-dimethylformamide at −15° C., and the mixture is stirred at room temperature (24° C.) for 2 hours. The resultant is slowly added in a dropwise fashion to a mixture of 50 ml of dichloromethane and 2.40 g of Compound (8-2) at −15° C., and the obtained mixture is stirred at room temperature (24° C.) for 30 minutes and concentrated under a reduced pressure. Subsequently, 5 ml of water is added thereto, a sodium hydroxide aqueous solution is also added thereto until pH becomes 14, and the mixture is stirred at room temperature (24° C.) for 2 hours. An organic layer extracted therefrom with ethyl acetate was washed with a sodium chloride aqueous solution and dried with anhydrous magnesium sulfate. A product obtained therefrom is separated and purified through silica gel column chromatography (hexane:dichloromethane in a volume ratio of 3:2) to obtain 0.48 g of Compound (8-3) (5-(9,9-dimethylacridin-10(9H)-yl)selenophene-2-carbaldehyde, 1.48 g, a yield: 57%).

(4) Synthesis of Compound 8

0.09 g (0.25 mmol) of Compound (8-3) is suspended in ethanol, 0.05 g (0.29 mmol) of 1,3-dimethyl-2-thiobarbituric acid synthesized according to a method described in J. Pharmacol, 1944, 82, 292, p. 4417 is added thereto, and the mixture is reacted at 50° C. for 2 hours to obtain 0.1 g of Compound 8 (a yield: 99%). Compound 8 is sublimated and purified up to purity of 99.5%.

$^1$H NMR ppm (CDCl3) 8.5 (s)-1H, 7.9 (d)-1H, 7.8 (d)-2H, 7.6 (d)-2H, 7.4 (m)-4H, 7.1 (d)-1H, 3.8 (d)-6H, 1.6 (s)-6H Light Absorption Characteristics of Compounds Each compound according to Synthesis Examples 1 to 5 and C60 are codeposited in a volume ratio of 1:1 to provide each thin film. Light absorption characteristics of each film are evaluated by using an ultraviolet (UV)-visible ray (UV-Vis) with Cary 5000 UV Spectroscopy (Varian Medical Systems). The results are shown in Table 1.

TABLE 1

|  | $\lambda_{max}$ (nm) |
| --- | --- |
| Synthesis Example 1 | 500 |
| Synthesis Example 2 | 500 |
| Synthesis Example 3 | 520 |
| Synthesis Example 4 | 520 |
| Synthesis Example 5 | 510 |

Referring to Table 1, the thin films including the compounds of Synthesis Examples 1 to 5 showed high light absorption characteristics and sufficient wavelength selectivity in a green wavelength region.

Deposition Stability of Compounds

Each compound according to Synthesis Examples 1 to 5 and Reference Synthesis Examples 1 to 3 is deposited and formed into a thin film, and purity of the thin film is measured regarding deposition stability depending on continuous deposition times. The purity is evaluated by using UPLC (Ultra Performance Liquid Chromatography). The results of Synthesis Example 2 and Reference Synthesis Examples 2 and 3 are shown in Table 2.

TABLE 2

|  | Synthesis Example 2 | Reference Synthesis Example 2 | Reference Synthesis Example 3 |
| --- | --- | --- | --- |
| 2$^{nd}$ deposition | 99.85% | 99.91% | 99.30% |
| 6$^{th}$ deposition | 99.94% | 96.09% | 89.16% |

Referring to Table 2, the compound of Synthesis Example 2 shows no purity decrease, even though consecutive deposition times are increased, and thus is not oxidized after the deposition and resultantly, shows excellent deposition stability and oxidation resistance. In other words, the compound according to Synthesis Example 2 is not decomposed despite the repetitive depositions and does not deteriorate performance of a device. On the contrary, the compounds according to Reference Synthesis Examples 2 and 3 show purity deterioration, as consecutive deposition times are increased. As for the compounds according to Reference Synthesis Examples 2 and 3, as the deposition process is repeated, a product decomposed therefrom is increased, deteriorates purity of the compounds and resultantly, performance of a device.

Deposition Temperature of Compounds

Thermal stability of the compounds according to Synthesis Examples 1 to 5 and Reference Synthesis Examples 1 to 3 is evaluated by measuring a temperature (Ts, a deposition temperature) where 10 wt % thereof is lost at 10 Pa. The loss temperature is measured through a thermogravimetric analysis (TGA). The results of Synthesis Example 2 and Reference Synthesis Example 2 are shown in Table 3.

TABLE 3

|  | Synthesis Example 2 | Reference Synthesis Example 2 |
| --- | --- | --- |
| Deposition temperature | 241° C. | 276° C. |

Referring to Table 3, the compound of Synthesis Example 2 has a lower deposition temperature than that of Reference Synthesis Example 2 and thus may be deposited without a decomposition at a low temperature and secure process stability.

Example 1: Manufacture of Organic Photoelectric Devices (1) to (6)

An about 150 nm-thick anode is formed by sputtering ITO on a glass substrate, and a 100 nm-thick active layer is formed thereon by codepositing a compound represented by Chemical Formula 1 according to Synthesis Example 1 (a p-type semiconductor compound) and C60 (a n-type semiconductor compound) in a thickness ratio of 1:1. Subsequently, a 10 nm-thick molybdenum oxide (MoOx, 0<x≤3) thin film is formed thereon as a charge auxiliary layer. On the molybdenum oxide thin film, a 7 nm-thick cathode is formed by sputtering ITO, manufacturing an organic photoelectric device (1).

An organic photoelectric device (1) is manufactured, and then, organic photoelectric devices (2) to (6) are manufactured according to the same method as that of the organic photoelectric device (1) by using the same deposition equipment.

Examples 2 to 5: Manufacture of Organic Photoelectric Devices

The organic photoelectric devices according to Examples 2 to 5 are manufactured according to the same method as Example 1 except for respectively using the compounds according to Synthesis Example 2 to 5 instead of the compound according to Synthesis Example 1. Likewise, the organic photoelectric devices are respectively manufactured by six times performing a deposition process.

Reference Examples 1 to 3: Manufacture of Organic Photoelectric Devices

Each organic photoelectric device according to Reference Examples 1 to 3 is manufactured according to the same method as Example 1 by respectively using the compounds according to Reference Synthesis Examples 1 to 3 instead of the compound according to Synthesis Example 1. Likewise, the six organic photoelectric devices are respectively manufactured by consecutively six times performing a deposition process.

External Quantum Efficiency (EQE) of Organic Photoelectric Devices

The organic photoelectric devices according to Examples 1 to 5 and Reference Examples 1 to 3 are evaluated regarding external quantum efficiency (EQE), a dark current (DC), and response time (lag time) depending on the times of deposition.

The external quantum efficiency and the dark current are measured by using an IPCE measurement system (McScience Inc., Korea). First, EQE and the dark current of the organic photoelectric devices according to Examples 1 to 5 and Reference Examples 1 to 3 are measured in a wavelength region ranging from about 350 to about 750 nm after calibrating the equipment with a Si photodiode (Hamamatsu Photonics K.K., Japan) and mounting the organic photoelectric devices on the equipment.

The response time (lag time) of the organic photoelectric devices according to Examples 1 to 5 and Reference Examples 1 to 3 is evaluated by using incident LED light having a middle wavelength of 530 nm from an upper electrode (a cathode), applying it with electric intensity of 3 V/100 nm to the organic photoelectric devices, and measuring an after-image current 0.1 second later after turning off the LED light. The results of Example 2 and Reference Examples 2 and 3 are shown in Table 4.

TABLE 4

| | Deposition number | EQE (%) | DC (h/s) | Response time (msec) |
|---|---|---|---|---|
| Synthesis Example 2 (Compound 2) | 1st | 53.2 | 1 | 82 |
| | 6th | 56.5 | 1 | 91 |
| Reference Synthesis Example 2 (Compound 6) | 1st | 65.0 | 3 | 110 |
| | 6th | 18.6 | 5 | 848 |
| Reference Synthesis Example 3 (Compound 7) | 1st | 64.3 | 4 | 650 |
| | 5th | immeasurable | immeasurable | immeasurable |

Referring to Table 4, the compound according to Synthesis Example 2 shows no deterioration of EQE and dark current characteristics and also maintains an excellent response speed, even though deposition times are increased. On the contrary, the compound according to Reference Synthesis Example 2 shows sharply-deteriorated EQE and response speed and also, deteriorated dark current characteristics, as the deposition times are increased. On the other hand, the compound according to Reference Synthesis Example 3 is almost decomposed at the 5th deposition and thus no longer deposited.

While this disclosure has been described in connection with what is presently considered to be practical example embodiments, it is to be understood that inventive concepts are not limited to the disclosed embodiments, but, on the contrary, is intended to cover various modifications and equivalent arrangements included within the spirit and scope of the appended claims.

What is claimed is:

1. A compound represented by Chemical Formula 1:

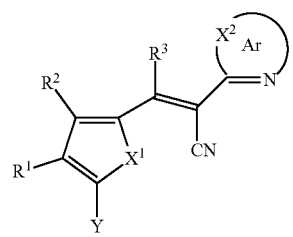

[Chemical Formula 1]

wherein, in Chemical Formula 1, $X^1$ is one of S, Se, Te, O, S(=O), S(=O)$_2$, NR$^{a1}$, SiR$^{b1}$R$^{c1}$, or GeR$^{d1}$R$^{e1}$, wherein R$^{a1}$, R$^{b1}$, R$^{c1}$, R$^{d1}$, and R$^{e1}$ are independently one of hydrogen, a substituted C1 to C10 alkyl group, or an unsubstituted C1 to C10 alkyl group, $R^1$ to $R^3$ are independently one of hydrogen, deuterium, a substituted C1 to C30 alkyl group, an unsubstituted C1 to C30 alkyl group, a substituted C1 to C30 alkoxy group, an unsubstituted C1 to C30 alkoxy group, a substituted C6 to C30 aryl group, an unsubstituted C6 to C30 aryl group, a substituted C3 to C30 heteroaryl group, an unsubstituted C3 to C30 heteroaryl group, a substituted C2 to C30 acyl group, an unsubstituted C2 to C30 acyl group, a halogen, a cyano group (—CN), a cyano-containing group, a nitro group, —SiR$^a$R$^b$R$^c$, wherein R$^a$, R$^b$, and R$^c$ are independently one of hydrogen, a substituted C1 to C10 alkyl group, or an unsubstituted C1 to C10 alkyl group, or a combination thereof, and Y is a functional group represented by Chemical Formula 2B,

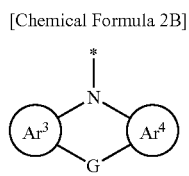

[Chemical Formula 2B]

wherein, in Chemical Formula 2B,

Ar$^3$ and Ar$^4$ are independently one of a substituted C6 to C30 arylene group, an unsubstituted C6 to C30 arylene group, a substituted C3 to C30 heteroarylene group, or an unsubstituted C3 to C30 heteroarylene group, G is one of a single bond, S, Se, Te, O, NR$^{a3}$, (CR$^{b3}$R$^{c3}$)$_n$, (C(R$^{d3}$)=C(R$^{e3}$)), SiR$^{f3}$R$^{g3}$, or GeR$^{h3}$R$^{i3}$, wherein R$^{a3}$, R$^{b3}$, R$^{c3}$, R$^{d3}$, R$^{e3}$, R$^{g3}$, R$^{h3}$, and R$^{i3}$ are independently one of hydrogen, a halogen, a substituted C1 to C10 alkyl group, an unsubstituted C1 to C10 alkyl group, a substituted C6 to C10 aryl group, or an unsubstituted C6 to C10 aryl group, and optionally R$^{d3}$ and R$^{e3}$ are independently present or are linked with each other to provide a fused ring, and n is an integer of 1 or 2, and Ar is represented by one of the structures in Chemical Formula 3A:

[Chemical Formula 3A]

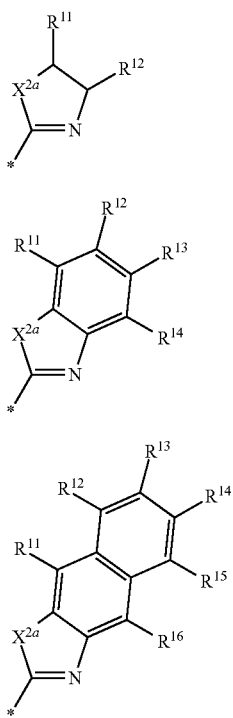

(1)

(2)

(3)

wherein, in Chemical Formula 3A, $X^{2a}$ is one of S, Se, Te, O, S(=O), S(=O)$_2$, NR$^{a2}$, CR$^{c2}$R$^{d2}$, SiR$^{e2}$R$^{f2}$, or GeR$^{g2}$R$^{h2}$, wherein, R$^{a2}$, R$^{c2}$, R$^{d2}$, R$^{e2}$, R$^{f2}$, R$^{g2}$, R$^{h2}$ are independently on of hydrogen, a substituted C1 to C10 alkyl group, or an unsubstituted C1 to C10 alkyl group, and $R^{11}$ to $R^{16}$ are independently one of hydrogen, deuterium, a substituted C1 to C30 alkyl group, an unsubstituted C1 to C30 alkyl group, a substituted C1 to C30 alkoxy group, an unsubstituted C1 to C30 alkoxy group, a substituted C6 to C30 aryl group, an unsubstituted C6 to C30 aryl group, a substituted C3 to C30 heteroaryl group, an unsubstituted C3 to C30 heteroaryl group, a substituted C2 to C30 acyl group, an unsubstituted C2 to C30 acyl group, a halogen, a cyano group (—CN), a cyano-containing group, a nitro group, —SiR$^a$R$^b$R$^c$, wherein R$^a$, R$^b$, and R$^c$ are independently one of hydrogen, a substituted C1 to C10 alkyl group, or an unsubstituted C1 to C10 alkyl group, or a combination thereof, wherein $R^{11}$ to $R^{16}$ are independently present or an adjacent two thereof are linked with each other to provide a fused ring, and wherein the compound has a maximum absorption wavelength ($\lambda_{max}$) in a wavelength region of about 500 nm to about 560 nm.

2. The compound of claim 1, wherein, in Chemical Formula 2B, at least one of Ar$^3$ and Ar$^4$ comprises a heteroatom selected from nitrogen (N), sulfur (S), and selenium (Se).

3. The compound of claim 1, wherein in Chemical Formula 1, Y is represented by Chemical Formula 2B-1 or Chemical Formula 2B-2:

[Chemical Formula 2B-1]

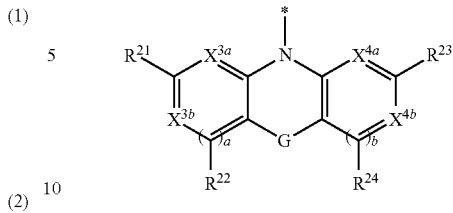

wherein, in Chemical Formula 2B-1, $X^{3a}$, $X^{3b}$, $X^{4a}$, and $X^4$b are independently one of N or CR$^a$, wherein R$^a$ is one of hydrogen, a substituted C1 to C10 alkyl group, or an unsubstituted C1 to C10 alkyl group, $R^{21}$, $R^{22}$, $R^{23}$, and $R^{24}$ are independently one of hydrogen, deuterium, a substituted C1 to C30 alkyl group, an unsubstituted C1 to C30 alkyl group, a substituted C1 to C30 alkoxy group, an unsubstituted C1 to C30 alkoxy group, a substituted C6 to C30 aryl group, an unsubstituted C6 to C30 aryl group, a substituted C3 to C30 heteroaryl group, an unsubstituted C3 to C30 heteroaryl group, a halogen, a cyano group (—CN), a cyano-containing group, or a combination thereof, a and b are independently an integer of 0 or 1, and G is one of a single bond, S, Se, Te, O, NR$^{a3}$, (CR$^{b3}$R$^{c3}$)$_n$, (C(R$^{d3}$)=C(R$^{e3}$)), SiR$^{f3}$R$^{g3}$, or GeR$^{h3}$R$^{i3}$, wherein R$^{a3}$, R$^{b3}$, R$^{c3}$, R$^{d3}$, R$^{e3}$, R$^{f3}$, R$^{g3}$, R$^{h3}$, and R$^{i3}$ are independently one of hydrogen, a halogen, a substituted C1 to C10 alkyl group, an unsubstituted C1 to C10 alkyl group, a substituted C6 to C10 aryl group, or an unsubstituted C6 to C10 aryl group, and optionally R$^{d3}$ and R$^{e3}$ are independently present or are linked with each other to provide a fused ring, and n is an integer of 1 or 2,

[Chemical Formula 2B-2]

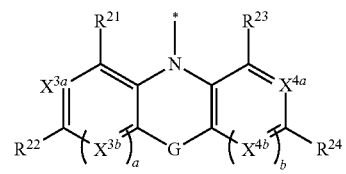

wherein, in Chemical Formula 2B-2, $X^{3a}$, $X^{3b}$, $X^{4a}$, and $X^{4b}$ are independently one of N or CR$^a$, wherein R$^a$ is one of hydrogen, a substituted C1 to C10 alkyl group, or an unsubstituted C1 to C10 alkyl group, $R^{21}$, $R^{22}$, $R^{23}$, and $R^{24}$ are independently one of hydrogen, deuterium, a substituted C1 to C30 alkyl group, an unsubstituted C1 to C30 alkyl group, a substituted C1 to C30 alkoxy group, an unsubstituted C1 to C30 alkoxy group, a substituted C6 to C30 aryl group, an unsubstituted C6 to C30 aryl group, a substituted C3 to C30 heteroaryl group, an unsubstituted C3 to C30 heteroaryl group, a halogen, a cyano group (—CN), a cyano-containing group, or a combination thereof, a and b are independently an integer of 0 or 1, and G is one of a single bond, S, Se, Te, O, NR$^{a3}$, (CR$^{b3}$R$^{e3}$)$_n$, (C(R$^{d3}$)=C(R$^{e3}$)), SiR$^{f3}$R$^{g3}$, or GeR$^{h3}$R$^{i3}$, wherein R$^{a3}$, R$^{b3}$, R$^{c3}$, R$^{d3}$, R$^{e3}$, R$^{f3}$, R$^{g3}$, R$^{h3}$, and R$^{i3}$ are independently one of hydrogen, a halogen, a substituted C1 to C10 alkyl group, an unsubstituted C1 to C10 alkyl group, a substituted C6 to C10 aryl group, or an unsubstituted C6 to C10 aryl group, and optionally $R^{d3}$ and $R^{e3}$ are independently present or are linked with each other to provide a fused ring, and n is an integer of 1 or 2.

4. The compound of claim 1, wherein the compound is represented by one of the structures in Chemical Formula 4-1:

[Chemical Formula 4-1]

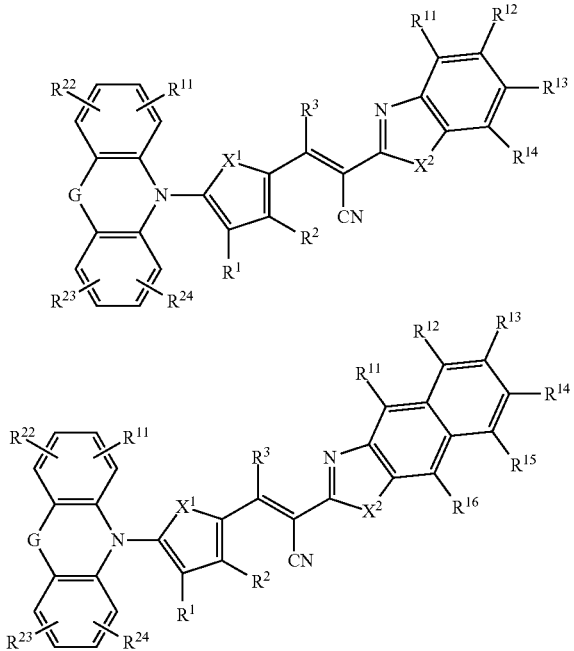

wherein, in Chemical Formula 4-1, $X^1$ is one of S, Se, Te, O, S(=O), S(=O)$_2$, NR$^{a1}$, SiR$^{b1}$R$^{c1}$, or GeR$^{d1}$R$^{e1}$, wherein R$^{a1}$, R$^{b1}$, R$^{c1}$, R$^{d1}$, and R$^{e1}$ are independently one of hydrogen, a substituted C1 to C10 alkyl group, or an unsubstituted C1 to C10 alkyl group, $X^2$ is one of S, Se, Te, O, S(=O), S(=O)$_2$, N, NR$^{a2}$, CR$^{b2}$, CR$^{e2}$R$^{d2}$, SiR$^{e2}$R$^{f2}$, or GeR$^{g2}$R$^{h2}$, wherein R$^{a2}$, R$^{b2}$, R$^{c2}$, R$^{d2}$, R$^{e2}$, R$^{f2}$, R$^{g2}$, and R$^{h2}$ are independently one of hydrogen, a substituted C1 to C10 alkyl group, or an unsubstituted C1 to C10 alkyl group, $R^1$ to $R^3$ are independently one of hydrogen, deuterium, a substituted C1 to C30 alkyl group, an unsubstituted C1 to C30 alkyl group, a substituted C1 to C30 alkoxy group, an unsubstituted C1 to C30 alkoxy group, a substituted C6 to C30 aryl group, an unsubstituted C6 to C30 aryl group, a substituted C3 to C30 heteroaryl group, an unsubstituted C3 to C30 heteroaryl group, a substituted C2 to C30 acyl group, an unsubstituted C2 to C30 acyl group, a halogen, a cyano group (—CN), a cyano-containing group, a nitro group, —SiR$^a$R$^b$R$^c$, wherein R$^a$, R$^b$, and R$^c$ are independently one of hydrogen, a substituted C1 to C10 alkyl group, or an unsubstituted C1 to C10 alkyl group, or a combination thereof, $R^{11}$ to $R^{16}$ are independently one of hydrogen, deuterium, a substituted C1 to C30 alkyl group, an unsubstituted C1 to C30 alkyl group, a substituted C1 to C30 alkoxy group, an unsubstituted C1 to C30 alkoxy group, a substituted C6 to C30 aryl group, an unsubstituted C6 to C30 aryl group, a substituted C3 to C30 heteroaryl group, an unsubstituted C3 to C30 heteroaryl group, a substituted C2 to C30 acyl group, an unsubstituted C2 to C30 acyl group, a halogen, a cyano group (—CN), a cyano-containing group, a nitro group, —SiR$^a$R$^b$R$^c$, wherein R$^a$, R$^b$, and R$^c$ are independently one of hydrogen, a substituted C1 to C10 alkyl group, or an unsubstituted C1 to C10 alkyl group, or a combination thereof, wherein $R^{11}$ to $R^{16}$ are independently present or an adjacent two thereof are linked with each other to provide a fused ring, G is one of a single bond, S, Se, Te, O, NR$^{a3}$, (CR$^{b3}$R$^{c3}$)$_n$, (C(R$^{d3}$)=C(R$^{e3}$)), SiR$^{f3}$R$^{g3}$, or GeR$^{h3}$R$^{i3}$, wherein R$^{a3}$, R$^{b3}$, R$^{c3}$, R$^{d3}$, R$^{e3}$, R$^{f3}$, R$^{g3}$, R$^{h3}$, and R$^{i3}$ are independently one of hydrogen, a halogen, a substituted C1 to C10 alkyl group, an unsubstituted C1 to C10 alkyl group, a substituted C6 to C10 aryl group, or an unsubstituted C6 to C10 aryl group, and optionally R$^{d3}$ and R$^{e3}$ are independently present or are linked with each other to provide a fused ring, and n is an integer of 1 or 2, and $R^{21}$, $R^{22}$, $R^{23}$, and $R^{24}$ are independently one of hydrogen, deuterium, a substituted C1 to C30 alkyl group, an unsubstituted C1 to C30 alkyl group, a substituted C1 to C30 alkoxy group, an unsubstituted C1 to C30 alkoxy group, a substituted C6 to C30 aryl group, an unsubstituted C6 to C30 aryl group, a substituted C3 to C30 heteroaryl group, an unsubstituted C3 to C30 heteroaryl group, a halogen, a cyano group (—CN), a cyano-containing group, or a combination thereof.

5. The compound of claim 1, wherein the compound has a maximum absorption wavelength ($\lambda_{max}$) in a wavelength region of about 510 nm to about 550 nm.

6. The compound of claim 1, wherein the compound exhibits a light absorption curve having a full width at half maximum (FWHM) of about 50 nm to about 120 nm, in a thin film state.

7. The compound of claim 1, wherein a deposition temperature at which 10 wt % of an initial weight of the compound is lost is greater than or equal to about 230° C.

8. An organic photoelectric device, comprising:
a first electrode;
a second electrode facing the first electrode; and
an active layer between the first electrode and the second electrode, wherein the active layer includes the compound of claim 1.

9. An image sensor comprising:
the organic photoelectric device of claim 8.

10. The image sensor of claim 9, further comprising:
a semiconductor substrate integrated with a plurality of first photo-sensing devices configured to sense light in a blue wavelength region and a plurality of second photo-sensing devices configured to sense light in a red wavelength region,
wherein the organic photoelectric device is on the semiconductor substrate and configured to selectively sense light in a green wavelength region.

11. The image sensor of claim 10, further comprising:
a color filter layer between the semiconductor substrate and the organic photoelectric device, wherein
the color filter layer includes a blue filter and a red filter,
the blue filter is configured to selectively transmit light in a blue wavelength region, and
the red filter is configured to selectively transmit light in a red wavelength region.

12. The image sensor of claim 10, wherein the first photo-sensing device and the second photo-sensing device are stacked in a vertical direction in the semiconductor substrate.

13. The image sensor of claim 9, further comprising:
a blue photoelectric device;
a red photoelectric device, wherein
the organic photoelectric device includes a green photoelectric device,
the green photoelectric device, the blue photoelectric device, and the red photoelectric device are stacked,
the green photoelectric device is configured to selectively sense light in a green wavelength region,
the blue photoelectric device is configured to selectively sense light in a blue wavelength region, and
the red photoelectric device is configured to selectively sense light in a red wavelength region.

14. An electronic device comprising:
the image sensor of claim 9.

15. A compound represented by Chemical Formula 1:

[Chemical Formula 1]

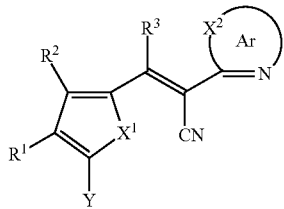

wherein, in Chemical Formula 1,
$X^1$ is one of S, Se, Te, O, S(=O), S(=O)$_2$, NR$^{a1}$, SiR$^{b1}$R$^{c1}$, or GeR$^{d1}$R$^{e1}$, wherein R$^{a1}$, R$^{b1}$, R$^{c1}$, R$^{d1}$, and R$^{e1}$ are independently one of hydrogen, a substituted C1 to C10 alkyl group, or an unsubstituted C1 to C10 alkyl group, $R^1$ to $R^3$ are independently one of hydrogen, deuterium, a substituted C1 to C30 alkyl group, an unsubstituted C1 to C30 alkyl group, a substituted C1 to C30 alkoxy group, an unsubstituted C1 to C30 alkoxy group, a substituted C6 to C30 aryl group, an unsubstituted C6 to C30 aryl group, a substituted C3 to C30 heteroaryl group, an unsubstituted C3 to C30 heteroaryl group, a substituted C2 to C30 acyl group, an unsubstituted C2 to C30 acyl group, a halogen, a cyano group (—CN), a cyano-containing group, a nitro group, —SiR$^a$R$^b$R$^c$, wherein R$^a$, R$^b$, and R$^c$ are independently one of hydrogen, a substituted C1 to C10 alkyl group, or an unsubstituted C1 to C10 alkyl group, or a combination thereof, and Y is a functional group represented by Chemical Formula 2B,

[Chemical Formula 2B]

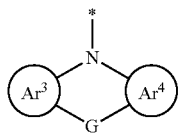

wherein, in Chemical Formula 2B,

Ar$^3$ and Ar$^4$ are independently one of a substituted C6 to C30 arylene group, an unsubstituted C6 to C30 arylene group, a substituted C3 to C30 heteroarylene group, or an unsubstituted C3 to C30 heteroarylene group, and G is one of a single bond, S, Se, Te, O, NR$^{a3}$, (CR$^{b3}$R$^{c3}$)$_n$, (C(R$^{d3}$)=C(R$^{e3}$)), SiR$^{f3}$R$^{g3}$, or GeR$^{h3}$R$^{i3}$, wherein R$^{a3}$, R$^{b3}$, R$^{c3}$, R$^{d3}$, R$^{e3}$, R$^{f3}$, R$^{g3}$, R$^{h3}$, and R$^{i3}$ are independently one of hydrogen, a halogen, a substituted C1 to C10 alkyl group, an unsubstituted C1 to C10 alkyl group, a substituted C6 to C10 aryl group, or an unsubstituted C6 to C10 aryl group, and optionally R$^{d3}$ and R$^{e3}$ are independently present or are linked with each other to provide a fused ring, and n is an integer of 1 or 2, wherein, in Chemical Formula 1, Ar includes one of the structures represented by Chemical Formulae 3A to 3E,

[Chemical Formula 3A]

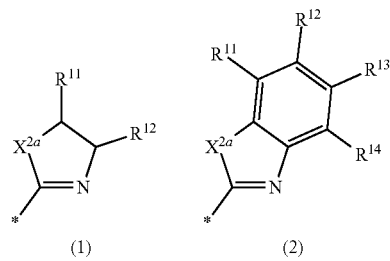

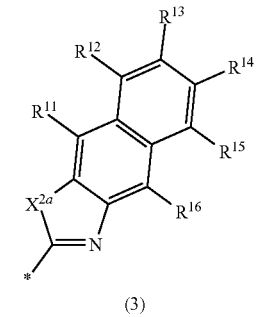

[Chemical Formula 3B]

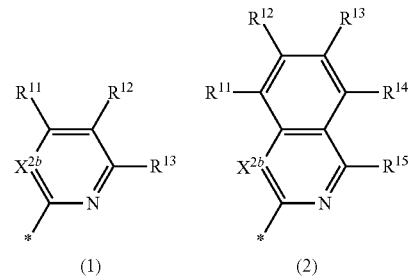

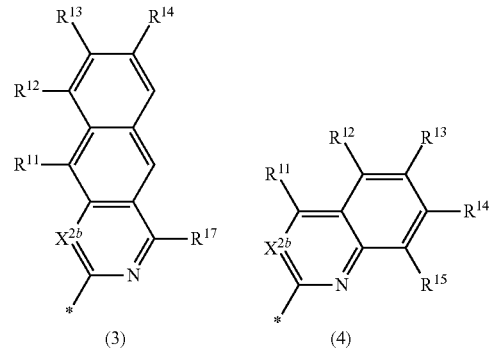

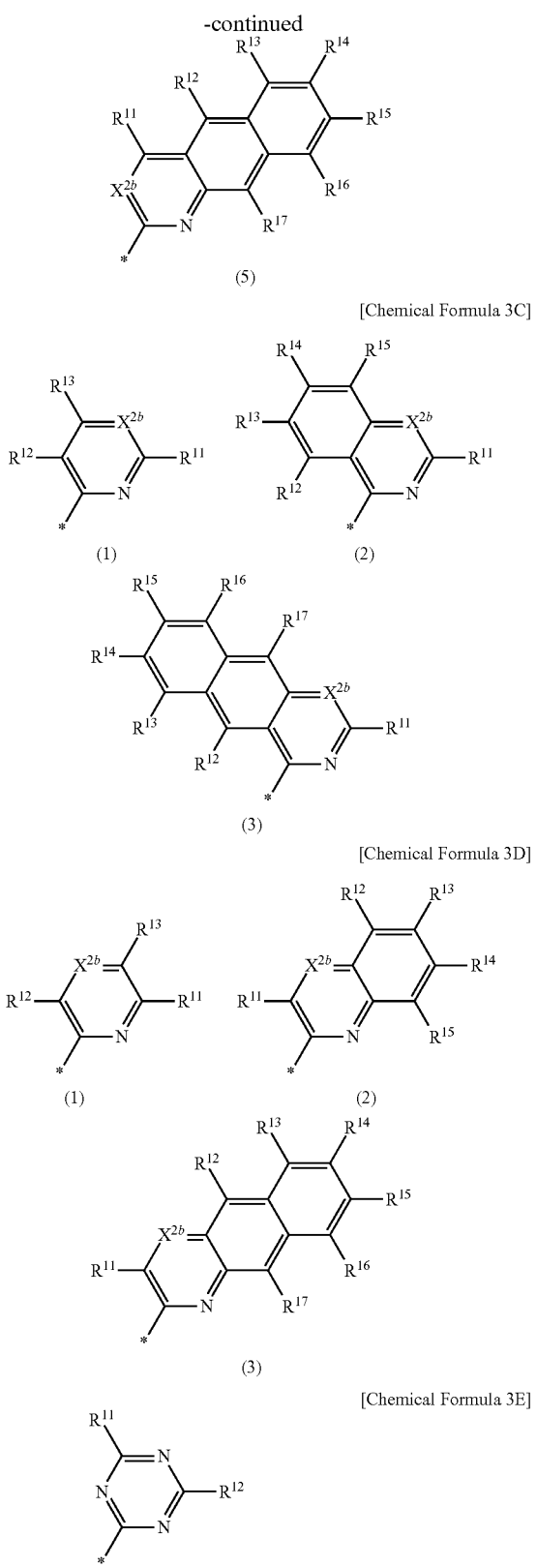

wherein, in Chemical Formula 3A,

X$^{2a}$ is one of S, Se, Te, O, S(=O), S(=O)$_2$, NR$^{a2}$, CR$^{c2}$R$^{d2}$, SiR$^{e2}$R$^{f2}$, or GeR$^{g2}$R$^{h2}$, wherein, Rae, R$^{e2}$, R$^{d2}$, R$^{e2}$, R$^{f2}$, R$^{g2}$, and R$^{h2}$ are independently one of hydrogen, a substituted C1 to C10 alkyl group, or an unsubstituted C1 to C10 alkyl group, wherein, in Chemical Formula 3B, X$^{2b}$ is one of N or CR$^{b2}$—, (wherein, R$^{b2}$ is one of hydrogen, a substituted C1 to C10 alkyl group, or an unsubstituted C1 to C10 alkyl group), and wherein, in Chemical Formulae 3C and 3D, X$^{2b}$ is N, and wherein, in Chemical Formulae 3A to 3E, R$^{11}$ to R$^{17}$ are independently one of hydrogen, deuterium, a substituted C1 to C30 alkyl group, an unsubstituted C1 to C30 alkyl group, a substituted C1 to C30 alkoxy group, an unsubstituted C1 to C30 alkoxy group, a substituted C6 to C30 aryl group, an unsubstituted C6 to C30 aryl group, a substituted C3 to C30 heteroaryl group, an unsubstituted C3 to C30 heteroaryl group, a substituted C2 to C30 acyl group, an unsubstituted C2 to C30 acyl group, a halogen, a cyano group (—CN), a cyano-containing group, a nitro group, —SiR$^a$R$^b$R$^c$, wherein R$^a$, R$^b$, and R$^c$ are independently one of hydrogen, a substituted C1 to C10 alkyl group, or an unsubstituted C1 to C10 alkyl group, or a combination thereof, and wherein, in Chemical Formulae 3A to 3D, R$^{11}$ to R$^{17}$ are independently present or an adjacent two thereof are linked with each other to provide a fused ring, wherein the compound has a maximum absorption wavelength ($\lambda_{max}$) in a wavelength region of about 500 nm to about 560 nm.

16. The compound of claim 15, wherein, in Chemical Formula 2B, at least one of Ar$^3$ and Ar$^4$ comprises a heteroatom selected from nitrogen (N), sulfur (S), and selenium (Se).

17. The compound of claim 15, wherein in Chemical Formula 1, Y is represented by Chemical Formula 2B-1 or Chemical Formula 2B-2:

[Chemical Formula 2B-1]

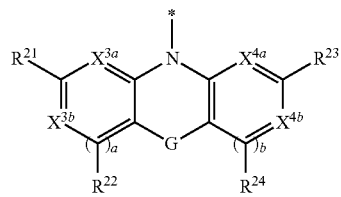

[Chemical Formula 2B-2]

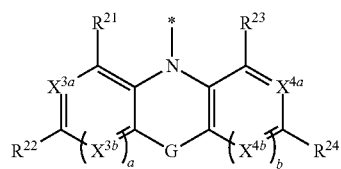

wherein, in Chemical Formula 2B-1 or Chemical Formula 2B-2,

X$^{3a}$, X$^{3b}$, X$^{3c}$, X$^{4a}$, X$^{4b}$, and X$^{4c}$ are independently one of N or CR$^a$, wherein R$^a$ is one of hydrogen, a substituted C1 to C10 alkyl group, or an unsubstituted C1 to C10 alkyl group, R$^{21}$ to R$^{25}$ are independently one of hydrogen, deuterium, a substituted C1 to C30 alkyl group, an unsubstituted C1 to C30 alkyl group, a substituted C1 to C30 alkoxy group, an unsubstituted C1 to C30 alkoxy group, a substituted C6 to C30 aryl group, an unsubstituted C6 to C30 aryl group, a substituted C3 to C30 heteroaryl group, an unsubstituted C3 to C30 heteroaryl group, a halogen, a cyano group (—CN), a cyano-containing group, or a combination thereof, a and b are independently an integer of 0 or 1, and wherein, in Chemical Formula 2B-1 and Chemical Formula 2B-2, G is one of a single bond, S, Se, Te, O, $NR^{a3}$, $(CR^{b3}R^{c3})_n$, $(C(R^{d3})=C(R^{e3}))$, $SiR^{f3}R^{g3}$, or $GeR^{h3}R^{i3}$, wherein $R^{a3}$, $R^{b3}$, $R^{c3}$, $R^{d3}$, $R^{e3}$, $R^{f3}$, $R^{g3}$, $R^{h3}$, and $R^{i3}$ are independently one of hydrogen, a halogen, a substituted C1 to C10 alkyl group, an unsubstituted C1 to C10 alkyl group, a substituted C6 to C10 aryl group, or an unsubstituted C6 to C10 aryl group, and optionally $R^{d3}$ and $R^{e3}$ are independently present or are linked with each other to provide a fused ring, and n is an integer of 1 or 23.

18. An organic photoelectric device, comprising:
the compound of claim 15 in an active layer;
a first electrode; and
a second electrode facing the first electrode, wherein the active layer is between the first electrode and the second electrode.

19. An image sensor comprising:
the organic photoelectric device of claim 18; and
a substrate, wherein
the organic photoelectric device is on the substrate.

20. The compound of claim 15, wherein in Chemical Formula 1, Ar is represented by one of the structures in Chemical Formula 3B:

[Chemical Formula 3B]

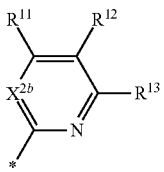
(1)

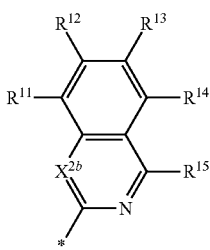
(2)

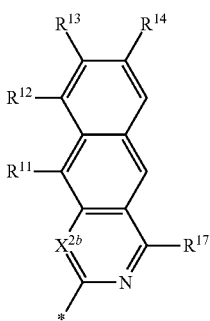
(3)

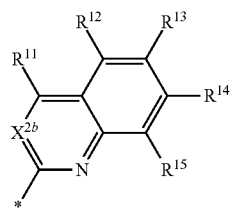
(4)

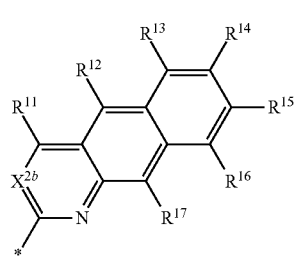
(5)

wherein, in Chemical Formula 3B, $X^{2b}$ is one of N or $CR^{b2}$, wherein, $R^{b2}$ is one of hydrogen, a substituted C1 to C10 alkyl group, or an unsubstituted C1 to C10 alkyl group, and $R^{11}$ to $R^{17}$ are independently one of hydrogen, deuterium, a substituted C1 to C30 alkyl group, an unsubstituted C1 to C30 alkyl group, a substituted C1 to C30 alkoxy group, an unsubstituted C1 to C30 alkoxy group, a substituted C6 to C30 aryl group, an unsubstituted C6 to C30 aryl group, a substituted C3 to C30 heteroaryl group, an unsubstituted C3 to C30 heteroaryl group, a substituted C2 to C30 acyl group, an unsubstituted C2 to C30 acyl group, a halogen, a cyano group (—CN), a cyano-containing group, a nitro group, —$SiR^{a}R^{b}R^{c}$, wherein $R^{a}$, $R^{b}$, and $R^{c}$ are independently one of hydrogen, a substituted C1 to C10 alkyl group, or an unsubstituted C1 to C10 alkyl group, or a combination thereof, wherein $R^{11}$ to $R^{17}$ are independently present or an adjacent two thereof are linked with each other to provide a fused ring.

21. The compound of claim 15, wherein in Chemical Formula 1, Ar is represented by one of the structures in Chemical Formula 3C:

[Chemical Formula 3C]

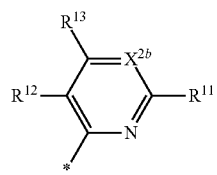
(1)

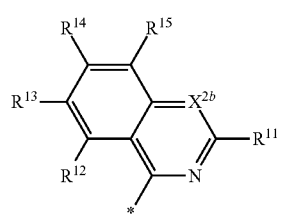
(2)

-continued (3)

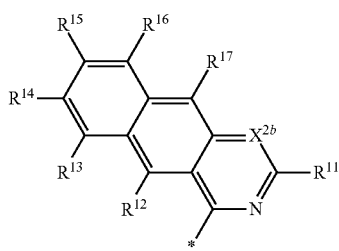

wherein, in Chemical Formula 3C, $X^{2b}$ is N, and $R^{11}$ to $R^{17}$ are independently one of hydrogen, deuterium, a substituted C1 to C30 alkyl group, an unsubstituted C1 to C30 alkyl group, a substituted C1 to C30 alkoxy group, an unsubstituted C1 to C30 alkoxy group, a substituted C6 to C30 aryl group, an unsubstituted C6 to C30 aryl group, a substituted C3 to C30 heteroaryl group, an unsubstituted C3 to C30 heteroaryl group, a substituted C2 to C30 acyl group, an unsubstituted C2 to C30 acyl group, a halogen, a cyano group (—CN), a cyano-containing group, a nitro group, —SiR$^a$R$^b$R$^c$, wherein R$^a$, R$^b$, and R$^c$ are independently one of hydrogen, a substituted C1 to C10 alkyl group, or an unsubstituted C1 to C10 alkyl group, or a combination thereof, wherein $R^{11}$ to $R^{17}$ are independently present or an adjacent two thereof are linked with each other to provide a fused ring.

22. The compound of claim 15, wherein in Chemical Formula 1, Ar is represented by one of the structures in Chemical Formula 3D:

[Chemical Formula 3D]

(1)

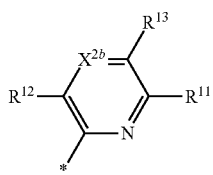

(2)

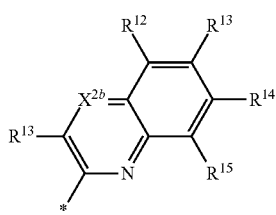

(3)

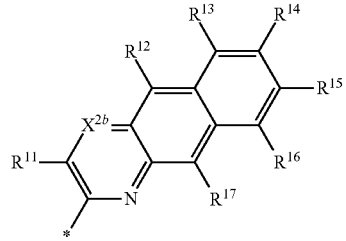

wherein, in Chemical Formula 3D, $X^{2b}$ is N, and $R^{11}$ to $R^{17}$ are independently one of hydrogen, deuterium, a substituted C1 to C30 alkyl group, an unsubstituted C1 to C30 alkyl group, a substituted C1 to C30 alkoxy group, an unsubstituted C1 to C30 alkoxy group, a substituted C6 to C30 aryl group, an unsubstituted C6 to C30 aryl group, a substituted C3 to C30 heteroaryl group, an unsubstituted C3 to C30 heteroaryl group, a substituted C2 to C30 acyl group, an unsubstituted C2 to C30 acyl group, a halogen, a cyano group (—CN), a cyano-containing group, a nitro group, —SiR$^a$R$^b$R$^c$, wherein R$^a$, R$^b$, and R$^c$ are independently one of hydrogen, a substituted C1 to C10 alkyl group, or an unsubstituted C1 to C10 alkyl group, or a combination thereof, wherein $R^{11}$ to $R^{17}$ are independently present or an adjacent two thereof are linked with each other to provide a fused ring.

23. The compound of claim 15, wherein in Chemical Formula 1, Ar is represented by Chemical Formula 3E:

[Chemical Formula 3E]

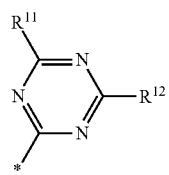

wherein, in Chemical Formula 3E, $R^{11}$ and $R^{12}$ are independently one of hydrogen, deuterium, a substituted C1 to C30 alkyl group, an unsubstituted C1 to C30 alkyl group, a substituted C1 to C30 alkoxy group, an unsubstituted C1 to C30 alkoxy group, a substituted C6 to C30 aryl group, an unsubstituted C6 to C30 aryl group, a substituted C3 to C30 heteroaryl group, an unsubstituted C3 to C30 heteroaryl group, a substituted C2 to C30 acyl group, an unsubstituted C2 to C30 acyl group, a halogen, a cyano group (—CN), a cyano-containing group, a nitro group, —SiR$^a$R$^b$R$^c$, wherein R$^a$, R$^b$, and R$^c$ are independently one of hydrogen, a substituted C1 to C10 alkyl group, or an unsubstituted C1 to C10 alkyl group, or a combination thereof.

* * * * *